US012734250B2

(12) United States Patent
Nash et al.

(10) Patent No.: US 12,734,250 B2
(45) **Date of Patent: *Sep. 15, 2026**

(54) MODIFIED UBE3A GENE FOR A GENE THERAPY APPROACH FOR ANGELMAN SYNDROME

(71) Applicant: University of South Florida, Tampa, FL (US)

(72) Inventors: Kevin Ron Nash, Seffner, FL (US); Edwin John Weeber, Apollo Beach, FL (US); Jennifer Leigh Daily, New York, NY (US)

(73) Assignee: University of South Florida, Tampa, FL (US)

(*) Notice: Subject to any disclaimer, the term of this patent is extended or adjusted under 35 U.S.C. 154(b) by 830 days.

This patent is subject to a terminal disclaimer.

(21) Appl. No.: 18/087,885

(22) Filed: Dec. 23, 2022

(65) Prior Publication Data

US 2023/0277684 A1 Sep. 7, 2023

Related U.S. Application Data

(63) Continuation of application No. 15/805,442, filed on Nov. 7, 2017, now Pat. No. 11,534,500, which is a continuation of application No. PCT/US2016/031468, filed on May 9, 2016.

(60) Provisional application No. 62/158,269, filed on May 7, 2015.

(51) Int. Cl.

| | |
|---|---|
| ***A61K 48/00*** | (2006.01) |
| ***C12N 9/00*** | (2006.01) |
| ***C12N 9/10*** | (2006.01) |
| ***C12N 15/52*** | (2006.01) |
| ***C12N 15/85*** | (2006.01) |

(52) U.S. Cl.

CPC ............ *A61K 48/005* (2013.01); *C12N 9/104* (2013.01); *C12N 9/93* (2013.01); *C12N 15/52* (2013.01); *C12N 15/85* (2013.01); *C12Y 203/02* (2013.01); *C12Y 603/02019* (2013.01); *C07K 2319/01* (2013.01); *C07K 2319/02* (2013.01); *C07K 2319/036* (2013.01); *C07K 2319/10* (2013.01); *C12N 2750/14143* (2013.01)

(58) Field of Classification Search

None

See application file for complete search history.

(56) References Cited

U.S. PATENT DOCUMENTS 6,706,505 B1 * 3/2004 Han ........................ C12N 9/93 435/254.2

FOREIGN PATENT DOCUMENTS

WO WO-2013016279 A1 * 1/2013 ......... A01K 67/0278

OTHER PUBLICATIONS

Carty et al. (PLoS One, 2013, 8(3)e59626 (Year: 2013).*
Daily et al., (PLoS One, 2011, 6:e27221, p. 1-7 (Year: 2011).*
Mah et al., (Human Gene Ther, 2003, 14:143-152) (Year: 2003).*
Garg et al., (J Immuno, 2004, 173:550-558) (Year: 2004).*
Burger et al., (Mol Ther, 2005, 11:327-331) (Year: 2005).*
EPO top-up search issued by the European Patent Office on Jan. 4, 2023 for corresponding European Patent Application No. 16790226.1.
Extended European search report issued by the European Patent Office on Feb. 27, 2023 for corresponding European Patent Application No. 22186588.4.
Official Action issued by the Canadian Intellectual Property Office on Feb. 21, 2023 for corresponding Canadian Patent Application No. 2,984,629.
Shen, Y. et al. Expressed Cell-penetrating Peptides Can Induce a Bystander Effect, but Passage Through the Secretory Pathway Reduces Protein Transduction Activity. Molecular Therapy, vol. 19, No. 5, 903-912 (May 2011).
Flinterman, M. et al. Delivery of Therapeutic Proteins as Secretable TAT Fusion Products. Molecular Therapy, vol. 17, No. 2, 334-342 (Feb. 2009).
Peng, C. et al. SPSED: A Signal Peptide Secretion Efficiency Database. Frontiers in Bioengineering and Biotechnology, vol. 9, Article 819789 (Jan. 2022).
Sato, S. et al. Evaluating Siignal Peptide Efficiency for Extracellular Protein Secretion for mRNA Vaccine Design. Biol. Pharm. Bull. vol. 48, No. 5, 706-712 (2025).

* cited by examiner

*Primary Examiner* — Arthur S Leonard
(74) *Attorney, Agent, or Firm* — Michele L. Lawson; Shumaker, Loop & Kendrick, LLP

(57) ABSTRACT

Angelman Syndrome (AS) is a genetic disorder occurring in approximately one in every 15,000 births. It is characterized by severe mental retardation, seizures, difficulty speaking and ataxia. The gene responsible for AS was discovered to be UBE3A and encodes for E6-AP, a ubiquitin ligase. A unique feature of this gene is that it undergoes maternal imprinting in a neuron-specific manner. In the majority of AS cases, there is a mutation or deletion in the maternally inherited UBE3A gene, although other cases are the result of uniparental disomy or mismethylation of the maternal gene. While most human disorders characterized by severe mental retardation involve abnormalities in brain structure, no gross anatomical changes are associated with AS. We have generated a Ube3a protein with additional sequences that should allow the secretion from cells and uptake by neighboring neuronal cells. This would confer a functional E6-AP protein into the neurons and rescue disease pathology.

9 Claims, 18 Drawing Sheets

Specification includes a Sequence Listing.

Cell lysate
Media

GDNF signal
Insulin signal
Control

SEQUENCE LISTING

```
Sequence total quantity: 15
SEQ ID NO: 1            moltype = DNA  length = 2550
FEATURE                 Location/Qualifiers
source                  1..2550
                        mol_type = genomic DNA
                        organism = Mus musculus
SEQUENCE: 1
atgaagcgag cagctgcaaa gcatctaata gaacgctact accatcagtt aactgagggc  60
tgtggaaatg aggcctgcac gaatgagttt tgtgcttcct gtccaacttt tcttcgtatg  120
gataacaatg cagcagctat taaagccctt gagctttata aaattaatgc aaaactctgt  180
gatcctcatc cctccaagaa aggagcaagc tcagcttacc ttgagaactc aaaaggtgca  240
tctaacaact cagagataaa aatgaacaag aaggaaggaa aagattttaa agatgtgatt  300
tacctaactg aagagaaagt atatgaaatt tatgaatttt gtagagagag tgaggattat  360
tcccctttaa ttcgtgtaat tggaagaata ttttctagtg ctgaggcact ggttctgagc  420
tttcggaaag tcaaacagca cacaaaggag gaattgaaat ctcttcaaga aaaggatgaa  480
gacaaggatg aagatgaaaa ggaaaaagct gcatgttctg ctgctgctat ggaagaagac  540
tcagaagcat cttcttcaag gatgggtgat agttcacagg gagacaacaa tgtacaaaaa  600
ttaggtcctg atgatgtgac tgtggatatt gatgctatta gaagggtcta cagcagtttg  660
ctcgctaatg aaaaattaga aactgccttc ctgaatgcac ttgtatatct gtcacctaac  720
gtggaatgtg atttgacata tcataatgtg tatactcgag atcctaatta tctcaatttg  780
ttcattattg taatggagaa tagtaatctc cacagtcctg aatatctgga aatggcgttg  840
ccattatttt gcaaagctat gtgtaagcta ccccttgaag ctcaaggaaa actgattagg  900
ctgtggtcta aatacagtgc tgaccagatt cggagaatga tggaaacatt tcagcaactt  960
attacctaca aagtcataag caatgaattt aatagccgaa atctagtgaa tgatgatgat  1020
gccattgttg ctgcttcaaa gtgtttgaaa atggtttact atgcaaatgt agtgggaggg  1080
gatgtggaca caaatcataa tgaggaagat gatgaagaac ccatacctga gtccagcgaa  1140
ttaacacttc aggagcttct gggagatgaa agaagaaata agaaaggtcc tcgagtggat  1200
ccactagaaa ccgaacttgg cgttaaaact ctagactgtc gaaaaccact tatctccttt  1260
gaagaattca ttaatgaacc actgaatgat gttctagaaa tggacaaaga ttataccttt  1320
ttcaaagttg aaacagagaa caaattctct tttatgacat gtccctttat attgaatgct  1380
gtcacaaaga atctgggatt atattatgac aatagaattc gcatgtacag tgaaagaaga  1440
atcactgttc tttacagcct agttcaagga cagcagttga atccgtattt gagactcaaa  1500
gtcagacgtg accatattat agatgatgca ctggtccggc tagagatgat tgctatggaa  1560
aatcctgcag acttgaagaa gcagttgtat gtggaatttg aaggagaaca aggagtaatg  1620
agggaggcgt ttccaaagag tttttcagt tgggttgtgg aggaaatttt taatccaaat  1680
attggtatgt tcacatatga tgaagctacg aaattatttt ggtttaatcc atcttctttt  1740
gaaactgagg gtcaggttta ctctgattgg catatcctgg gtctggctat ttacaataat  1800
tgtatactgg atgtccattt tcccatggtt gtatacagga agctaatggg gaaaaaagga  1860
```

```
acctttcgtg acttgggaga ctctcaccca gttttatatc agagtttaaa ggatttattg  1920
gaatatgaag ggagtgtgga agatgatatg atgatcactt tccagatatc acagacagat  1980
ctttttggta acccaatgat gtatgatcta aaagaaaatg gtgataaaat tccaattaca  2040
aatgaaaaca ggaaggaatt tgtcaatctc tattcagact acattctcaa taaatctgta  2100
gaaaaacaat tcaaggcatt tcgcagaggt tttcatatgg tgactaatga atcgccctta  2160
aaatacttat tcagaccaga agaaattgaa ttgcttatat gtggaagccg gaatctagat  2220
ttccaggcac tagaagaaac tacagagtat gacggtggct atacgaggga atctgttgtg  2280
attagggagt tctgggaaat tgttcattcg tttacagatg aacagaaaag actctttctg  2340
cagtttacaa caggcacaga cagagcacct gttggaggac taggaaaatt gaagatgatt  2400
atagccaaaa atggcccaga cacagaaagg ttacctacat ctcatacttg ctttaatgtc  2460
cttttacttc cggaatattc aagcaaagaa aaacttaaag agagattgtt gaaggccatc  2520
acatatgcca aggatttgg catgctgtaa                                   2550

SEQ ID NO: 2            moltype = DNA  length = 78
FEATURE                 Location/Qualifiers
source                  1..78
                        mol_type = genomic DNA
                        organism = Mus musculus
SEQUENCE: 2
atggccctgt tggtgcactt cctaccctg ctggccctgc ttgccctctg ggagcccaaa  60
cccacccagg cttttgtc                                               78

SEQ ID NO: 3            moltype = AA  length = 26
FEATURE                 Location/Qualifiers
source                  1..26
                        mol_type = protein
                        organism = Mus musculus
SEQUENCE: 3
MALLVHFLPL LALLALWEPK PTQAFV                                      26

SEQ ID NO: 4            moltype = DNA  length = 33
FEATURE                 Location/Qualifiers
source                  1..33
                        mol_type = genomic DNA
                        organism = Human Immunodeficiency Virus
SEQUENCE: 4
tacggcagaa agaagaggag gcagagaagg aga                              33

SEQ ID NO: 5            moltype = AA  length = 11
FEATURE                 Location/Qualifiers
source                  1..11
                        mol_type = protein
                        organism = Human Immunodeficiency Virus
SEQUENCE: 5
YGRKKRRQRR R                                                      11

SEQ ID NO: 6            moltype = DNA  length = 10893
FEATURE                 Location/Qualifiers
misc_difference         122
                        note = n is a, c, g, or t
misc_difference         340
                        note = n is a, c, g, or t
misc_difference         1145
                        note = n is a, c, g, or t
misc_difference         1180
                        note = n is a, c, g, or t
misc_difference         1257
                        note = n is a, c, g, or t
misc_difference         5410
                        note = n is a, c, g, or t
misc_difference         7624
                        note = n is a, c, g, or t
misc_difference         7644
                        note = n is a, c, g, or t
misc_difference         7647
                        note = n is a, c, g, or t
misc_difference         7741
                        note = n is a, c, g, or t
misc_difference         7836
                        note = n is a, c, g, or t
source                  1..10893
                        mol_type = genomic DNA
                        organism = Homo sapiens
SEQUENCE: 6
ggagtagttt actgagccac taatctaaag tttaatactg tgagtgaata ccagtgagta  60
cctttgttaa tgtggataac caatacttgg ctataggaag ttttttagtt gtgtgtttta  120
tnacacgtat ttgactttgt gaataattat ggcttataat ggcttgtctg ttggtatcta  180
tgtatagcgt ttacagtttc ctttaaaaaa catgcattga gtttttttaat agtccaaccc  240
ttaaaataaa tgtgttgtat ggccacctga tctgaccact ttctttcatg ttgacatctt  300
```

-continued

```
taattttaaa actgttttat ttagtgctta aatcttgttn acaaaattgt cttcctaagt  360
aatatgtcta cctttttttt tggaatatgg aatattttgc taactgtttc tcaattgcat  420
tttacagatc aggagaacct cagtctgacg acattgaagc tagccgaatg taagtgtaac  480
ttggttgaga ctgtggttct tattttgagt tgccctagac tgctttaaat tacgtcacat  540
tatttggaaa taatttctgg ttaaaagaaa ggaatcattt agcagtaaat gggagatagg  600
aacataccta ctttttttcc tatcagataa ctctaaacct cggtaacagt ttactaggtt  660
tctactacta gatagataaa tgcacacgcc taaattctta gtctttttgc ttccctggta  720
gcagttgtag ggaaataggg aggttgagga aagagtttaa cagtctcaac gcctaccata  780
tttaaggcat caagtactat gttatagata cagagatgcg taataattag ttttcaccct  840
acagaaattt atattatact caagagtgaa agatgcagaa gcaaataatt tcagtcactg  900
aggtagaatg gtatccaaaa tacaatagta acatgaagga gtactggagt accaggtatg  960
caataggaat ctagtgtaga tggcagggaa gtaagagtgg ccaggaaatg ctaagttcag  1020
tcttgaaatg tgactgggaa tcaggcagct atcaactata agtcaaatgt ttacaagctg  1080
ttaaaaatga aatactgatt atgtaaaaga aaaccggatt gatgctttaa atagactcat  1140
tttcntaatg ctaattttta aaatgataga atcctacaan tcttagctgt aaaccttgtg  1200
atttttcagc tgttgtacta aacaacttaa gcacatatac catcagacaa gcccccntcc  1260
cccctttttaa accaaaggaa tgtatactct gttaatacag tcagtaagca ttgacattct  1320
ttatcataat atcctagaaa atatttatta actatttcac tagtcaggag ttgtggtaaa  1380
tagtgcatct ccattttcta cttctcatct tcatacacag gttaatcact tcagtgcttg  1440
actaactttt gccttgatga tatgttgagc tttgtacttg agagctgtac taatcactgt  1500
gcttattgtt tgaatgtttg gtacaggaag cgagcagctg caaagcatct aatagaacgc  1560
tactaccacc agttaactga gggctgtgga aatgaagcct gcacgaatga gttttgtgct  1620
tcctgtccaa cttttcttcg tatggataat aatgcagcag ctattaaagc cctcgagctt  1680
tataagatta atgcaaaact ctgtgatcct catccctcca agaaaggagc aagctcagct  1740
taccttgaga actcgaaagg tgcccccaac aactcctgct ctgagataaa aatgaacaag  1800
aaaggcgcta gaattgattt taaaggtaag atgttttatt ttcaattgag aattgttgcc  1860
tgaaaaccat gtgggagatt taaatgtatt agtttttatt tgttttttct tctgtgacat  1920
aaagacattt tgatatcgta gaaccaattt tttattgtgg taacggacag gaataataac  1980
tacattttac aggtctaatc attgctaatt agaagcagat catatgccaa aagttcattt  2040
gttaatagat tgatttgaac tttttaaaat tcttaggaaa aatgtattaa gtggtagtga  2100
atctccaaaa ctatttaaga gctgtattat gattaatcag tacatgacat attggttcat  2160
atttataatt aaagctatac attaatagat atcttgatta taaagaaagt ttaaactcat  2220
gatcttatta agagttatac attgttgaaa gaatgtaaaa gcatgggtga ggtcattggt  2280
ataggtaggt agttcattga aaaaaatagg taagcattaa attttgtttg ctgaatctaa  2340
gtattagata ctttaagagt tgtatatcat aaatgatatt gagcctagaa tgtttggctg  2400
ttttactttt agaacttttt gcaacagagt aaacatacat attatgaaaa taaatgttct  2460
ctttttttcct ctgatttttct agatgtgact tacttaacag aagagaaggt atatgaaatt  2520
cttgaattat gtagagaaag agaggattat tcccctttaa tccgtgttat tggaagagtt  2580
ttttctagtg ctgaggcatt ggtacagagc ttccggaaag ttaaacaaca caccaaggaa  2640
gaactgaaat ctcttcaagc aaaagatgaa gacaaagatg aagatgaaaa ggaaaaagct  2700
gcatgttctg ctgctgctat ggaagaagac tcagaagcat cttcctcaag gataggtgat  2760
agctcacagg gagacaacaa tttgcaaaaa ttaggccctg atgatgtgtc tgtggatatt  2820
gatgccatta gaagggtcta caccagattg ctctctaatg aaaaaattga aactgccttt  2880
ctcaatgcac ttgtatattt gtcacctaac gtggaatgtg acttgacgta tcacaatgta  2940
tactctcgag atcctaatta tctgaatttg ttcattatcg taatggagaa tagaaatctc  3000
cacagtcctg aatatctgga aatggctttg ccattatttt gcaaagcgat gagcaagcta  3060
ccccttgcag cccaaggaaa actgatcaga ctgtggtcta aatacaatgc agaccagatt  3120
cggagaatga tggagacatt tcagcaactt attacttata aagtcataag caatgaattt  3180
aacagtcgaa atctagtgaa tgatgatgat gccattgttg ctgcttcgaa gtgcttgaaa  3240
atggtttact atgcaaatgt agtgggaggg gaagtggaca caaatcacaa tgaagaagat  3300
gatgaagagc ccatccctga gtccagcgag ctgacacttc aggaactttt gggagaagaa  3360
agaagaaaca agaaaggtcc tcgagtggac cccctggaaa ctgaacttgg tgttaaaacc  3420
ctggattgtc gaaaaccact tatccctttt gaagagttta ttaatgaacc actgaatgag  3480
gttctagaaa tggataaaga ttatactttt ttcaaagtag aaacagagaa caaattctct  3540
tttatgacat gtccctttat attgaatgct gtcacaaaga atttgggatt atattatgac  3600
aatagaattc gcatgtacag tgaacgaaga atcactgttc tctacagctt agttcaagga  3660
cagcagttga atccatattt gagactcaaa gttagacgtg accatatcat agatgatgca  3720
cttgtccggg taagttgggc tgctagatta aaaacctaat aatggggata tcatgataca  3780
gttcagtgaa ttcattttaa aagtgactga aaaaaatgat accatatagc ataggaacac  3840
atggacattt ctgatcttat ataagtatta tacttttgtt gttcctgtgc aagtttatag  3900
atgtgttcta caaagtatcg gttgtattat ataatggtca tgctatcttt gaaaaagaat  3960
gggttttcta aatcttgaaa actaaatcca aagtttcttt cattcagaag agaatagagt  4020
gttggacaaa gaccagaaca agagaaatgt ggagataccc aataataagt gtggatgtgc  4080
agtcttgaac tgggagtaat ggtacagtaa aaccatacca taaaattata ggtagtgtcc  4140
aaaaaattcc atcgtgtaaa attcagagtt gcattattgt ggacttgaag aagcagttgt  4200
atgtgggacg gtatcgataa gcttgatatc gaattcctgc agcccggggg atccactagt  4260
gtggtaatta atactaagtc ttactgtgag agaccataaa ctgctttagt attcagtgta  4320
tttttcttaa ttgaaatatt taacttatga cttagtagat actaagactt aacccttgag  4380
tttctattct aataaaggac tactaatgaa caattttgag gttagacctc tactccattg  4440
tttttgctga aatgatttag ctgcttttcc atgtcctgtg tagtccagac ttaacacaca  4500
agtaataaaa tcttaattaa ttgtatgtta atttcataac aaatcagtaa agttagcttt  4560
ttactatgct agtgtctgtt ttgtgtctgt ctttttgatt atctttaaga ctgaatcttt  4620
gtcttcactg gctttttatc agtttgcttt ctgtttccat ttacatacaa aaagtcaaaa  4680
atttgtattt gtttcctaat cctactcctt gtttttattt tgtttttttc ctgatactag  4740
caatcatctt cttttcatgt ttatcttttc aatcactagc tagagatgat cgctatggaa  4800
aatcctgcag acttgaagaa gcagttgtat gtggaatttg aaggagaaca aggagttgat  4860
gagggaggtg tttccaaaga attttttcag ctggttgtgg aggaaatctt caatccagat  4920
attggtaaat acattagtaa tgtgattatg gtgtcgtatc atcttttgag ttagttattt  4980
gtttatctta ctttgtaaat attttcagct atgaagagca gcaaaagaag gatttggtat  5040
```

-continued

```
ggattaccca gaatcacaca tcatgactga atttgtaggt tttaggaact gatttgtatc  5100
actaatttat tcaaattctt ttatttctta gaaggaatat tctaatgaag gaaattatct  5160
ctttggtaaa ctgaattgaa agcactttag aatggtatat tggaacagtt ggagggattt  5220
ctttgctttt tgttgtctaa aaccatcatc aaactcacgg ttttcctgac ctgtgaactt  5280
caaagaacaa tggtttgaag agtattgaga gactgtctca caagtatgtc atgctcaaag  5340
ttcagaaaca ctagctgata tcacattaat taggtttatt tgctataaga tttcttgggg  5400
cttaatatan gtagtgttcc cccaaacttt ttgaactcca gaactctttt ctgccctaac  5460
agtagctact caggagctga ggcaggagaa ttgtttgaac ctaggaggca gaggttgcag  5520
tgagctgaga tcgtgccact ccagcccacc cctgggtaac agagcgagac tccatctcaa  5580
agaaaaaaat gaaaaattgt tttcaaaaat agtacgtgtg gtacagatat aagtaattat  5640
atttttataa atgaaacact ttggaaatgt agccattttt tgttttttta tgtttatttt  5700
tcagctatgg gtggataaag catgaatata acttttctta tgtgttagta gaaaattaga  5760
aagcttgaat ttaattaacg tatttttcta cccgatgcca ccaaattact tactacttta  5820
ttcctttggc ttcataaaat tacatatcac cattcacccc aatttatagc agatatatgt  5880
ggacattgtt ttctcaagtg ctaatataat agaaatcaat gttgcatgcc taattacata  5940
tattttaaat gttttatatg cataattatt ttaagtttat atttgtatta ttcatcagtc  6000
cttaataaaa tacaaaagta atgtattttt aaaaatcatt tcttataggt atgttcacat  6060
acgatgaatc tacaaaattg ttttggttta atccatcttc ttttgaaact gagggtcagt  6120
ttactctgat tggcatagta ctgggtctgg ctatttacaa taactgtata ctggatgtac  6180
attttcccat ggttgtctac aggaagctaa tggggaaaaa aggaactttt cgtgacttgg  6240
gagactctca cccagtaagt tctttgtcat ttttttaatt cagtctctta gattttattt  6300
aaatgcaaaa atttaattta tgtcaaaatt ttaaagtttt tgtttagaat ctttgttgat  6360
actcttatca ataagataaa aatgttttaa tctgaccgaa gtaccagaaa cacttaaaaa  6420
ctcaaagggg gacattttta tatattgctg tcagcacgaa gctttcgtaa gattgatttc  6480
atagagaagt gtttctaaac attttgtttg tgttttagtg aaatcttaag agataggtaa  6540
aaatcagagt agccctggct aagggtcttg gtagttacaa cgagtgtgcc tgctcctacc  6600
acccccaccc ccaccttgag acaccacaga atttctcata gagcacagtg tgaattctat  6660
tgctaaattg gtggtatggg gtttctcagc agagaatggg acatcacagt gactgacaat  6720
ctttctttta taggttggaa actatttggg ggactggagg gatactgtct acacttttta  6780
caatttttat tgataagatt tttgttgtct tctaagaaga gtgatataaa ttatttgttg  6840
tattttgtag ttctatggtg gcctcaattt accatttctg gttgctaggt tctatatcag  6900
agtttaaaag atttattgga gtatgaaggg aatgtggaag atgacatgat gatcactttc  6960
cagatatcac agacagatct tttggtaac ccaatgatgt atgatctaaa ggaaaatggt  7020
gataaaattc caattacaaa tgaaaacagg aaggtaataa atgtttttat gtcacatttt  7080
gtctcttcat taacactttc aaagcatgta tgcttataat ttttaaagaa gtatctaata  7140
tagtctgtac aaaaaaaaaa caagtaacta agtttatgta aatgctagag tccacttttc  7200
taaatcttgg atataagttg gtatgaaagc acacagttgg gcactaaagc ccctttttaga  7260
gaaagaggac atgaagcagg agatagttaa tagctaagtg tggttgtagt ataaagcaag  7320
aagcagggtg tttcttgtat taagctgtaa gcaggaacct catgattaag gtctttatca  7380
cagaacaaat aaaaattaca tttaatttac acatgtatat cctgtttgtg ataaaaatac  7440
atttctgaaa agtatacttt acgtcagatt tgggttctat tgactaaaat gtgttcatcg  7500
ggaatgggaa taacccagaa cataacaagc aaaaaaatat gacaaatata tagtatacct  7560
ttaagaaaca tgtttatatt gatataattt tttgattaaa tattatacac actaagggta  7620
caangcacat tttccttttta tganttngat acagtagttt atgtgtcagt cagatacttc  7680
cacatttttg ctgaactgga tacagtaagc agcttaccaa atattctatg gtagaaaact  7740
nggacttcct ggtttgctta aatcaaatat attgtactct cttaaaacgg ttggcattta  7800
taaatagatg gatacatggt ttaaatgtgt ctgttnacat acctagttga gagaacctaa  7860
agaattttct gcgtctccag catttatatt cagttctgtt taatacatta tcgaaattga  7920
catttataag tatgacagtt ttgtgtatat ggccttttca tagcttaata ttggctgtaa  7980
cagagaattg tgaaattgta agaagtagtt ttctttgtag gtgtaaaatt gaatttttaa  8040
gaatattctt gacagtttta tgtatatggc cttttcatag cttaatattg gctataacag  8100
agaattgtga aattgttaag aagtaggtgt aaaattgaat ttttaagaat attcttgaat  8160
gttttttttct tggaaaaatt aaaaagctat gcagcccaat aacttgtgtt ttgtttgcat  8220
agcatattat aagaagttct tgtgattaat gttttctaca ggaatttgtc aatctttatt  8280
ctgactacat tctcaataaa tcagtagaaa aacagttcaa ggcttttcgg agaggttttc  8340
atatggtgac caatgaatct ccccttaaagt acttattcag accagaagaa attgaattgc  8400
ttatatgtgg aagccgggta agaaagcagg tgtctgcaaa aagtcatgta tcgatttatt  8460
gtttgtaatg atacagtagt atagcagata actaagacat attttcttga atttgcagaa  8520
tctagatttc caagcactag aagaaactac agaatatgac ggtggctata ccagggactc  8580
tgttctgatt aggtgaggta cttagttctt cagaggaaga tttgattcac caaaggggtg  8640
tgtgattttg cttcagacct ttatctctag gtactaattc ccaaataagc aaactcacaa  8700
attgtcatct atatacttag atttgtattt gtaatataat caccattttt cagagctaat  8760
cttgtgattt atttcatgaa tgaagtgttg ttatatataa gtctcatgta atctcctgca  8820
tttggcgtat ggattatcta gtattcctca ctggttagag tatgcttact gctggttaga  8880
agataattaa aataaggcta ccatgtctgc aatttttcct ttcttttgaa ctctgcattt  8940
gtgaactgtt acatggcttc ccaggatcaa gcacttttttg agtgaaatgg tagtctttta  9000
tttaattctt aagataatat gtccagatac atactagtat ttccatttta caccctaaaa  9060
aactaagccc tgaattctca cagaaagatg tagaggttcc cagttctatc tgcttttaaa  9120
caaatgccct tactactcta ctgtctactt ctgtgtacta catcatcgta tgtagttgtt  9180
tgcatttggg ccagttggtt ggggcagggg tcttttttttc ttttgtccct taatctgtat  9240
cactttttcc tcccaaagtt gagttaaagg atgagtagac caggagaata aaggagaaag  9300
gataaataaa atatataccc aaaggcacct ggagttaatt tttccaaata ttcatttcag  9360
tctttttcaa ttcataggat tttgtctttt gctcattact gactgcataa tgtgattata  9420
ccatagttta aatagtcact tcctgttact acacacttgg gtttctcaa tttttacta  9480
ttgtagtact aatattttac tatattgtaa tctaatccaa atttttacgt attcagagct  9540
gttcaggata aatttgcttg gaaattttta aatcaccaga agtgatacta tcctgataat  9600
taacttccaa gttgtctctt aatatagttt taatgcaaat cataagctta tgttagtacc  9660
agtcataatg aatgccaaac tgaaaccagt attgtatttt ttctcattag ggagttctgg  9720
gaaatcgttc attcatttac agatgaacag aaaagactct tcttgcagtt tacaacgggc  9780
```

```
acagacagag cacctgtggg aggactagga aaattaaaga tgattatagc caaaaatggc  9840
ccagacacag aaaggtaggt aattattaac ttgtgactgt atacctaccg aaaaccttgc  9900
attcctcgtc acatacatat gaactgtctt tatagtttct gagcacattc gtgattttat  9960
atacaaatcc ccaaatcata ttagacaatt gagaaaatac tttgctgtca ttgtgtgagg  10020
aaacttttaa gaaattgccc tagttaaaaa ttattatggg gctcacattg gtttggaatc  10080
aaattagtgt gattcattta ctttttttgat tcccagcttg ttaattgaaa gccatataac  10140
atgatcatct atttagaatg gttacattga ggctcggaag attatcattt gattgtgcta  10200
gaatcctgtt atcaaatcat tttcttagtc atattgccag cagtgtttct aataagcatt  10260
taagagcaca cactttgcag tcttgtaaaa caggtttgag tattttctcc accttagagg  10320
aagttacttg acttctcagt gacctaacct ctaaagtgca tttactgatg tcctctctgt  10380
ggttttgttg tggaaagatt tagttaaatg aactgtaaga attcagtacc taaaatggta  10440
tctgttatgt agtaaaaact caatggatac agtatcttat catcgtcact agctttgagt  10500
aatttatagg ataaaggcaa cttggtagtt acacaacaaa aagtttatga tttgcattaa  10560
tgtatagttt gcattgcaga ccgtctcaac tatatacaat ctaaaaatag gagcatttaa  10620
ttctaagtgt atttcccatg acttacagtt ttcctgtttt tttccccttt tctctattta  10680
ggttacctac atctcatact tgctttaatg tgcttttact tccggaatac tcaagcaaag  10740
aaaaacttaa agagagattg ttgaaggcca tcacgtatgc caaaggattt ggcatgctgt  10800
aaaacaaaac aaaacaaaat aaaacaaaaa aaaggaagga aaaaaaaaga aaaaatttaa  10860
aaaattttaa aaatataacg agggataaat ttt                              10893

SEQ ID NO: 7            moltype = AA  length = 852
FEATURE                 Location/Qualifiers
source                  1..852
                        mol_type = protein
                        organism = Homo sapiens
SEQUENCE: 7
MKRAAAKHLI ERYYHQLTEG CGNEACTNEF CASCPTFLRM DNNAAAIKAL ELYKINAKLC  60
DPHPSKKGAS SAYLENSKGA PNNSCSEIKM NKKGARIDFK DVTYLTEEKV YEILELCRER  120
EDYSPLIRVI GRVFSSAEAL VQSFRKVKQH TKEELKSLQA KDEDKDEDEK EKAACSAAAM  180
EEDSEASSSR IGDSSQGDNN LQKLGPDDVS VDIDAIRRVY TRLLSNEKIE TAFLNALVYL  240
SPNVECDLTY HNVYSRDPNY LNLFIIVMEN RNLHSPEYLE MALPLFCKAM SKLPLAAQGK  300
LIRLWSKYNA DQIRRMMETF QQLITYKVIS NEFNSRNLVN DDDAIVAASK CLKMVYYANV  360
VGGEVDTNHN EEDDEEPIPE SSELTLQELL GEERRNKKGP RVDPLETELG VKTLDCRKPL  420
IPFEEFINEP LNEVLEMDKD YTFFKVETEN KFSFMTCPFI LNAVTKNLGL YYDNRIRMYS  480
ERRITVLYSL VQGQQLNPYL RLKVRRDHII DDALVRLEMI AMENPADLKK QLYVEFEGEQ  540
GVDEGGVSKE FFQLVVEEIF NPDIGMFTYD ESTKLFWFNP SSFETEGQFT LIGIVLGLAI  600
YNNCILDVHF PMVVYRKLMG KKGTFRDLGD SHPVLYQSLK DLLEYEGNVE DDMMITFQIS  660
QTDLFGNPMM YDLKENGDKI PITNENRKEF VNLYSDYILN KSVEKQFKAF RRGFHMVTNE  720
SPLKYLFRPE EIELLICGSR NLDFQALEET TEYDGGYTRD SVLIREFWEI VHSFTDEQKR  780
LFLQFTTGTD RAPVGGLGKL KMIIAKNGPD TERLPTSHTC FNVLLLPEYS SKEKLKERLL  840
KAITYAKGFG ML                                                     852

SEQ ID NO: 8            moltype = DNA  length = 57
FEATURE                 Location/Qualifiers
source                  1..57
                        mol_type = genomic DNA
                        organism = Homo sapiens
SEQUENCE: 8
atgaagttat gggatgtcgt ggctgtctgc ctggtgctgc tccacaccgc gtccgcc     57

SEQ ID NO: 9            moltype = DNA  length = 72
FEATURE                 Location/Qualifiers
source                  1..72
                        mol_type = genomic DNA
                        organism = Homo sapiens
SEQUENCE: 9
atggccctgt ggatgcgcct cctgcccctg ctggcgctgc tggccctctg gggacctgac  60
ccagccgcag cc                                                     72

SEQ ID NO: 10           moltype = DNA  length = 60
FEATURE                 Location/Qualifiers
source                  1..60
                        mol_type = genomic DNA
                        organism = Homo sapiens
SEQUENCE: 10
atggagacag acacactcct gctatgggta ctgctgctct gggttccagg ttccactggt  60

SEQ ID NO: 11           moltype = AA  length = 11
FEATURE                 Location/Qualifiers
source                  1..11
                        mol_type = protein
                        organism = Human Immunodeficiency Virus
SEQUENCE: 11
YARKAARQAR A                                                      11
```

```
SEQ ID NO: 12           moltype = DNA  length = 2767
FEATURE                 Location/Qualifiers
source                  1..2767
                        mol_type = genomic DNA
                        organism = Homo sapiens
SEQUENCE: 12
acagtatgac atctgatgct ggagggtcgc actttcacaa atgagtcagc tggtacatgg  60
ggttatcatc aatttttagc tcttctgtct gggagataca agtttggaag caatcttggg  120
gtacttaccc acaaggctgg tggagaccag atcaggagaa cctcagtctg acgacattga  180
agctagccga atgaagcgag cagctgcaaa gcatctaata gaacgctact accaccagtt  240
aactgagggc tgtggaaatg aagcctgcac gaatgagttt tgtgcttcct gtccaacttt  300
tcttcgtatg gataataatg cagcagctat taaagccctc gagctttata agattaatgc  360
aaaactctgt gatcctcatc cctccaagaa aggagcaagc tcagcttacc ttgagaactc  420
gaaaggtgcc cccaacaact cctgctctga gataaaaatg aacaagaaag gcgctagaat  480
tgattttaaa gatgtgactt acttaacaga agagaaggta tatgaaattc ttgaattatg  540
tagagaaaga gaggattatt cccctttaat ccgtgttatt ggaagagttt tttctagtgc  600
tgaggcattg gtacagagct tccggaaagt taaacaacac accaaggaag aactgaaatc  660
tcttcaagca aaagatgaag acaaagatga ggatgaaaag gaaaaagctg catgttctgc  720
tgctgctatg gaagaagact cagaagcatc ttcctcaagg ataggtgata gctcacaggg  780
agacaacaat ttgcaaaaat taggccctga tgatgtgtct gtggatattg atgccattag  840
aagggtctac accagattgc tctctaatga aaaaattgaa actgcctttc tcaatgcact  900
tgtatatttg tcacctaacg tggaatgtga cttgacgtat cacaatgtat actctcgaga  960
tcctaattat ctgaatttgt tcattatcgt aatggagaat agaaatctcc acagtcctga  1020
atatctggaa atggctttgc cattattttg caaagcgatg agcaagctac cccttgcagc  1080
ccaaggaaaa ctgatcagac tgtggtctaa atacaatgca gaccagattc ggagaatgat  1140
ggagacattt cagcaactta ttacttataa agtcataagc aatgaattta acagtcgaaa  1200
tctagtgaat gatgatgatg ccattgttgc tgcttcgaag tgcttgaaaa tggtttacta  1260
tgcaaatgta gtgggagggg aagtggacac aaatcacaat gaagaagatg atgaagagcc  1320
catccctgag tccagcgagc tgacacttca ggaacttttg ggagaagaaa gaagaaacaa  1380
gaaaggtcct cgagtggacc ccctggaaac tgaacttggt gttaaaaccc tggattgtcg  1440
aaaaccactt atccctttg aagagtttat taatgaacca ctgaatgagg ttctagaaat  1500
ggataaagat tatacttttt tcaaagtaga aacagagaac aaattctctt ttatgacatg  1560
tccctttata ttgaatgctg tcacaaagaa tttgggatta tattatgaca atagaattcg  1620
catgtacagt gaacgaagaa tcactgttct ctacagctta gttcaaggac agcagttgaa  1680
tccatatttg agactcaaag ttagacgtga ccatatcata gatgatgcac ttgtccggct  1740
agagatgatc gctatggaaa atcctgcaga cttgaagaag cagttgtatg tggaatttga  1800
aggagaacaa ggagttgatg agggaggtgt ttccaaagaa ttttttcagc tggttgtgga  1860
ggaaatcttc aatccagata ttggtatgtt cacatacgat gaatctacaa aattgttttg  1920
gtttaatcca tcttctttg aaactgaggg tcagtttact ctgattggca tagtactggg  1980
tctggctatt tacaataact gtatactgga tgtacatttt cccatggttg tctacaggaa  2040
gctaatgggg aaaaaaggaa cttttcgtga cttgggagac tctcacccag ttctatatca  2100
gagtttaaaa gatttattgg agtatgaagg gaatgtggaa gatgacatga tgatcacttt  2160
ccagatatca cagacagatc tttttggtaa cccaatgatg tatgatctaa aggaaaatgg  2220
tgataaaatt ccaattacaa atgaaaacag gaaggaattt gtcaatcttt attctgacta  2280
cattctcaat aaatcagtag aaaaacagtt caaggctttt cggagaggtt ttcatatggt  2340
gaccaatgaa tctcccttaa agtacttatt cagaccagaa gaaattgaat tgcttatatg  2400
tggaagccgg aatctagatt tccaagcact agaagaaact acagaatatg acggtggcta  2460
taccagggac tctgttctga ttagggagtt ctgggaaatc gttcattcat ttacagatga  2520
acagaaaaga ctcttcttgc agtttacaac gggcacagac agagcacctg tgggaggact  2580
aggaaaatta aagatgatta tagccaaaaa tggcccagac acagaaaggt tacctacatc  2640
tcatacttgc tttaatgtgc ttttacttcc ggaatactca agcaaagaaa aacttaaaga  2700
gagattgttg aaggccatca cgtatgccaa aggatttggc atgctgtaaa acaaaacaaa  2760
acaaaat                                                            2767

SEQ ID NO: 13           moltype = DNA  length = 5276
FEATURE                 Location/Qualifiers
source                  1..5276
                        mol_type = genomic DNA
                        organism = Homo sapiens
SEQUENCE: 13
agccagtcct cccgtcttgc gccgcggccg cgagatccgt gtgtctccca agatggtggc  60
gctgggctcg gggtgactac aggagacgac ggggcctttt cccttcgcca ggacccgaca  120
caccaggctt cgctcgctcg cgcacccctc cgccgcgtag ccatccgcca gcgcgggcgc  180
ccgccatccg ccgcctactt acgcttcacc tctgccgacc cggcgcgctc ggctgcgggc  240
ggcggcgcct ccttcggctc ctcctcggaa tagctcgcgg cctgtagccc ctggcaggag  300
ggcccctcag ccccccggtg tggacaggca gcggcggctg gcgacgaacg ccgggatttc  360
ggcggccccg gcgctccctt tcccggcctc gttttccgga taaggaagcg cgggtcccgc  420
atgagccccg gcggtggcgg cagcgaaaga gaacgaggcg gtggcgggcg gaggcggcgg  480
gcgagggcga ctacgaccag tgaggcggcc gccgcagccc aggcgcgggg gcgacgacag  540
gttaaaaatc tgtaagagcc tgattttaga attcaccagc tcctcagaag tttggcgaaa  600
tatgagttat taagcctacg ctcagatcaa ggtagcagct agactggtgt gacaacctgt  660
ttttaatcag tgactcaaag ctgtgatcac cctgatgtca ccgaatggcc acagcttgta  720
aaagagagtt acagtggagg taaaaggagt ggcttgcagg atggagaagc tgcaccagtg  780
ttattggaaa tcaggagaac ctcagtctga cgacattgaa gctagccgaa tgaagcgagc  840
agctgcaaag catctaatag aacgctacta ccaccagtta actgagggct gtggaaatga  900
agcctgcacg aatgagtttt gtgcttcctg tccaactttt cttcgtatgg ataataatgc  960
agcagctatt aaagccctcg agctttataa gattaatgca aaactctgtg atcctcatcc  1020
ctccaagaaa ggagcaagct cagcttacct tgagaactcg aaaggtgccc ccaacaactc  1080
```

-continued

```
ctgctctgag ataaaaatga acaagaaagg cgctagaatt gattttaaag atgtgactta  1140
cttaacagaa gagaaggtat atgaaattct tgaattatgt agagaaagag aggattattc  1200
ccctttaatc cgtgttattg gaagagtttt ttctagtgct gaggcattgg tacagagctt  1260
ccggaaagtt aaacaacaca ccaaggaaga actgaaatct cttcaagcaa aagatgaaga  1320
caaagatgaa gatgaaaagg aaaaagctgc atgttctgct gctgctatgg aagaagactc  1380
agaagcatct tcctcaagga taggtgatag ctcacaggga gacaacaatt tgcaaaaatt  1440
aggccctgat gatgtgtctg tggatattga tgccattaga agggtctaca ccagattgct  1500
ctctaatgaa aaaattgaaa ctgcctttct caatgcactt gtatatttgt cacctaacgt  1560
ggaatgtgac ttgacgtatc acaatgtata ctctcgagat cctaattatc tgaatttgtt  1620
cattatcgta atggagaata gaaatctcca cagtcctgaa tatctggaaa tggctttgcc  1680
attattttgc aaagcgatga gcaagctacc ccttgcagcc caaggaaaac tgatcagact  1740
gtggtctaaa tacaatgcag accagattcg gagaatgatg gagacatttc agcaacttat  1800
tacttataaa gtcataagca atgaatttaa cagtcgaaat ctagtgaatg atgatgatgc  1860
cattgttgct gcttcgaagt gcttgaaaat ggtttactat gcaaatgtag tgggagggga  1920
agtggacaca aatcacaatg aagaagatga tgaagagccc atccctgagt ccagcgagct  1980
gacacttcag gaacttttgg gagaagaaag aagaaacaag aaaggtcctc gagtggaccc  2040
cctggaaact gaacttggtg ttaaaaccct ggattgtcga aaaccactta tcccttttga  2100
agagtttatt aatgaaccac tgaatgaggt tctagaaatg gataaagatt atactttttt  2160
caaagtagaa acagagaaca aattctcttt tatgacatgt ccctttatat tgaatgctgt  2220
cacaaagaat ttgggattat attatgacaa tagaattcgc atgtacagtg aacgaagaat  2280
cactgttctc tacagcttag ttcaaggaca gcagttgaat ccatatttga gactcaaagt  2340
tagacgtgac catatcatag atgatgcact tgtccggcta gagatgatcg ctatggaaaa  2400
tcctgcagac ttgaagaagc agttgtatgt ggaatttgaa ggagaacaag gagttgatga  2460
gggaggtgtt tccaaagaat tttttcagct ggttgtggag gaaatcttca atccagatat  2520
tggtatgttc acatacgatg aatctacaaa attgttttgg tttaatccat cttcttttga  2580
aactgagggt cagtttactc tgattggcat agtactgggt ctggctattt acaataactg  2640
tatactggat gtacattttc ccatggttgt ctacaggaag ctaatgggga aaaaaggaac  2700
ttttcgtgac ttgggagact ctcacccagt tctatatcag agtttaaaag atttattgga  2760
gtatgaaggg aatgtggaag atgacatgat gatcactttc cagatatcac agacagatct  2820
tttggtaac ccaatgatgt atgatctaaa ggaaaatggt gataaaattc caattacaaa  2880
tgaaaacagg aaggaatttg tcaatcttta ttctgactac attctcaata aatcagtaga  2940
aaaacagttc aaggcttttc ggagaggttt tcatatggtg accaatgaat ctcccttaaa  3000
gtacttattc agaccagaag aaattgaatt gcttatatgt ggaagccgga atctagattt  3060
ccaagcacta gaagaaacta cagaatatga cggtggctat accagggact ctgttctgat  3120
tagggagttc tgggaaatcg ttcattcatt tacagatgaa cagaaaagac tcttcttgca  3180
gtttacaacg ggcacagaca gagcacctgt gggaggacta ggaaaattaa agatgattat  3240
agccaaaaat ggcccagaca cagaaaggtt acctacatct catacttgct ttaatgtgct  3300
tttacttccg gaatactcaa gcaaagaaaa acttaaagag agattgttga aggccatcac  3360
gtatgccaaa ggatttggca tgctgtaaaa caaaacaaaa caaaataaaa caaaaaaaag  3420
gaaggaaaaa aaaagaaaaa atttaaaaaa ttttaaaaat ataacgaggg ataaattttt  3480
ggtggtgata gtgtcccagt acaaaaaggc tgtaagatag tcaaccacag tagtcaccta  3540
tgtctgtgcc tcccttcttt attggggaca tgtgggctgg aacagcagat ttcagctaca  3600
tatatgaaca aatcctttat tattattata attatttttt tgcgtgaaag tgttacatat  3660
tctttcactt gtatgtacag agaggttttt ctgaatattt attttaaggg ttaaatcact  3720
tttgcttgtg tttattactg cttgaggttg agccttttga gtatttaaaa aatatatacc  3780
aacagaacta ctctcccaag gaaaatattg ccaccatttg tagaccacgt aaccttcaag  3840
tatgtgctac tttttgtcc ctgtatctaa ctcaaatcag gaactgtatt tttttaatg  3900
atttgctttt gaaacttgaa gtcttgaaaa cagtgtgatg caattactgc tgttctagcc  3960
cccaaagagt tttctgtgca aaatcttgag aatcaatcaa taaagaaaga tggaaggaag  4020
ggagaaattg gaatgtttta actgcagccc tcagaacttt agtaacagca caacaaatta  4080
aaaacaaaaa caactcatgc cacagtatgt cgtcttcatg tgtcttgcaa tgaactgttt  4140
cagtagccaa tcctctttct tagtatatga aaggacaggg atttttgttc ttgttgttct  4200
cgttgttgtt ttaagtttac tggggaaagt gcatttggcc aaatgaaatg gtagtcaagc  4260
ctattgcaac aaagttagga agtttgttgt ttgtttatta taaacaaaaa gcatgtgaaa  4320
gtgcacttaa gatagagttt ttattaatta cttacttatt acctagattt taaatagaca  4380
atccaaagtc tccccttcgt gttgccatca tcttgttgaa tcagccattt tatcgaggca  4440
cgtgatcagt gttgcaacat aatgaaaaag atggctactg tgccttgtgt tacttaatca  4500
tacagtaagc tgacctggaa atgaatgaaa ctattactcc taagaattac attgtatagc  4560
cccacagatt aaatttaatt aattaattca aaacatgtta aacgttactt tcatgtacta  4620
tggaaaagta caagtaggtt tacattactg atttccagaa gtaagtagtt tcccctttcc  4680
tagtcttctg tgtatgtgat gttgttaatt tcttttattg cattataaaa taaaaggatt  4740
atgtattttt aactaaggtg agacattgat atatcctttt gctacaagct atagctaatg  4800
tgctgagctt gtgccttggt gattgattga ttgattgact gattgtttta actgattact  4860
gtagatcaac ctgatgattt gtttgtttga aattggcagg aaaaatgcag ctttcaaatc  4920
attgggggga gaaaaaggat gtctttcagg attattttaa ttaatttttt tcataattga  4980
gacagaactg tttgttatgt accataatgc taaataaaac tgtggcactt ttcaccataa  5040
tttaatttag tggaaaaaga agacaatgct ttccatattg tgataaggta acatggggtt  5100
tttctgggcc agcctttaga acactgttag ggtacatacg ctaccttgat gaaagggacc  5160
ttcgtgcaac tgtagtcatc ttaaaggctt ctcatccact gtgcttctta atgtgtaatt  5220
aaagtgagga gaaattaaat actctgaggg cgttttatat aataaattcg tgaaga      5276

SEQ ID NO: 14          moltype = AA  length = 875
FEATURE                Location/Qualifiers
source                 1..875
                       mol_type = protein
                       organism = Homo sapiens
SEQUENCE: 14
MEKLHQCYWK SGEPQSDDIE ASRMKRAAAK HLIERYYHQL TEGCGNEACT NEFCASCPTF  60
LRMDNNAAAI KALELYKINA KLCDPHPSKK GASSAYLENS KGAPNNSCSE IKMNKKGARI  120
```

-continued

```
DFKDVTYLTE EKVYEILELC REREDYSPLI RVIGRVFSSA EALVQSFRKV KQHTKEELKS  180
LQAKDEDKDE DEKEKAACSA AAMEEDSEAS SSRIGDSSQG DNNLQKLGPD DVSVDIDAIR  240
RVYTRLLSNE KIETAFLNAL VYLSPNVECD LTYHNVYSRD PNYLNLFIIV MENRNLHSPE  300
YLEMALPLFC KAMSKLPLAA QGKLIRLWSK YNADQIRRMM ETFQQLITYK VISNEFNSRN  360
LVNDDDAIVA ASKCLKMVYY ANVVGGEVDT NHNEEDDEEP IPESSELTLQ ELLGEERRNK  420
KGPRVDPLET ELGVKTLDCR KPLIPFEEFI NEPLNEVLEM DKDYTFFKVE TENKFSFMTC  480
PFILNAVTKN LGLYYDNRIR MYSERRITVL YSLVQGQQLN PYLRLKVRRD HIIDDALVRL  540
EMIAMENPAD LKKQLYVEFE GEQGVDEGGV SKEFFQLVVE EIFNPDIGMF TYDESTKLFW  600
FNPSSFETEG QFTLIGIVLG LAIYNNCILD VHFPMVVYRK LMGKKGTFRD LGDSHPVLYQ  660
SLKDLLEYEG NVEDDMMITF QISQTDLFGN PMMYDLKENG DKIPITNENR KEFVNLYSDY  720
ILNKSVEKQF KAFRRGFHMV TNESPLKYLF RPEEIELLIC GSRNLDFQAL EETTEYDGGY  780
TRDSVLIREF WEIVHSFTDE QKRLFLQFTT GTDRAPVGGL GKLKMIIAKN GPDTERLPTS  840
HTCFNVLLLP EYSSKEKLKE RLLKAITYAK GFGML                            875

SEQ ID NO: 15          moltype = DNA  length = 2970
FEATURE                Location/Qualifiers
source                 1..2970
                       mol_type = genomic DNA
                       organism = Homo sapiens
SEQUENCE: 15
tttttccgga taaggaagcg cgggtcccgc atgagccccg gcggtggcgg cagcgaaaga  60
gaacgaggcg gtggcgggcg gaggcggcgg gcgagggcga ctacgaccag tgaggcggcc  120
gccgcagccc aggcgcgggg gcgacgacag gttaaaaatc tgtaagagcc tgattttaga  180
attcaccagc tcctcagaag tttggcgaaa tatgagttat taagcctacg ctcagatcaa  240
ggtagcagct agactggtgt gacaacctgt ttttaatcag tgactcaaag ctgtgatcac  300
cctgatgtca ccgaatggcc acagcttgta aaagatcagg agaacctcag tctgacgaca  360
ttgaagctag ccgaatgaag cgagcagctg caaagcatct aatagaacgc tactaccacc  420
agttaactga gggctgtgga aatgaagcct gcacgaatga gttttgtgct tcctgtccaa  480
cttttcttcg tatggataat aatgcagcag ctattaaagc cctcgagctt tataagatta  540
atgcaaaact ctgtgatcct catccctcca agaaaggagc aagctcagct taccttgaga  600
actcgaaagg tgcccccaac aactcctgct ctgagataaa aatgaacaag aaaggcgcta  660
gaattgattt taaagatgtg acttacttaa cagaagagaa ggtatatgaa attcttgaat  720
tatgtagaga aagagaggat tattcccctt taatccgtgt tattggaaga gtttttttcta  780
gtgctgaggc attggtacag agcttccgga aagttaaaca acacaccaag gaagaactga  840
aatctcttca agcaaaagat gaagacaaag atgaagatga aaaggaaaaa gctgcatgtt  900
ctgctgctgc tatggaagaa gactcagagg catcttcctc aaggataggt gatagctcac  960
agggagacaa caatttgcaa aaattaggcc ctgatgatgt gtctgtggat attgatgcca  1020
ttagaagggt ctacaccaga ttgctctcta atgaaaaaat tgaaactgcc tttctcaatg  1080
cacttgtata tttgtcacct aacgtggaat gtgacttgac gtatcacaat gtatactctc  1140
gagatcctaa ttatctgaat ttgttcatta tcgtaatgga gaatagaaat ctccacagtc  1200
ctgaatatct ggaaatggct ttgccattat tttgcaaagc gatgagcaag ctaccccttg  1260
cagcccaagg aaaactgatc agactgtggt ctaaatacaa tgcagaccag attcggagaa  1320
tgatggagac atttcagcaa cttattactt ataaagtcat aagcaatgaa tttaacagtc  1380
gaaatctagt gaatgatgat gatgccattg ttgctgcttc gaagtgcttg aaaatggttt  1440
actatgcaaa tgtagtggga ggggaagtgg acacaaatca caatgaagaa gatgatgaag  1500
agcccatccc tgagtccagc gagctgacac ttcaggaact tttgggagaa gaaagaagaa  1560
acaagaaagg tcctcgagtg gacccccctgg aaactgaact tggtgttaaa accctggatt  1620
gtcgaaaacc acttatccct tttgaagagt ttattaatga accactgaat gaggttctag  1680
aaatggataa agattatact tttttcaaag tagaaacaga gaacaaattc tcttttatga  1740
catgtccctt tatattgaat gctgtcacaa agaatttggg attatattat gacaatagaa  1800
ttcgcatgta cagtgaacga agaatcactg ttctctacag cttagttcaa ggacagcagt  1860
tgaatccata tttgagactc aaagttagac gtgaccatat catagatgat gcacttgtcc  1920
ggctagagat gatcgctatg gaaaatcctg cagacttgaa gaagcagttg tatgtggaat  1980
ttgaaggaga acaaggagtt gatgagggag gtgtttccaa agaattttttt cagctggttg  2040
tggaggaaat cttcaatcca gatattggta tgttcacata cgatgaatct acaaaattgt  2100
tttggtttaa tccatcttct tttgaaactg agggtcagtt tactctgatt ggcatagtac  2160
tgggtctggc tatttacaat aactgtatac tggatgtaca ttttcccatg gttgtctaca  2220
ggaagctaat ggggaaaaaa ggaacttttc gtgacttggg agactctcac ccagttctat  2280
atcagagttt aaaagattta ttggagtatg aagggaatgt ggaagatgac atgatgatca  2340
ctttccagat atcacagaca gatctttttg gtaacccaat gatgtatgat ctaaaggaaa  2400
atggtgataa aattccaatt acaaatgaaa acaggaagga atttgtcaat ctttattctg  2460
actacattct caataaatca gtagaaaaac agttcaaggc ttttcggaga ggttttcata  2520
tggtgaccaa tgaatctccc ttaaagtact tattcagacc agaagaaatt gaattgctta  2580
tatgtggaag ccggaatcta gatttccaag cactagaaga aactacagaa tatgacggtg  2640
gctataccag ggactctgtt ctgattaggg agttctggga aatcgttcat tcatttacag  2700
atgaacagaa aagactcttc ttgcagttta caacgggcac agacagagca cctgtgggag  2760
gactaggaaa attaaagatg attatagcca aaaatggccc agacacagaa aggttaccta  2820
catctcatac ttgctttaat gtgcttttac ttccggaata ctcaagcaaa gaaaaactta  2880
aagagagatt gttgaaggcc atcacgtatg ccaaaggatt tggcatgctg taaaacaaaa  2940
caaaacaaaa taaaacaaaa aaaaggaagg                                  2970
```

MODIFIED UBE3A GENE FOR A GENE THERAPY APPROACH FOR ANGELMAN SYNDROME

CROSS-REFERENCE TO RELATED APPLICATIONS

This application is a continuation of and claims priority to continuation of and claims priority to currently pending U.S. Nonprovisional application Ser. No. 15/805,442, filed Nov. 7, 2017 which claims priority to International Patent Application No. PCT/US2016/031468, filed May 9, 2016 which claims priority to U.S. Provisional Application No. 62/158,269, entitled "Modified UBE3A Gene for a Gene Therapy Approach for Angelman Syndrome", filed May 7, 2015, each of which is incorporated herein by reference.

FIELD OF INVENTION

This invention relates to treatment of Angelman syndrome. More specifically, the present invention provides therapeutic methods and compositions for treating Angelman syndrome.

BACKGROUND OF INVENTION

Angelman syndrome (AS) is a genetic disorder affecting neurons, estimated to affect about one in every 15,000 births (Clayton-Smith, Clinical research on Angelman syndrome in the United Kingdom: observations on 82 affected individuals. Am J Med Genet. 1993 Apr. 1; 46 (1): 12-5), though the actual number of diagnosed AS cases is lower likely due to misdiagnosis.

Angelman syndrome is a continuum of impairment, which presents with delayed and reduced intellectual and developmental advancement, in particular with respect to language and motor skills. In particular, AS is defined by little or no verbal communication, with some non-verbal communication, ataxia, and disposition that includes frequent laughing and smiling and excitable movement.

More advanced cases result in severe mental retardation, seizures that may be difficult to control that typically begin before or by three years of age, frequent laughter (Nicholls, New insights reveal complex mechanisms involved in genomic imprinting. Am J Hum Genet. 1994 May; 54 (5): 733-40), miroencephaly, and abnormal EEG. In severe cases, patients may not develop language or may only have use of 5-10 words. Movement is commonly jerky, and walking commonly is associated with hand flapping and a stiff-gait. The patients are commonly epileptic, especially earlier in life, and suffer from sleep apnea, commonly only sleeping for 5 hours at a time. They are social and desire human contact. In some cases, skin and eyes may have little or no pigment, possess sucking and swallowing problems, sensitivity to heat, and a fixation to water bodies. Studies in UBE3A-deficient mice show disturbances in long-term synaptic plasticity. There are currently no cures for Angelman syndrome, and treatment is palliative. For example, anticonvulsant medication is used to reduce epileptic seizures, and speech and physical therapy are used to improve language and motor skills.

The gene UBE3A is responsible for AS and it is unique in that it is one of a small family of human imprinted genes. UBE3A, found on chromosome 15, encodes for the homologous to E6AP C terminus (HECT) protein (E6-associated protein (E6AP) (Kishino, et al., UBE3A/E6-AP mutations cause Angelman syndrome. Nat Gen. 1997 Jan. 15.15 (1):

70-3). UBE3A undergoes spatially-defined maternal imprinting in the brain; thus, the paternal copy is silenced via DNA methylation (Albrecht, et al., Imprinted expression of the murine Angelman syndrome gene, Ube3a, in hippocampal and Purkinje neurons. Nat Genet. 1997 September; 17 (1): 75-8). As such, only the maternal copy is active, the paternal chromosome having little or no effect on the proteasome of the neurons in that region of the brain. Inactivation, translocation, or deletion of portions of chromosome 15 therefore results in uncompensated loss of function. Some studies suggest improper E6-AP protein levels alter neurite contact in Angelman syndrome patients (Tonazzini, et al., Impaired neurite contract guidance in ubiquitin ligase E3a (Ube3a)-deficient hippocampal neurons on nanostructured substrates. Adv Healthc Mater. 2016 April; 5 (7): 850-62).

The majority of Angelman's syndrome cases (70%) occur through a de novo deletion of around 4 Mb from 15q11-q13 of the maternal chromosome which incorporates the UBE3A gene (Kaplan, et al., Clinical heterogeneity associated with deletions in the long arm of chromosome 15: report of 3 new cases and their possible significance. Am J Med Genet. 1987 September; 28 (1): 45-53), but it can also occur as a result of abnormal methylation of the maternal copy, preventing its expression (Buiting, et al., Inherited microdeletions in the Angelman and Prader-Willi syndromes define an imprinting centre on human chromosome 15. Nat Genet. 1995 April; 9 (4): 395-400; Gabriel, et al., A transgene insertion creating a heritable chromosome deletion mouse model of Prader-Willi and Angelman syndrome. Proc Natl Acad Sci U.S.A. 1999 August; 96 (16): 9258-63) or uniparental disomy in which two copies of the paternal gene are inherited (Knoll, et al., Angelman and Prader-Willi syndromes share a common chromosome 15 deletion but differ in parental origin of the deletion. Am J Med Genet. 1989 Fed; 32 (2): 285-90; Malcolm, et al., Uniparental paternal disomy in Angelman's syndrome. Lancet. 1991 Mar. 23; 337 (8743): 694-7). The remaining AS cases arise through various UBE3A mutations of the maternal chromosome or they are diagnosed without a genetic cause (12-15UBE3A codes for the E6-associated protein (E6-AP) ubiquitin ligase. E6-AP is an E3 ubiquitin ligase, therefore it exhibits specificity for its protein targets, which include the tumor suppressor molecule p53 (Huibregtse, et al., A cellular protein mediates association of p53 with the E6 oncoprotein of human papillomavirus types 16 or18. EMBO J. 1991 December; 10 (13): 4129-35), a human homologue to the yeast DNA repair protein Rad23 (Kumar, et al., Identification of HHR23A as a substrate for E6-associated protein-mediated ubiquitination. J Biol Chem. 1999 Jun. 25; 274 (26): 18785-92), E6-AP itself, and Arc, the most recently identified target (Nuber, et al., The ubiquitin-protein ligase E6-associated protein (E6-AP) serves as its own substrate. Eur J Biochem. 1998 Jun. 15; 254 (3): 643-9; Greer, et al., The Angelman Syndrome protein Ube3A regulates synapse Development by ubiquitinating arc. Cell. 2010 Mar. 5; 140 (5): 704-16).

Mild cases are likely due to a mutation in the UBE3A gene at chromosome 15q11-13, which encodes for E6-AP ubiquitin ligase protein of the ubiquitin pathway, and more severe cases resulting from larger deletions of chromosome 15. Commonly, the loss of the UBE3A gene in the hippocampus and cerebellum result in Angelman syndrome, though single loss-of-function mutations can also result in the disorder.

The anatomy of the mouse and human AS brain shows no major alterations compared to the normal brain, indicating the cognitive deficits may be biochemical in nature as opposed to developmental (Jiang, et al., Mutation of the Angelman ubiquitin ligase in mice causes increased cytoplasmic p53 and deficits of contextual learning and long-term potentiation. Neuron. 1998 October; 21 (4): 799-811; Davies, et al., Imprinted gene expression in the brain. Neurosci Biobehav Rev. 2005 May; 29 (3): 421-430). An Angelman syndrome mouse model possessing a disruption of the maternal UBE3A gene through a null mutation of exon 2 (Jiang, et al., Mutation of the Angelman ubiquitin ligase in mice causes increased cytoplasmic p53 and deficits of contextual learning and long-term potentiation. Neuron. 1998 October; 21 (4): 799-811) was used. This model has been incredibly beneficial to the field of AS research due to its ability in recapitulating the major phenotypes characteristic of AS patients. For example, the AS mouse has inducible seizures, poor motor coordination, hippocampal-dependent learning deficits, and defects in hippocampal LTP. Cognitive deficits in the AS mouse model were previously shown to be associated with abnormalities in the phosphorylation state of calcium/calmodulin-dependent protein kinase II (CaMKII) (Weeber, et al., Derangements of hippocampal calcium/calmodulin-dependent protein kinase II in a mouse model for Angelman mental retardation syndrome. J Neurosci. 2003 April; 23 (7): 2634-44). There was a significant increase in phosphorylation at both the activating $Thr^{286}$ site as well as the inhibitory $Thr^{305}$ site of αCaMKII without any changes in total enzyme level, resulting in an overall decrease in its activity. There was also a reduction in the total amount of CaMKII at the postsynaptic density, indicating a reduction in the amount of active CaMKII. Crossing a mutant mouse model having a point mutation at the $Thr^{305}$ site preventing phosphorylation with the AS mouse rescued the AS phenotype, i.e. seizure activity, motor coordination, hippocampal-dependent learning, and LTP were restored similar to wildtype levels. Thus, postnatal expression of αCaMKII suggests that the major phenotypes of the AS mouse model are due to postnatal biochemical alterations as opposed to a global developmental defect (Bayer, et al., Developmental expression of the CaM kinase II isoforms: ubiquitous γ- and δ-CaM kinase II are the early isoforms and most abundant in the developing nervous system. Brain Res Mol Brain Res. 1999 Jun. 18; 70 (1): 147-54).

Deficiencies in Ube3a are also linked in Huntington's disease (Maheshwari, et al., Deficiency of Ube3a in Huntington's disease mice brain increases aggregate load and accelerates disease pathology. Hum Mol Genet. 2014 Dec. 1; 23 (23): 6235-45).

Matentzoglu noted E6-AP possesses non-E3 activity related to hormone signaling (Matentzoglu, EP 2,724,721 A1). As such, administration of steroids, such as androgens, estrogens, and glucocorticoids, was used for treating various E6-AP disorders, including Angelman syndrome, autism, epilepsy, Prader-Willi syndrome, cervical cancer, fragile X syndrome, and Ret syndrome. Philpot suggested using a topoisomerase inhibitor to demethylate silenced genes thereby correcting for deficiencies in Ube3A (Philpot, et al., P. G. Pub. US 2013/0317018 A1). However, work in the field, and proposed therapeutics, do not address the underlying disorder, as in the use of steroids, or may result in other disorders, such as autism, where demethylation compounds are used. Accordingly, what is needed is a therapeutic that addresses the underlying cause of UBE3A deficiency disorders, in a safe, efficacious manner.

SUMMARY OF THE INVENTION

While most human disorders characterized by severe mental retardation involve abnormalities in brain structure, no gross anatomical changes are associated with AS. A, Ube3a protein has been generated containing an appended to a cellular secretion sequence that allows the secretion of Ube3a from cells and cellular uptake sequence that provides uptake by neighboring neuronal cells. This provides a functional E6-AP protein into the neurons thereby rescuing from disease pathology.

As such, a UBE3A vector was formed using a transcription initiation sequence, and a UBE construct disposed downstream of the transcription initiation sequence. The UBE construct is formed of a UBE3A sequence, a secretion sequence, and a cell uptake sequence. Nonlimiting examples of the UBE3A sequence are SEQ ID No. 1, SEQ ID No. 6, SEQ ID No. 12, SEQ ID No. 13, a cDNA of SEQ ID No. 7, or a homologous sequence. Variations of the DNA sequence include conservative mutations in the DNA triplet code, as seen in the Table. In specific variations, the UBE3A sequence is *Mus musculus* UBE3A U82122.1, *Homo sapiens* UBE3A variant 1, and variant 2. Nonlimiting examples of the secretion sequence are SEQ ID No. 2, SEQ ID No. 8, SEQ ID No. 9, SEQ ID No. 10, a cDNA of SEQ ID No. 3, or a homologous sequence, with variations of the DNA sequence that include the aforementioned conservative mutations. Nonlimiting examples of the cell uptake sequence are SEQ ID No. 4, a cDNA of SEQ ID No. 11, a cDNA of SEQ ID No. 5, or a homologous sequence. Variations of the DNA sequence include the aforementioned conservative mutations. In specific variations of the invention, the secretion sequence is disposed upstream of the UBE3A sequence, and more specifically is optionally disposed upstream of the UBE3A sequence and downstream of the secretion sequence.

The Table shows the redundant triplet code and corresponding encoded amino acids, based on functional group category.

| Nonpolar, aliphatic | | | | Polar, uncharged | | | |
|---|---|---|---|---|---|---|---|
| | Gly | G | GGT | | Ser | S | AGT |
| | | | GGC | | | | AGC |
| | | | GGA | | | | TCT |
| | | | GGG | | | | TCC |
| | | | | | | | TCA |
| | | | | | | | TCG |
| | Ala | A | GCT | | Thr | T | ACT |
| | | | GCC | | | | ACC |
| | | | GCA | | | | ACA |
| | | | GCG | | | | ACG |
| | Val | V | GTT | | Cys | C | TGT |
| | | | GTC | | | | TGC |
| | | | GTA | | | | |
| | | | GTG | | | | |
| | Leu | L | TTA | | Pro | P | CCT |
| | | | TTG | | | | CCC |
| | | | CTT | | | | CCA |
| | | | CTC | | | | CCG |
| | | | CTA | | | | |
| | | | CTG | | | | |
| | Met | M | ATG | | Asn | N | AAT |
| | | | | | | | AAC |
| | Ile | I | ATT | | Gln | Q | CAA |
| | | | ATC | | | | CAG |
| | | | ATA | | | | |
| **Aromatic** | | | | **Positive charge** | | | |
| | Phe | F | TTT | | Lys | K | AAA |
| | | | TTC | | | | AAG |
| | Tyr | Y | TAT | | His | H | CAT |
| | | | TAC | | | | CAC |

-continued

| | | | | | | |
|---|---|---|---|---|---|---|
| | Trp | W | TGG | Arg | R | CGT CGC CGA CGG AGA AGG |
| Negative charge | | | OTHER | | | |
| | Asp | D | GAT GAC | stop | | TTA TAG TGA |
| | Glu | E | GAA GAG | | | |

In some variations of the invention, the transcription initiation sequence is a cytomegalovirus chicken-beta actin hybrid promoter, or human ubiquitin c promoter. The invention optionally includes an enhancer sequence. A nonlimiting example of the enhancer sequence is a cytomegalovirus immediate-early enhancer sequence disposed upstream of the transcription initiation sequence. The vector optionally also includes a woodchuck hepatitis post-transcriptional regulatory element.

In variations, the vector is inserted into a plasmid, such as a recombinant adeno-associated virus serotype 2-based plasmid. In specific variations, the recombinant adeno-associated virus serotype 2-based plasmid lacks DNA integration elements. A nonlimiting example of the recombinant adeno-associated virus serotype 2-based plasmid is a pTR plasmid.

A method of synthesizing a UBE3A vector is also provided. A UBE3A construct was inserted into a backbone plasmid having a transcription initiation sequence, where the UBE3A construct is formed of a UBE3A sequence, a secretion sequence, and a cell uptake sequence. In some variations, the UBE3A construct was inserted downstream of the transcription initiation sequence. Nonlimiting examples of the UBE3A sequence are SEQ ID No. 1, SEQ ID No. 6, SEQ ID No. 12, SEQ ID No. 13, a cDNA of SEQ ID No. 7, or a homologous sequence. Variations of the DNA sequence include conservative mutations in the DNA triplet code, as seen in the Table. Nonlimiting examples of the secretion sequence are SEQ ID No. 2, SEQ ID No. 8, SEQ ID No. 9, SEQ ID No. 10, a cDNA of SEQ ID No. 3, or a homologous sequence, with variations of the DNA sequence that include the aforementioned conservative mutations. Nonlimiting examples of the cell uptake sequence are SEQ ID No. 4, a cDNA of SEQ ID No. 11, a cDNA of SEQ ID No. 5, or a homologous sequence. Variations of the DNA sequence include the aforementioned conservative mutations. In specific variations of the invention, the secretion sequence is disposed upstream of the UBE3A sequence, and more specifically is optionally disposed upstream of the UBE3A sequence and downstream of the secretion sequence. For example, Ube3a gene was cloned and fused in frame to the 3' DNA sequence (N-terminus with two other peptide sequences), signal peptide and HIV TAT sequences, which were cloned into a recombinant adeno-associated viral vector for expression of the secreted E6-AP protein in the brain and spinal cord of AS patients. The UBE construct is optionally inserted by cleaving the backbone plasmid with at least one endonuclease, and the UBE3A construct ligated to the cleaved ends of the backbone plasmid.

The vector was then optionally inserted into an amplification host, possessing an antibiotic resistance gene, and subjected to an antibiotic selection corresponding to the antibiotic resistance gene. The amplification host was then expanded in a medium containing the antibiotic selection and the expanded amplification host collected. The vector was then isolated from the amplification host. In specific variations of the invention, the antibiotic resistance gene is an ampicillin resistance gene, with the corresponding antibiotic selection, ampicillin.

A method of treating a UBE3A deficiency disease, such as Angelman syndrome, Prader-Willi syndrome, or Huntington's disease, is also provided. A vector, as described above, was administered to the brain of a patient suffering from the UBE3A deficiency disease to correct the UBE deficiency. The vector was optionally administered by injection. Nonlimiting examples include intrahippocampal or ventricular injection. In specific variations, the vector was injected bilaterally. Optional dosages include about $5.55\times10^{11}$ genomes/g brain mass to about $2.86\times10^{12}$ genomes/g brain mass, or more specifically $5.55\times10^{11}$ to $2.86\times10^{12}$ genomes/g brain mass. Nonlimiting examples of dosages are:

$5.55\times10^{11}$ genomes/g brain mass, $5.75\times10^{11}$ genomes/g brain mass, $5.8\times10^{11}$ genomes/g brain mass, $5.9\times10^{11}$ genomes/g brain mass, $6.0\times10^{11}$ genomes/g brain mass, $6.1\times10^{11}$ genomes/g brain mass, $6.2\times10^{11}$ genomes/g brain mass, $6.3\times10^{11}$ genomes/g brain mass, $6.4\times10^{11}$ genomes/g brain mass, $6.5\times10^{11}$ genomes/g brain mass, $6.6.\times10^{11}$ genomes/g brain mass, $6.7\times10^{11}$ genomes/g brain mass, $6.8\times10^{11}$ genomes/g brain mass, $6.9.\times10^{11}$ genomes/g brain mass, $7.0\times10^{11}$ genomes/g brain mass, $7.1\times10^{11}$ genomes/g brain mass, $7.2\times10^{11}$ genomes/g brain mass, $7.3\times10^{11}$ genomes/g brain mass, $7.4\times10^{11}$ genomes/g brain mass, $7.5\times10^{11}$ genomes/g brain mass, $7.6\times10^{11}$ genomes/g brain mass, $7.7\times10^{11}$ genomes/g brain mass, $7.8\times10^{11}$ genomes/g brain mass, $7.9\times10^{11}$ genomes/g brain mass, $8.0\times10^{11}$ genomes/g brain mass, $8.1\times10^{11}$ genomes/g brain mass, $8.2\times10^{11}$ genomes/g brain mass, $8.3\times10^{11}$ genomes/g brain mass, $8.4\times10^{11}$ genomes/g brain mass, $8.5\times10^{11}$ genomes/g brain mass, $8.6\times10^{11}$ genomes/g brain mass, $8.7\times10^{11}$ genomes/g brain mass, $8.8\times10^{11}$ genomes/g brain mass, $8.9\times10^{11}$ genomes/g brain mass, $9.0\times10^{11}$ genomes/g brain mass, $9.1\times10^{11}$ genomes/g brain mass, $9.2\times10^{11}$ genomes/g brain mass, $9.3\times10^{11}$ genomes/g brain mass, $9.4\times10^{11}$ genomes/g brain mass, $9.5\times10^{11}$ genomes/g brain mass, $9.6\times10^{11}$ genomes/g brain mass, $9.7\times10^{11}$ genomes/g brain mass, $9.80\times10^{11}$ genomes/g brain mass, $1.0\times10^{12}$ genomes/g brain mass, $1.1\times10^{12}$ genomes/g brain mass, $1.2\times10^{12}$ genomes/g brain mass, $1.3\times10^{12}$ genomes/g brain mass, $1.4\times10^{12}$ genomes/g brain mass, $1.5\times10^{12}$ genomes/g brain mass, $1.6\times10^{12}$ genomes/g brain mass, $1.7\times10^{12}$ genomes/g brain mass, $1.8\times10^{12}$ genomes/g brain mass, $1.9\times10^{12}$ genomes/g brain mass, $2.0\times10^{12}$ genomes/g brain mass, $2.1\times10^{12}$ genomes/g brain mass, $2.2\times10^{12}$ genomes/g brain mass, $2.3\times10^{12}$ genomes/g brain mass, $2.40\times10^{12}$ genomes/g brain mass, $2.5\times10^{12}$ genomes/g brain mass, $2.6\times10^{12}$ genomes/g brain mass, $2.7\times10^{12}$ genomes/g brain mass, $2.75\times10^{12}$ genomes/g brain mass, $2.8\times10^{12}$ genomes/g brain mass, or $2.86\times10^{12}$ genomes/g brain mass.

BRIEF DESCRIPTION OF THE DRAWINGS

For a fuller understanding of the invention, reference should be made to the following detailed description, taken in connection with the accompanying drawings, in which.

For a fuller understanding of the invention, reference should be made to the following detailed description, taken in connection with the accompanying drawings, in which.

DETAILED DESCRIPTION OF THE PREFERRED EMBODIMENT

Figure 1:
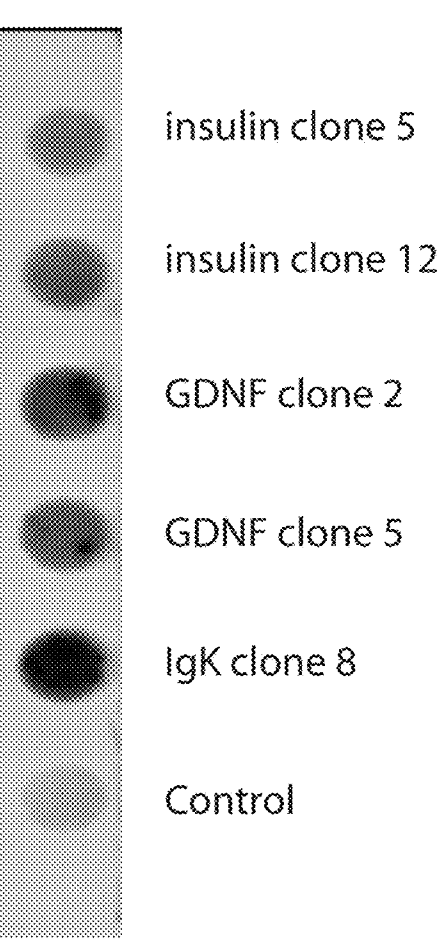
FIG. 1 is a dot blot of anti-GFP on media from HEK293 cells transfected with GFP clones containing signal peptides as indicated.

As used herein, the singular forms “a,” “an” and “the” include plural referents unless the context clearly dictates otherwise. Thus, for example, reference to "a polypeptide" includes a mixture of two or more polypeptides and the like.

As used herein, "about" means approximately or nearly and in the context of a numerical value or range set forth means±15% of the numerical "Administration" or "administering" is used to describe the process in which compounds of the present invention, alone or in combination with other compounds, are delivered to a patient. The composition may be administered in various ways including oral, parenteral (referring to intravenous and intraarterial and other appropriate parenteral routes), intratheceally, intramuscularly, subcutaneously, colonically, rectally, and nasally, among others. Each of these conditions may be readily treated using other administration routes of compounds of the present invention to treat a disease or condition. The dosing of compounds and compositions of the present invention to obtain a therapeutic or prophylactic effect is determined by the circumstances of the patient, as known in the art. The dosing of a patient herein may be accomplished through individual or unit doses of the compounds or compositions herein or by a combined or prepackaged or pre-formulated dose of a compounds or compositions. An average 40 g mouse has a brain weighing 0.416 g, and a 160 g mouse has a brain weighing 1.02 g, a 250 g mouse has a brain weighing 1.802 g. An average human brain weighs 1508 g, which can be used to direct the amount of therapeutic needed or useful to accomplish the treatment described herein.

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, *Remington's Pharmaceutical Sciences* (Martin EW Easton Pennsylvania, Mack Publishing Company, 19th ed.) describes formulations which can be used in connection with the subject invention.

As used herein "animal" means a multicellular, eukaryotic organism classified in the kingdom Animalia or Metazoa. The term includes, but is not limited to, mammals. Non-limiting examples include rodents, mammals, aquatic mammals, domestic animals such as dogs and cats, farm animals such as sheep, pigs, cows and horses, and humans. Wherein the terms "animal" or the plural "animals" are used, it is contemplated that it also applies to any animals.

As used herein, the term "homologous" means a nucleotide sequence possessing at least 80% sequence identity, preferably at least 90% sequence identity, more preferably at least 95% sequence identity, and even more preferably at least 98% sequence identity to the target sequence. Variations in the nucleotide sequence can be conservative mutations in the nucleotide sequence, i.e. mutations in the triplet code that encode for the same amino acid as seen in the Table.

As used herein, the term "therapeutically effective amount" refers to that amount of a therapy (e.g., a therapeutic agent or vector) sufficient to result in the amelioration of Angelman syndrome or other UBE3A-related disorder or one or more symptoms thereof, prevent advancement of Angelman syndrome or other UBE3A-related disorder, or cause regression of Angelman syndrome or other UBE3A-related disorder.

As used herein "patient" is used to describe an animal, preferably a human, to whom treatment is administered, including prophylactic treatment with the compositions of the present invention.

Example 1

To test the efficacy of the secretion signal, GFP was cloned in frame with human insulin, GDNF or IgK signal peptides. The construct was inserted into a pTR plasmid and transfected into HEK293 cells (American Type Culture Collection, Manassas, VA). HEK293 cells were grown at 37° C. 5% $CO_2$ in Dulbecco's Modified Essential Medium (DMEM) with 10% FBS and 1% Pen/Strep and subcultured at 80% confluence.

The vector (2 μg/well in a 6-well plate) was transfected into the cells using PEI transfection method. The cells were subcultured at $0.5\times10^6$ cells per well in a 6-well plate with DMEM medium two days before the transfection. Medium was replaced the night before transfection. Endotoxin-free $dH_2O$ was heated to at around 80° C., and polyethylenimine (Sigma-Aldrich Co. LLC, St. Louis, MO) dissolved. The solution was allowed to cool to around 25° C., and the solution neutralized using sodium hydroxide. AAV4-STUb vector or negative control (medium only) was added to serum-free DMEM at 2 μg to every 200 μL for each well transfected, and 9 μL of 1 μg/μL polyethylenimine added to the mix for each well. The transfection mix was incubated at room temperature for 15 minutes, then added to each well of cells at 210 μL per well and incubated for 48 hours.

Media was collected from each culture well and 2 μL spotted onto a nitrocellulose membrane using a narrow-tipped pipette. After the samples dried, the membrane was blocked applying 5% BSA in TBS-T to the membrane and incubating at room temperature for 30 minutes to 1 hour, followed by incubating the membrane with chicken anti-GFP (5 μg/mL, Abcam PLC, Cambridge, UK; #ab13970) in BSA/TBS-T for 30 min at room temperature. The membrane was washed with TBS-T 3 times, 5 minutes for each wash. The membrane was incubated with anti-chicken HRP conjugate secondary antibody (Southern Biotechnology, Thermo Fisher Scientific, Inc., Waltham, MA; #6100-05, 1/3000) conjugated with HRP for 30 minutes at room temperature, followed by washing the membrane three times with TBS-T, once for 15 minutes, and subsequent washed at 5 minutes each. The membrane was washed with TBS for 5 minutes at room temperature, and incubated with luminescence reagent for 1 minute (Millipore, Merck KGaA, Darmstadt, DE; #WBKLS0100). The membrane was recorded on a GE Amersham Imager 600 (General Electric, Fairfield, CA), shown in FIG. 1.

As seen from FIG. 1, all three secretion signals resulted in release of GFP-tagged protein from cells as observed by comparison to untransfected control cells. Of the three secretion constructs, the IgK construct showed the highest level of secretion, though clone 2 of the GDNF construct did display similarly high secretion of GFP-tagged protein.

Example 2

A mouse-UBE3A vector construct was generated using a pTR plasmid. The mouse (*Mus musculus*) UBE3A gene was formed from cDNA (U82122.1);

(SEQ ID No. 1)

```
atgaagcgag cagctgcaaa gcatctaata gaacgctact
accatcagtt aactgagggc tgtggaaatg aggcctgcac
gaatgagttt tgtgcttcct gtccaacttt tcttcgtatg
gataacaatg cagcagctat taaagccctt gagctttata
aaattaatgc aaaactctgt gatcctcatc cctccaagaa
aggagcaagc tcagcttacc ttgagaactc aaaaggtgca
tctaacaact cagagataaa aatgaacaag aaggaaggaa
aagattttaa agatgtgatt tacctaactg aagagaaagt
atatgaaatt tatgaatttt gtagagagag tgaggattat
tccccttttaa ttcgtgtaat tggaagaata ttttctagtg
ctgaggcact ggttctgagc tttcggaaag tcaaacagca
cacaaaggag gaattgaaat ctcttcaaga aaaggatgaa
gacaaggatg aagatgaaaa ggaaaaagct gcatgttctg
ctgctgctat ggaagaagac tcagaagcat cttcttcaag
gatgggtgat agttcacagg gagacaacaa tgtacaaaaa
ttaggtcctg atgatgtgac tgtggatatt gatgctatta
gaagggtcta cagcagtttg ctcgctaatg aaaaattaga
aactgccttc ctgaatgcac ttgtatatct gtcacctaac
gtggaatgtg atttgacata tcataatgtg tatactcgag
atcctaatta tctcaatttg ttcattattg taatggagaa
tagtaatctc cacagtcctg aatatctgga aatggcgttg
ccattatttt gcaaagctat gtgtaagcta ccccttgaag
ctcaaggaaa actgattagg ctgtggtcta aatacagtgc
tgaccagatt cggagaatga tggaaacatt tcagcaactt
attacctaca aagtcataag caatgaattt aatagccgaa
atctagtgaa tgatgatgat gccattgttg ctgcttcaaa
gtgtttgaaa atggtttact atgcaaatgt agtgggaggg
gatgtggaca caaatcataa tgaggaagat gatgaagaac
ccatacctga gtccagcgaa ttaacacttc aggagcttct
gggagatgaa agaagaaata agaaaggtcc tcgagtggat
ccactagaaa ccgaacttgg cgttaaaact ctagactgtc
gaaaaccact tatctccttt gaagaattca ttaatgaacc
actgaatgat gttctagaaa tggacaaaga ttataccttt
ttcaaagttg aaacagagaa caaattctct tttatgacat
gtccctttat attgaatgct gtcacaaaga atctgggatt
atattatgac aatagaattc gcatgtacag tgaaagaaga
atcactgttc tttacagcct agttcaagga cagcagttga
```

-continued

```
atccgtattt gagactcaaa gtcagacgtg accatattat
agatgatgca ctggtccggc tagagatgat tgctatggaa
aatcctgcag acttgaagaa gcagttgtat gtggaatttg
aaggagaaca aggagtaatg agggaggcgt ttccaaagag
ttttttcagt tgggttgtgg aggaaatttt taatccaaat
attggtatgt tcacatatga tgaagctacg aaattatttt
ggtttaatcc atcttctttt gaaactgagg gtcaggttta
ctctgattgg catatcctgg gtctggctat ttacaataat
tgtatactgg atgtccattt tcccatggtt gtatacagga
agctaatggg gaaaaaagga acctttcgtg acttgggaga
ctctcaccca gttttatatc agagtttaaa ggatttattg
gaatatgaag ggagtgtgga agatgatatg atgatcactt
tccagatatc acagacagat ctttttggta acccaatgat
gtatgatcta aaagaaaatg gtgataaaat tccaattaca
aatgaaaaca ggaaggaatt tgtcaatctc tattcagact
acattctcaa taaatctgta gaaaaacaat tcaaggcatt
tcgcagaggt tttcatatgg tgactaatga atcgccctta
aaatacttat tcagaccaga agaaattgaa ttgcttatat
gtggaagccg gaatctagat ttccaggcac tagaagaaac
tacagagtat gacggtggct atacgaggga atctgttgtg
attagggagt tctgggaaat tgttcattcg tttacagatg
aacagaaaag actctttctg cagtttacaa caggcacaga
cagagcacct gttggaggac taggaaaatt gaagatgatt
atagccaaaa atggcccaga cacagaaagg ttacctacat
ctcatacttg ctttaatgtc cttttacttc cggaatattc
aagcaaagaa aaacttaaag agagattgtt gaaggccatc
acatatgcca aaggatttgg catgctgtaa.
```

The cDNA was subcloned and sequenced. The mouse UBE3A gene (SEQ ID No. 1) was fused to DNA sequences encoding a secretion signaling peptide (SEQ ID No. 2) and HIV TAT sequence (SEQ ID No. 4). The secretion signaling peptide has the DNA sequence;

atg gcc ctg ttg gtg cac ttc cta ccc ctg ctg gcc ctg ctt gcc ctc tgg gag ccc aaa ccc acc cag gct ttt gtc (SEQ ID No. 2), encoding to protein sequence;

MALLVHFLPLLALLALWEPKPTQAFV (SEQ ID No. 3);

while HIV TAT sequence is;

tac ggc aga aag aag agg agg cag aga agg aga (SEQ ID No. 4), encoding to protein sequence;

YGRKKRRQRRR (SEQ ID No. 5).

Figure 2:
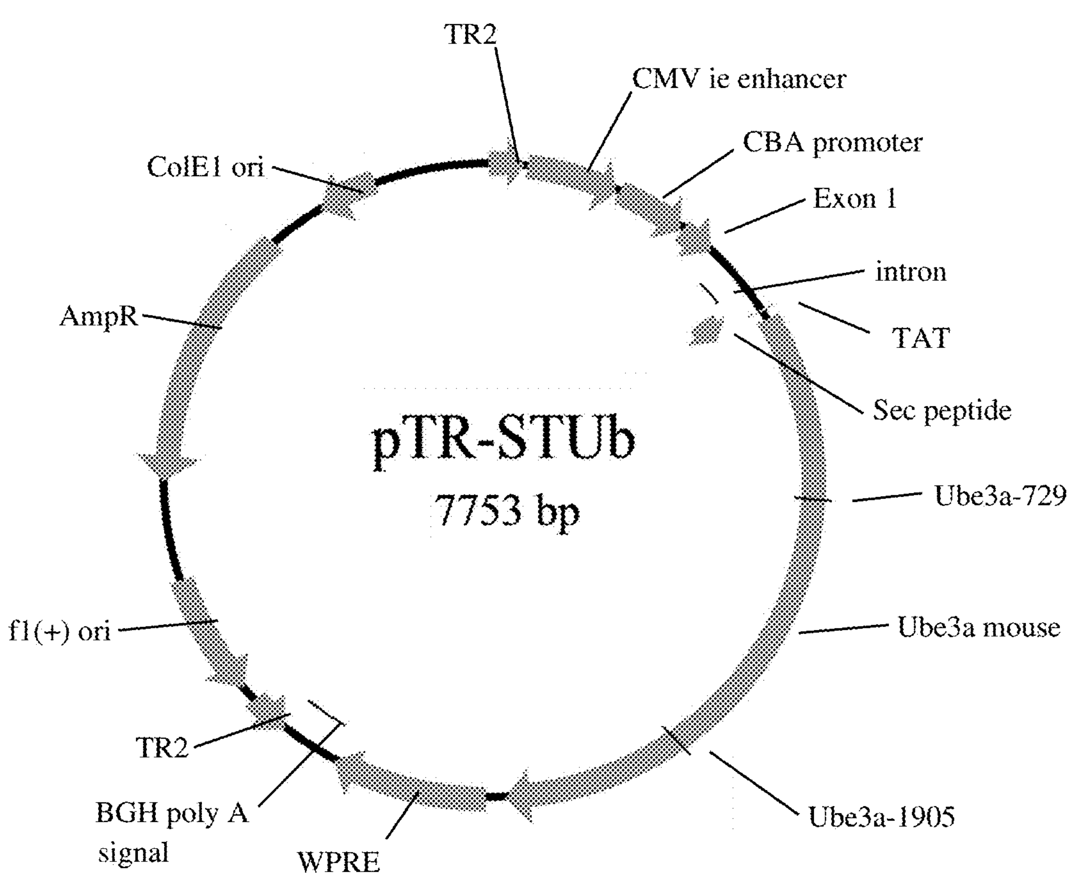
FIG. 2 is a map of the mouse UBE3A vector construct used in the present invention. Major genes are noted.

The construct sequence of SEQ ID No. 1 fused with SEQ ID No. 2 and SEQ ID No. 4 was inserted into a pTR plasmid. The plasmid was cleaved using Age I and Xho I endonucleases and the construct sequence ligated using ligase. The vector contains AAV serotype 2 terminal repeats, CMV-chicken-beta actin hybrid promoter and a WPRE, seen in FIG. 2. The recombinant plasmid lacks the Rep and Cap elements, limiting integration of the plasmid into host DNA.

The vector (AAV4-STUb vector) was then transformed into *Escherichia coli* (*E. coli*, Invitrogen, Thermo Fisher Scientific, Inc., Waltham, MA; SURE2 cells). Briefly, cells were equilibrated on ice and 1 μg to 500 ng of the vector were added to the *E. coli* and allowed to incubate for about 1 minute. The cells were electroporated with a BioRad Gene Pulser in a 0.1 cm cuvette (1.7V, 200 Ohms). The *E. Coli* were then grown in media for 60 min prior to being plated onto agar, such as ATCC medium 1065 (American Type Culture Collection, Manassas, VA), with ampicillin (50 μg/mL).

*E. coli* was expanded in broth containing ampicillin to collect large amounts of vector.

Example 3

The mouse vector properties of the construct generated in Example 2 were tested in HEK293 cells (American Type Culture Collection, Manassas, VA). HEK293 cells were grown at 37° C. 5% $CO_2$ in Dulbecco's Modified Essential Medium (DMEM) with 10% FBS and 1% Pen/Strep and subcultured at 80% confluence.

The vector (2 μg/well in a 6-well plate) was transfected into the cells using PEI transfection method. The cells were subcultured at $0.5\times10^6$ cells per well in a 6-well plate with DMEM medium two days before the transfection. Medium was replaced the night before transfection. Endotoxin-free $dH_2O$ was heated to around 80° C., and polyethylenimine (Sigma-Aldrich Co. LLC, St. Louis, MO) dissolved. The solution was allowed to cool to around 25° C., and the solution neutralized using sodium hydroxide. AAV4-STUb vector or negative control (medium only) was added to serum-free DMEM at 2 μg to every 200 μl for each well transfected, and 9 μl of 1 μg/μl polyethylenimine added to the mix for each well. The transfection mix was incubated at room temperature for 15 minutes, then added to each well of cells at 210 μl per well and incubated for 48 hours.

Figure 3:
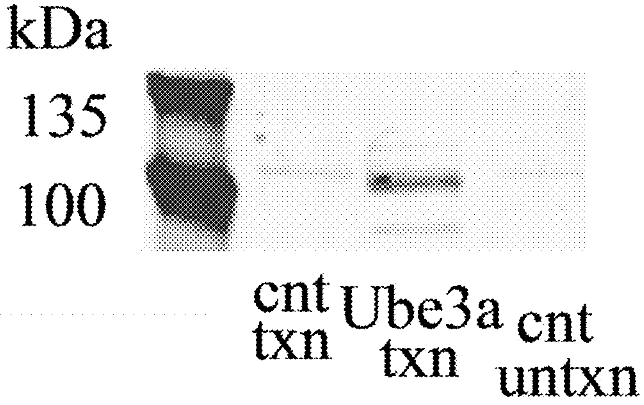
FIG. 3 is a Western blot showing secretion of E6-AP protein from plasmid transfected HEK293 cells. Culture media taken from control cells transfected cell culture media (cnt txn), media from Ube3a transfected cells (Ube3a txn); and media from untransfected cells (cnt untxn) were run on an acrylamide gel and anti-E6-AP antibody.

Media was collected from AAV4-STUb vector transfected cells, medium-only transfected control cells, and untransfected control cells. The medium was run on Western blot and stained with rabbit anti-E6-AP antibody (A300-351A, Bethyl Labs, Montgomery, TX), which is reactive against human and mouse E6-AP, at 0.4 μg/ml. Secondary conjugation was performed with rabbit-conjugated horseradish peroxidase (Southern Biotechnology, Thermo Fisher Scientific, Inc., Waltham, MA). The results were determined densiometrically, and show the HEK293 cells transfected with AAV4-STUb secrete E6-AP protein into the medium, as seen in FIG. 3.

Example 4

Transgenic mice were formed by crossbreeding mice having a deletion in the maternal UBE3A (Jiang, et al., Mutation of the Angelman ubiquitin ligase in mice causes increased cytoplasmic p53 and deficits of contextual learning and long-term potentiation. Neuron. 1998 October; 21 (4): 799-811; Gustin, et al., Tissue-specific variation of Ube3a protein expression in rodents and in a mouse model of Angelman syndrome. Neurobiol Dis. 2010 September; 39 (3): 283-91); Heck, et al., Analysis of cerebellar function in Ube3a-deficient mice reveals novel genotype-specific behaviors. Hum Mol Genet. 2008 Jul. 15; 17 (14): 2181-9) and GABARB3. Mice were housed in a 12 hour day-light cycle and fed food and water ad libitum. Three month old mice were treated with the vector.

Mice were anesthetized with isoflurane and placed in the stereotaxic apparatus (51725D Digital Just for Mice Stereotaxic Instrument, Stoelting, Wood Dale, IL). An incision was made sagitally over the middle of the cranium and the surrounding skin pushed back to enlarge the opening. The following coordinates were used to locate the left and right hippocampus: AP 22.7 mm, L 62.7 mm, and V 23.0 mm. Mice received bilateral intrahippocampal injections of either AAV4-STUb particles at a concentration of $1\times10^{12}$ genomes/mL (N=2) in 10 μL of 20% mannitol or vehicle (10 μL of 20% mannitol) using a 10 mL Hamilton syringe in each hemisphere. The wound was cleaned with saline and closed using Vetbond (NC9286393 Fisher Scientific, Pittsburgh, PA). Control animals included uninjected AS mice and littermate wild type mice (n=2). Mice recovered in a clean, empty cage on a warm heating pad and were then singly housed until sacrificed. The mice were monitored over the course of the experiment.

At day 30 after treatment, the mice were euthanized by injecting a commercial euthanasia solution, Somnasol®, (0.22 ml/kg) intraperitoneally. After euthanizing the animals, CSF was collected and the animals were perfused with PBS and the brain removed. The brain was fixed in 4% paraformaldehyde solution overnight prior to cryoprotection in sucrose solutions. Brains were sectioned at 25 μm using a microtome.

Most recombinant adeno-associated virus vector studies inject the vector directly into the parenchymal, which typically results in limited cellular transduction (Li, et al., Intra-ventricular infusion of rAAV-1-EGFP resulted in transduction in multiple regions of adult rat brain: a comparative study with rAAV2 and rAAV5 vectors. Brain Res. 2006 Nov. 29; 1122 (1): 1-9). However, appending a secretion signaling sequence and TAT sequence to the Ube3A protein allows for secretion of the HECT protein (i.e., UBE3A) from transfected cells and uptake of the peptide by adjacent neurons, allowing injection into a discrete site to service as a supply of protein for other sites throughout the brain.

Brains from sacrificed mice were sliced using a microtome and stained for E6-AP protein using anti-E6-AP antibody (A300-351A, Bethyl Labs, Montgomery, TX) with a biotinylated anti-rabbit secondary antibody (Vector Labs #AB-1000). Staining was completed with ABC (Vector Labs) and DAB reaction. Sections were mounted and scanned using Zeiss Axio Scan microscope. Percentage area staining was quantified using IAE-NearCYTE image analysis software (University of Pittsburgh Starzl Transplant Institute, Pittsburgh, PA).

Figure 4:
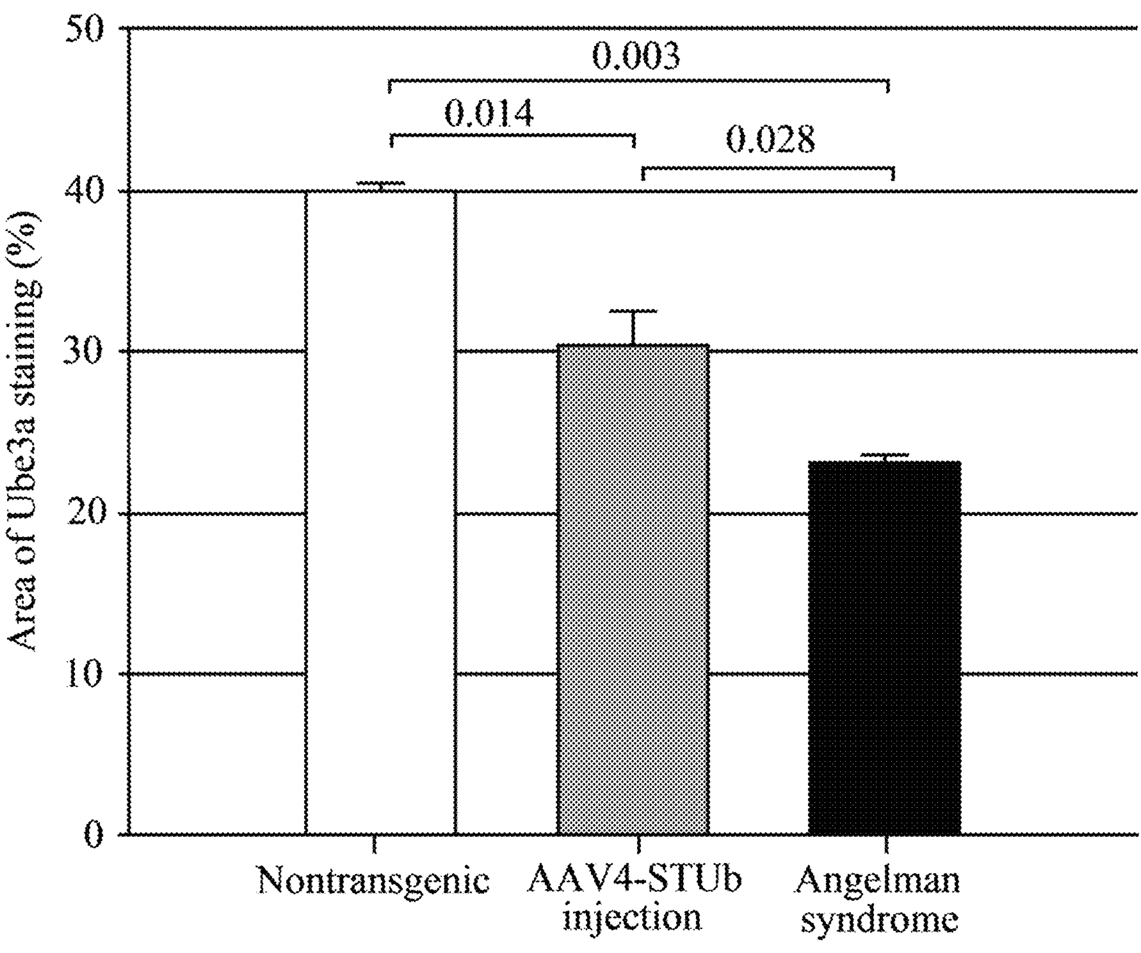
FIG. 4 is a graph of percentage area staining for E6-AP protein. Nontransgenic (Ntg) control mice shows the level of Ube3a expression in a normal mouse brain. Angelman syndrome mice (AS) show staining level in those mice (aka background staining). Injection of AAV4-STUb into the lateral ventricles of an AS mouse shows the level of E6-AP protein staining is increased as compared to an AS mouse. n=2

Nontransgenic (Ntg) control mice show the level of Ube3a expression in a normal mouse brain, which was about 40%, as seen in FIG. 4. By comparison, Angelman syndrome mice (AS) show Ube3a protein staining levels of about 25%. Insertion of the AAV4-STUb vector into the lateral ventricles of an AS mouse shows the vector increased the level of E6-AP to around 30-35%.

Figure 5:
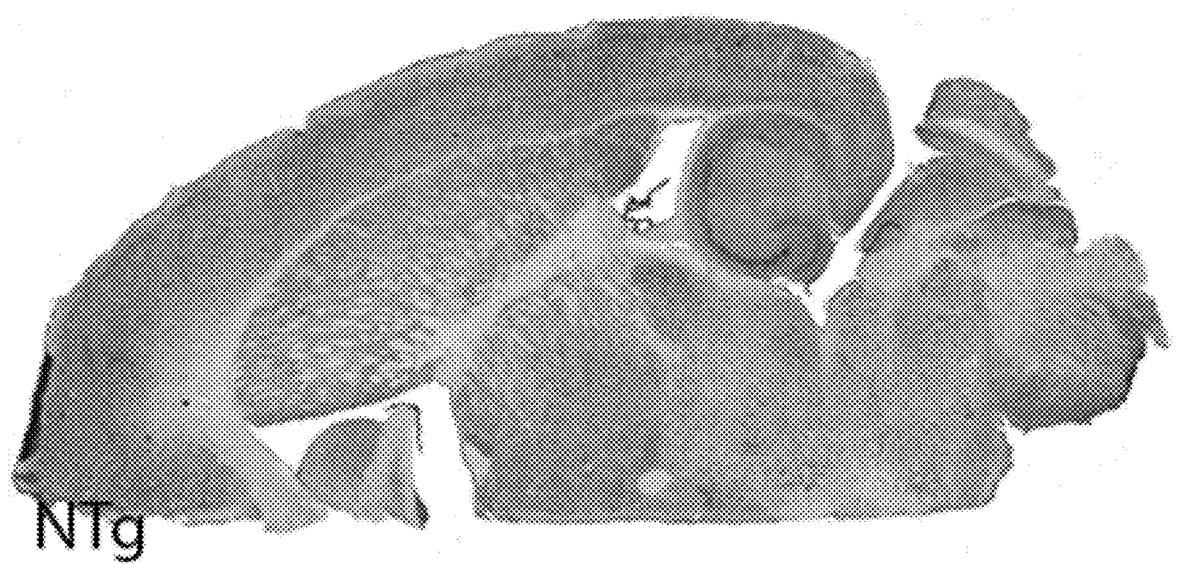
FIG. 5 is a microscopic image of anti-E6-AP staining in a nontransgenic mouse. GFP (green fluorescent protein) is a cytosolic protein which is not secreted. This suggests that the Ube3a is being released from the ependymal cells and taken up in the parenchyma.
Figure 6:
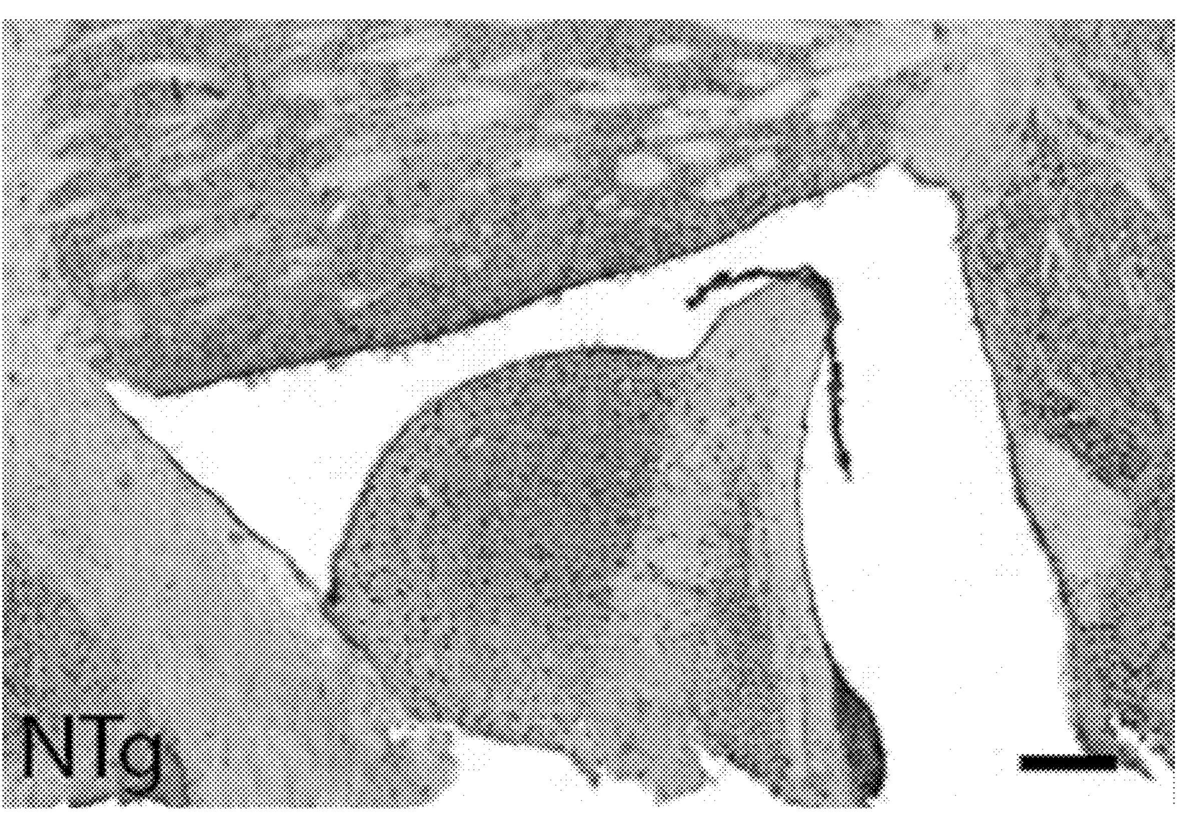
FIG. 6 is a microscopic image of anti-E6-AP staining in a nontransgenic mouse showing higher magnification images of the ventricular system (Lateral ventricle (LV), 3$^{rd}$ ventricle). GFP (green fluorescent protein) is a cytosolic protein which is not secreted. This suggests that the Ube3a is being released from the ependymal cells and taken up in the parenchyma.
Figure 7:
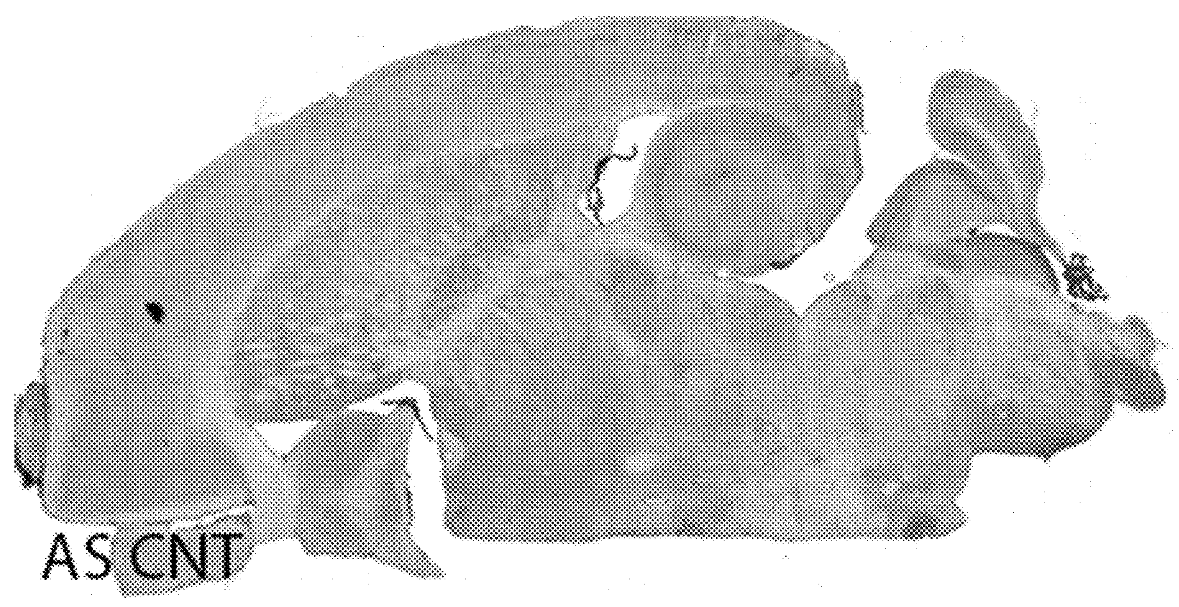
FIG. 7 is a microscopic image of anti-E6-AP staining in an uninjected AS mouse.
Figure 8:
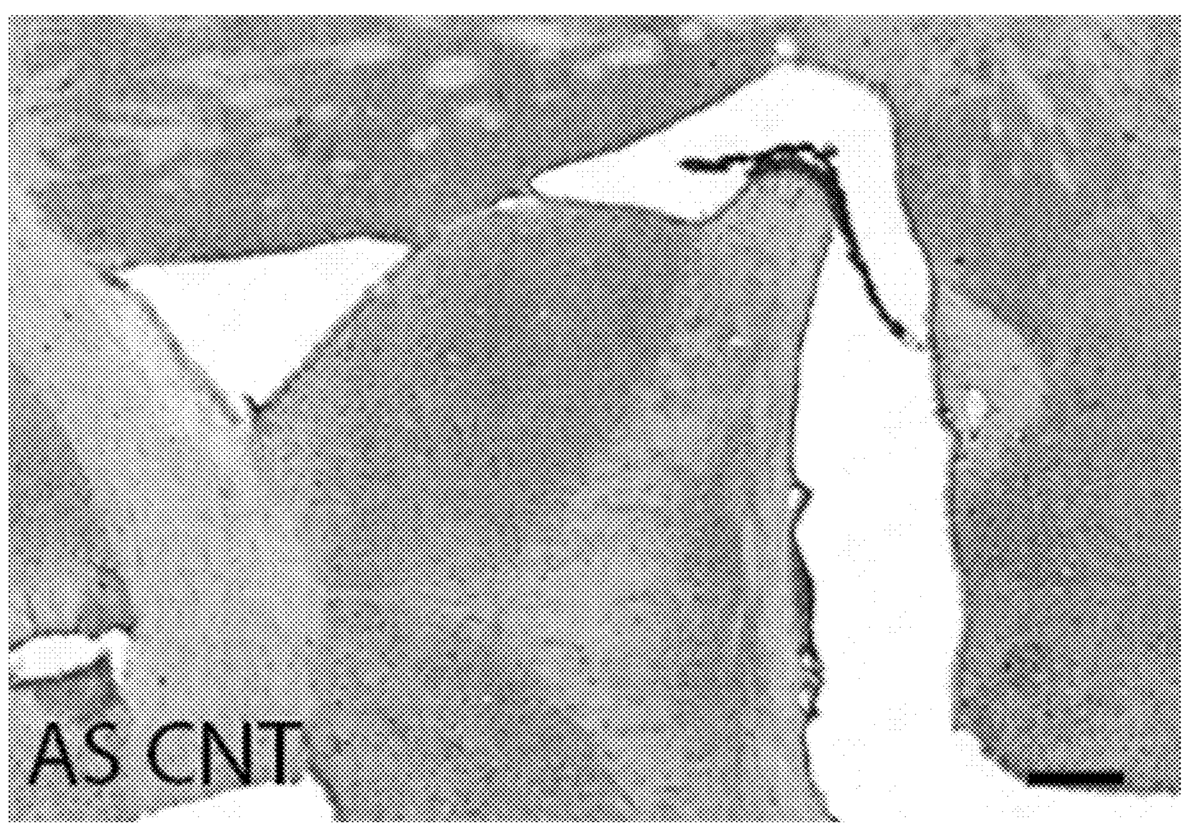
FIG. 8 is a microscopic image of anti-E6-AP staining in an uninjected AS mouse. showing higher magnification images of the ventricular system (Lateral ventricle (LV), 3$^{rd}$ ventricle).
Figure 9:
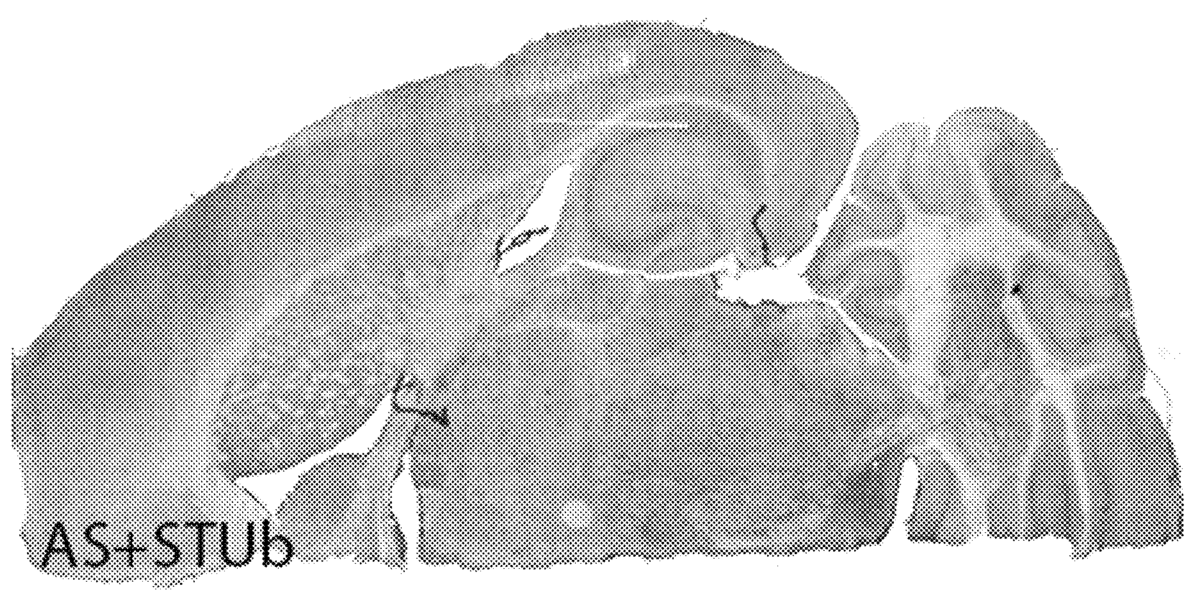
FIG. 9 is a microscopic image of anti-E6-AP staining in an AS mouse injected into the lateral ventricle with AAV4-STUb. Expression can be seen in the ependymal cells but staining is also observed in the parenchyma immediately adjacent to the ventricles. GFP (green fluorescent protein) is a cytosolic protein which is not secreted. This suggests that the Ube3a is being released from the ependymal cells and taken up in the parenchyma.
Figure 10:
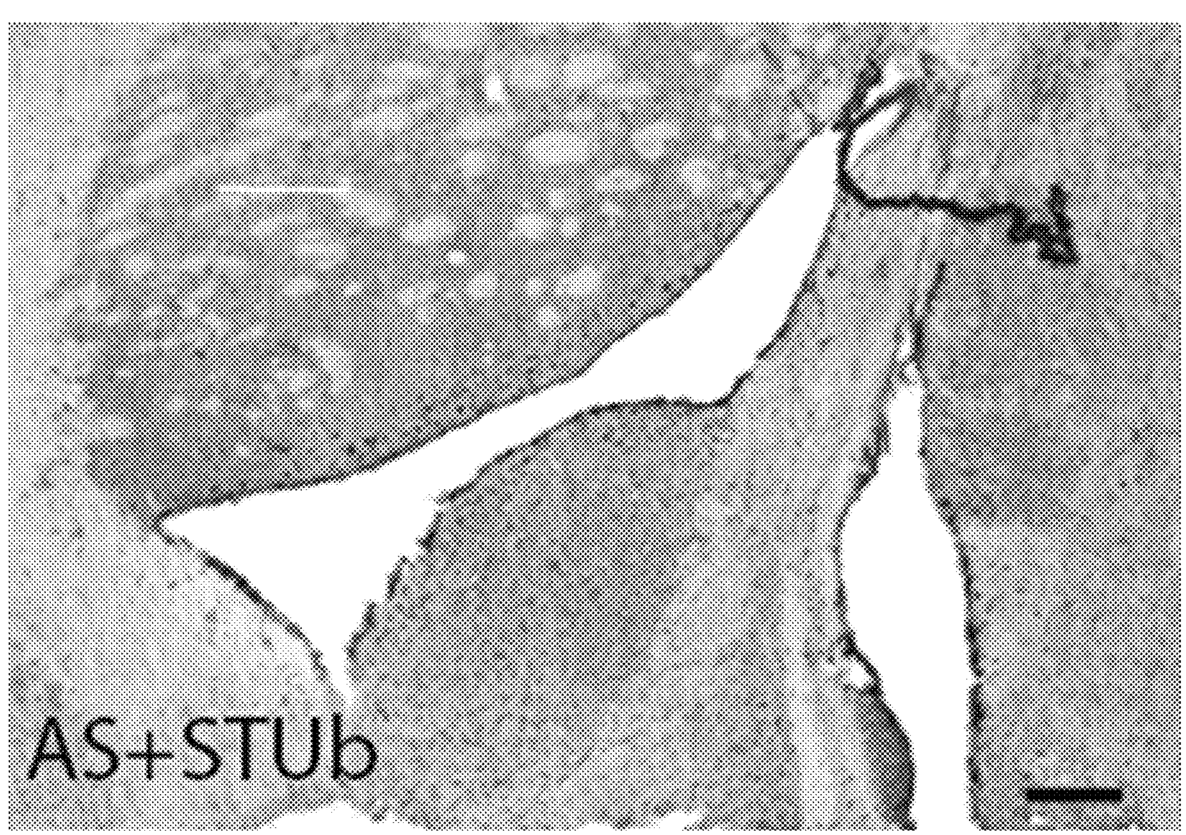
FIG. 10 is a microscopic image of anti-E6-AP staining in an AS mouse injected into the lateral ventricle with AAV4-STUb showing higher magnification images of the ventricular system (Lateral ventricle (LV), 3$^{rd}$ ventricle). Expression can be seen in the ependymal cells but staining is also observed in the parenchyma immediately adjacent to the ventricles (indicated with arrows). GFP (green fluorescent protein) is a cytosolic protein which is not secreted. This suggests that the Ube3a is being released from the ependymal cells and taken up in the parenchyma.
Figure 11:
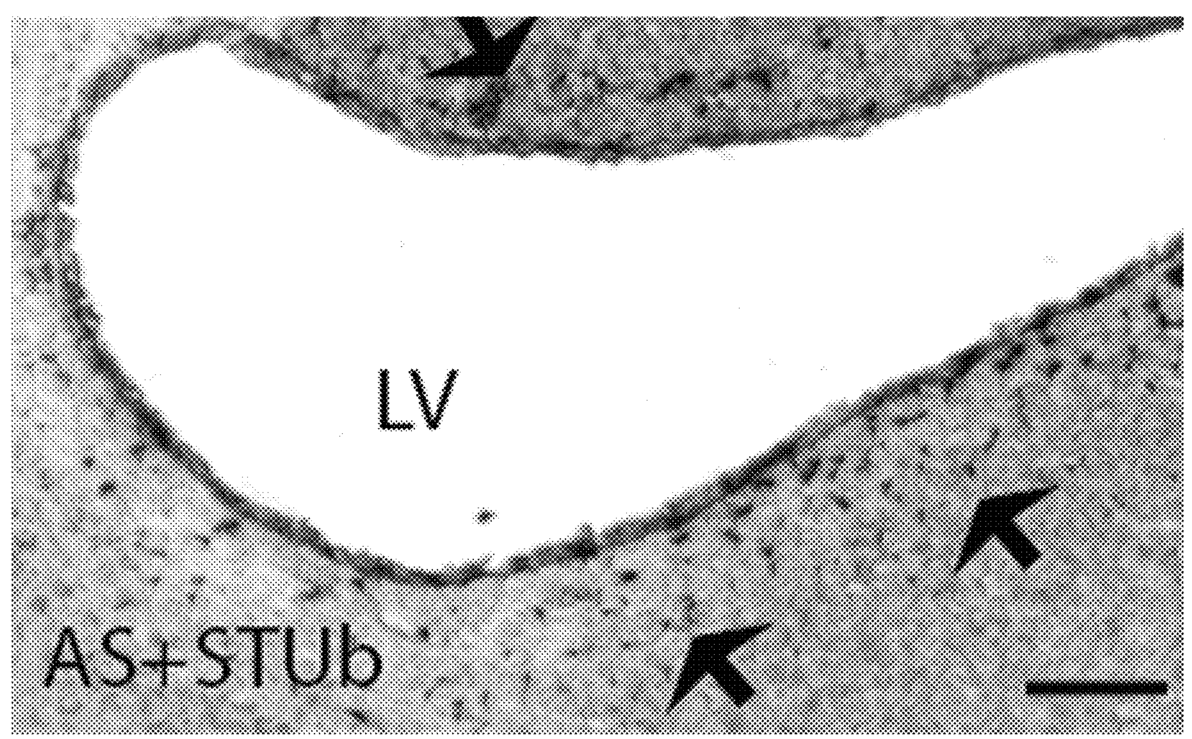
FIG. 11 is a microscopic image of anti-E6-AP staining in an AS mouse injected into the lateral ventricle with AAV4-STUb. Higher magnification images of the ventricular system (Lateral ventricle (LV)) of Ube3a expression after AAV4-STUb delivery. Expression can be seen in the ependymal cells but staining is also observed in the parenchyma immediately adjacent to the ventricles (indicated with arrows). GFP (green fluorescent protein) is a cytosolic protein which is not secreted. This suggests that the Ube3a is being released from the ependymal cells and taken up in the parenchyma.
Figure 12:
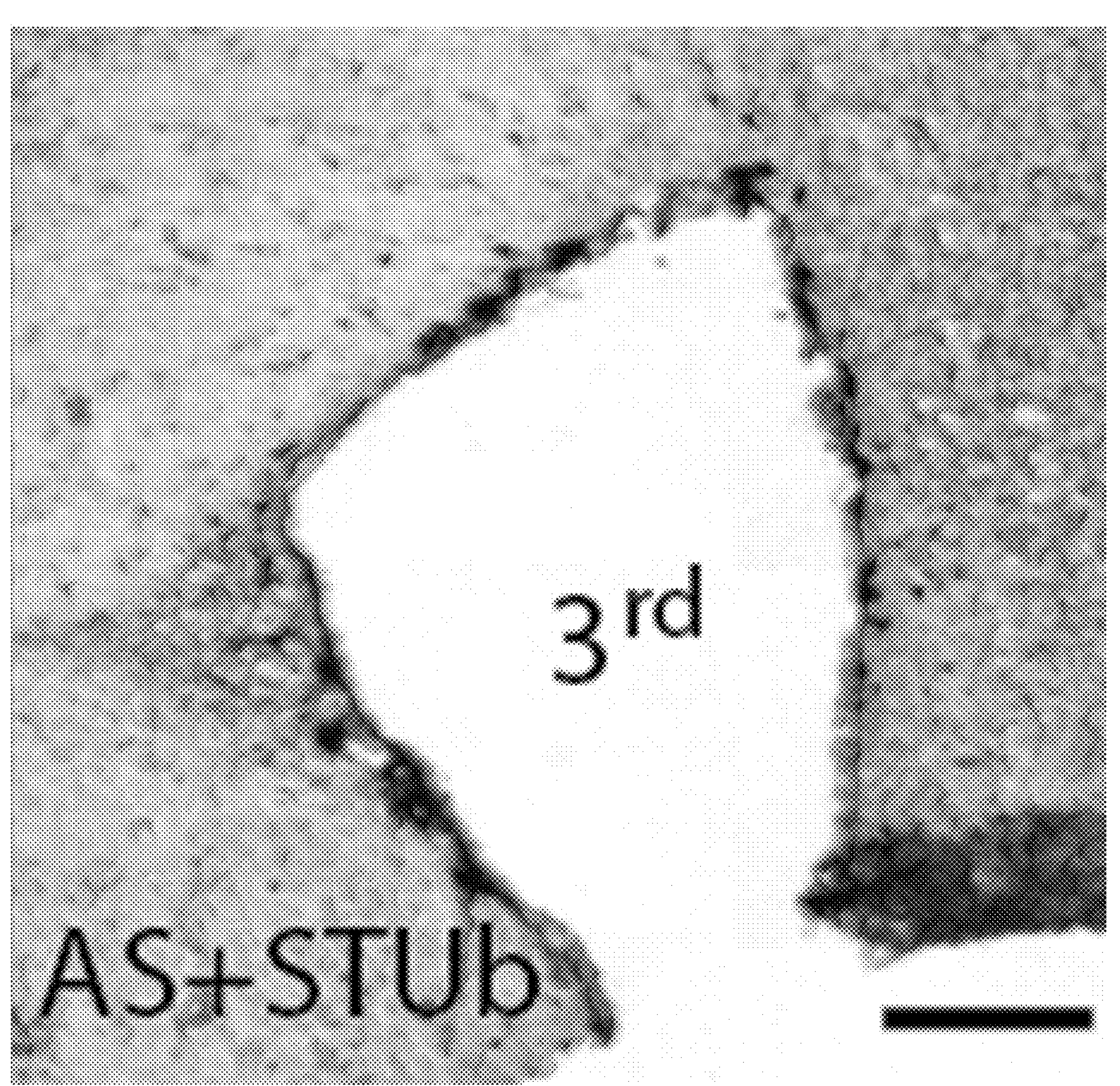
FIG. 12 is a microscopic image of anti-E6-AP staining in an AS mouse injected into the lateral ventricle with AAV4-STUb. Higher magnification images of the ventricular system (3$^{rd}$ ventricle) of Ube3a expression after AAV4-STUb delivery. Expression can be seen in the ependymal cells but staining is also observed in the parenchyma immediately adjacent to the ventricles (indicated with arrows). GFP (green fluorescent protein) is a cytosolic protein which is not secreted. This suggests that the Ube3a is being released from the ependymal cells and taken up in the parenchyma.
Figure 13:
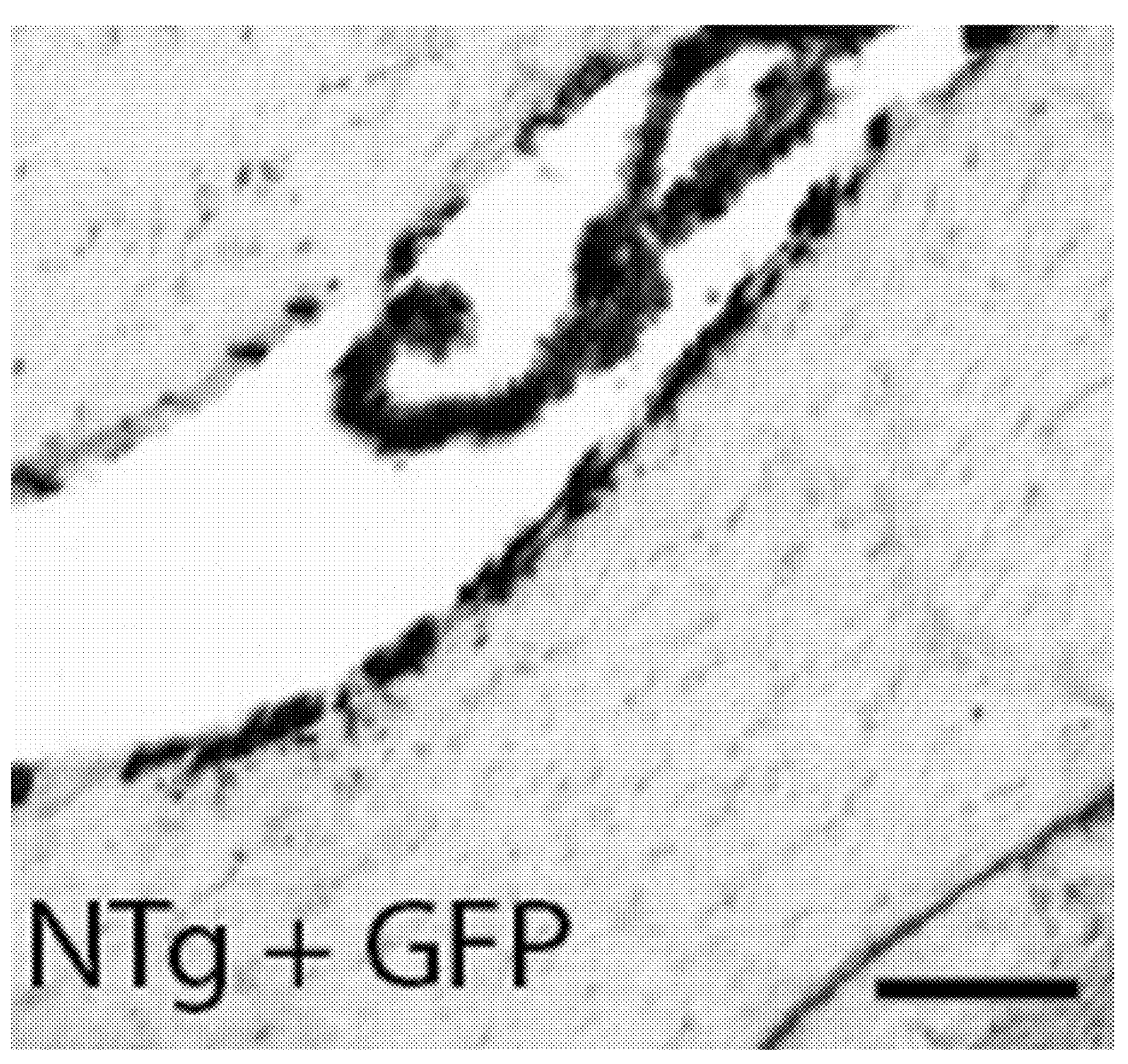
FIG. 13 is a microscopic image of anti-E6-AP staining in a nontransgenic mouse transfected with GFP. Expression is not observed with the AAV4-GFP injections, which shows only transduction of the ependymal and choroid plexus cells. GFP (green fluorescent protein) is a cytosolic protein which is not secreted. This suggests that the Ube3a is being released from the ependymal cells and taken up in the parenchyma.
Figure 14:
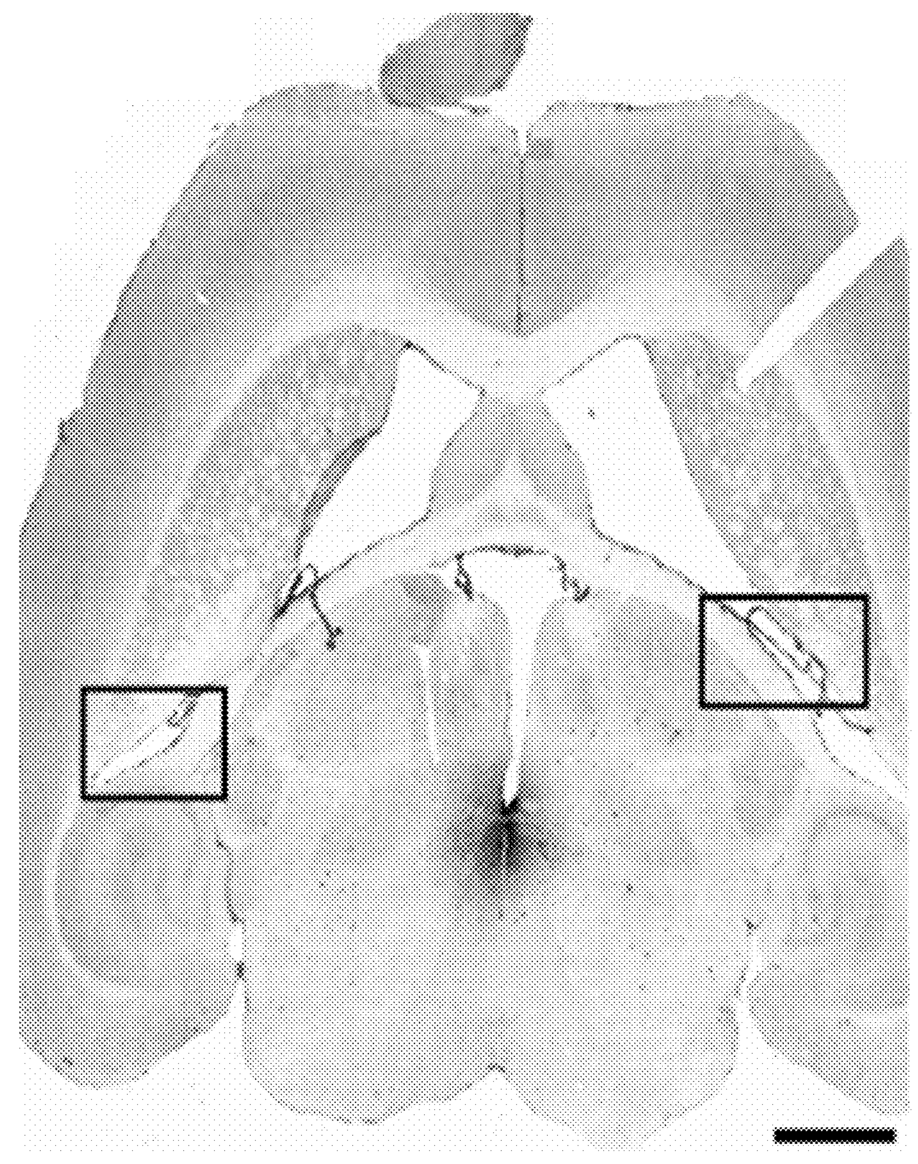
FIG. 14 is a microscopic image of anti-E6-AP staining in an AS mouse injected into the lateral ventricle with AAV4-STUb. Coronal cross section of the brain of Ube3a expression after AAV4-STUb delivery.
Figure 15:
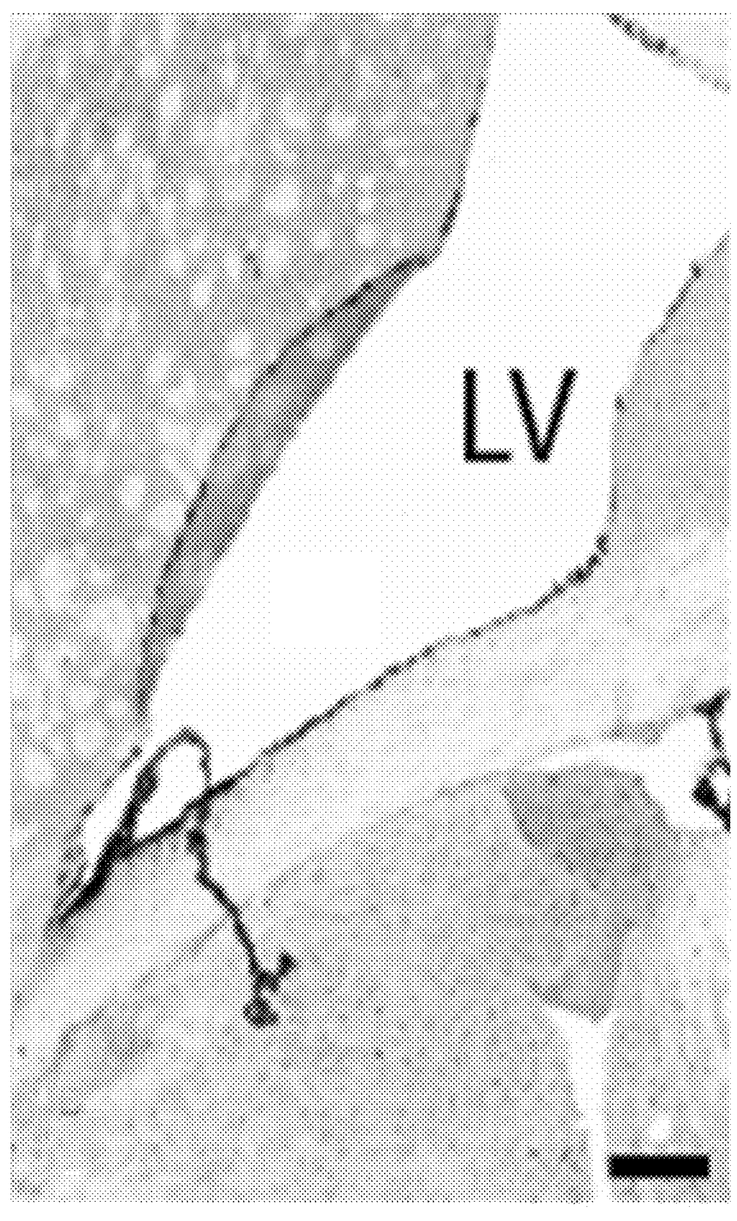
FIG. 15 is a microscopic image of anti-E6-AP staining in an AS mouse injected into the lateral ventricle with AAV4-STUb. Coronal cross section of the lateral ventricle (LV) in the brain showing Ube3a expression after AAV4-STUb delivery.
Figure 16:
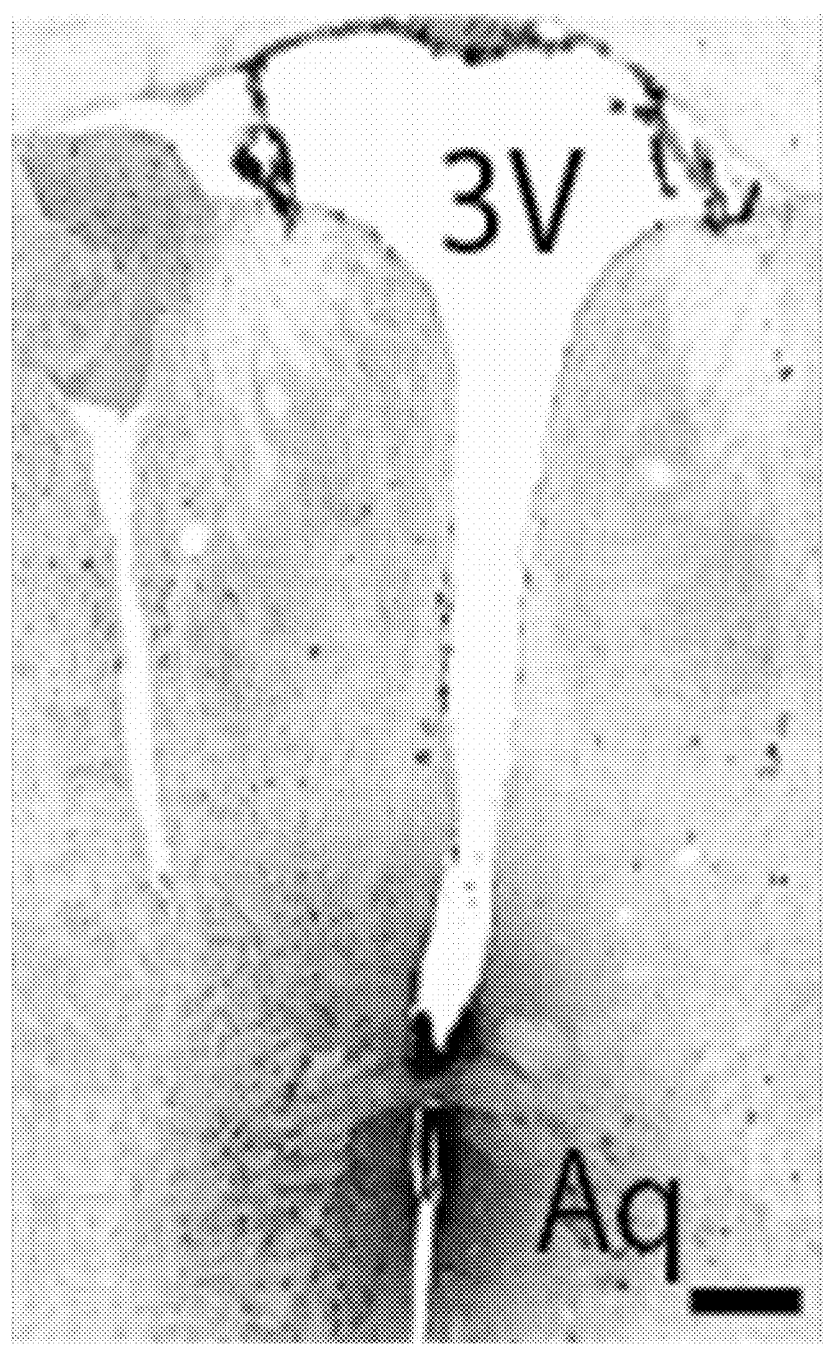
FIG. 16 is a microscopic image of anti-E6-AP staining in an AS mouse injected into the lateral ventricle with AAV4-STUb. Coronal cross section of the 3$^{rd}$ ventricle (3V) in the brain showing Ube3a expression after AAV4-STUb delivery.
Figure 17:
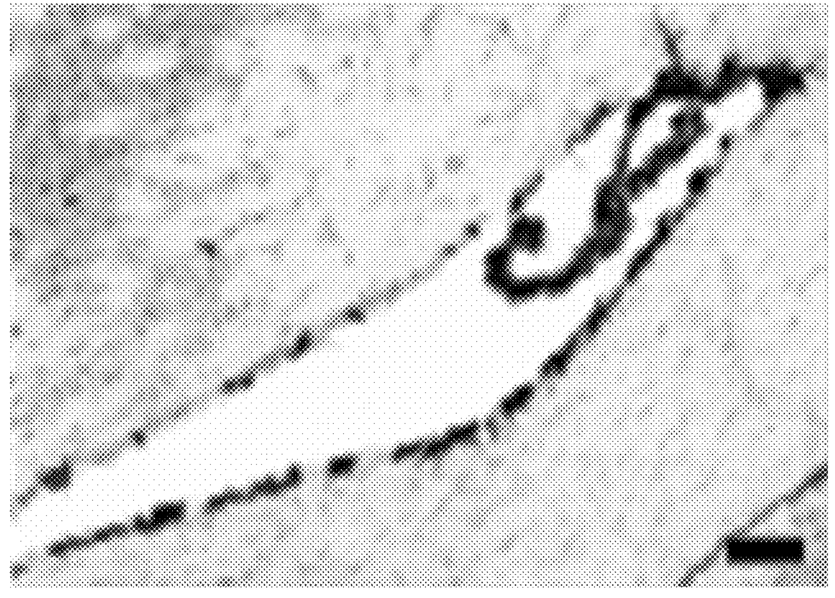
FIG. 17 is a microscopic image of anti-E6-AP staining in an AS mouse injected into the lateral ventricle with AAV4-STUb. Coronal cross section of the interior horn of the lateral ventricle (LV) in the brain showing Ube3a expression after AAV4-STUb delivery.
Figure 18:
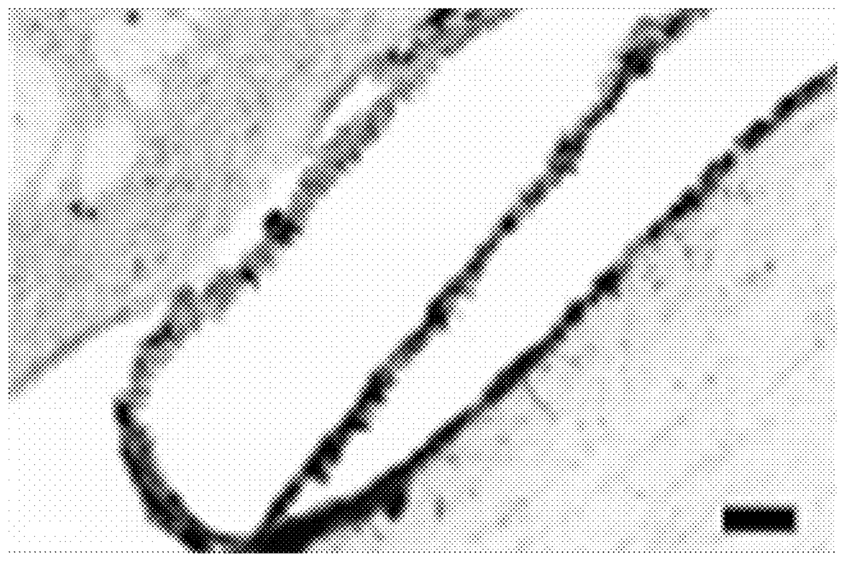
FIG. 18 is a microscopic image of anti-E6-AP staining in an AS mouse injected into the lateral ventricle with AAV4-STUb. Coronall cross section of the lateral ventricle (4V) in the brain showing Ube3a expression after AAV4-STUb delivery.
Figure 19:
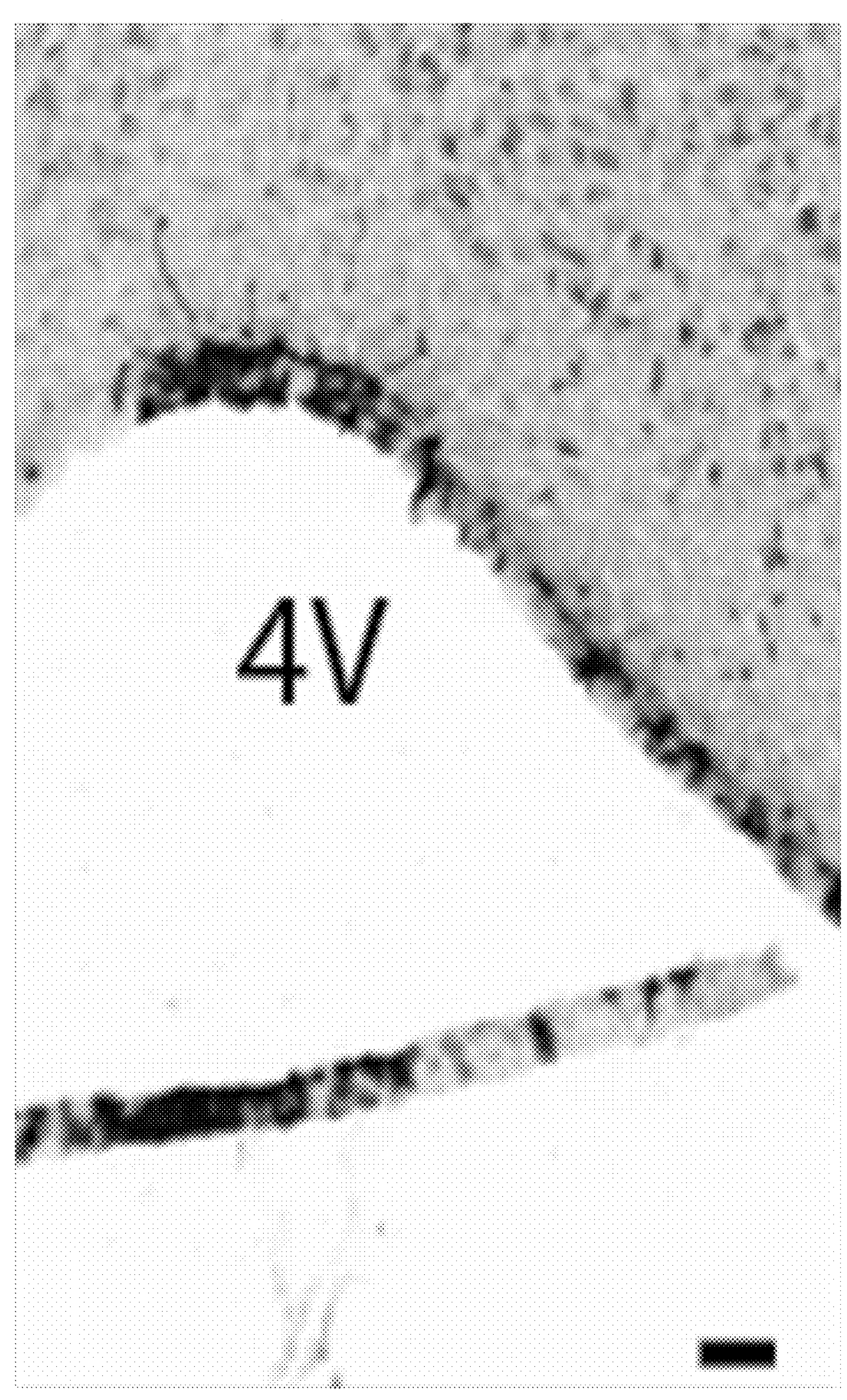
FIG. 19 is a microscopic image of anti-E6-AP staining in an AS mouse injected into the lateral ventricle with AAV4-STUb. Coronal cross section of the fourth ventricle (LV) in the brain showing Ube3a expression after AAV4-STUb delivery.
Figure 20:
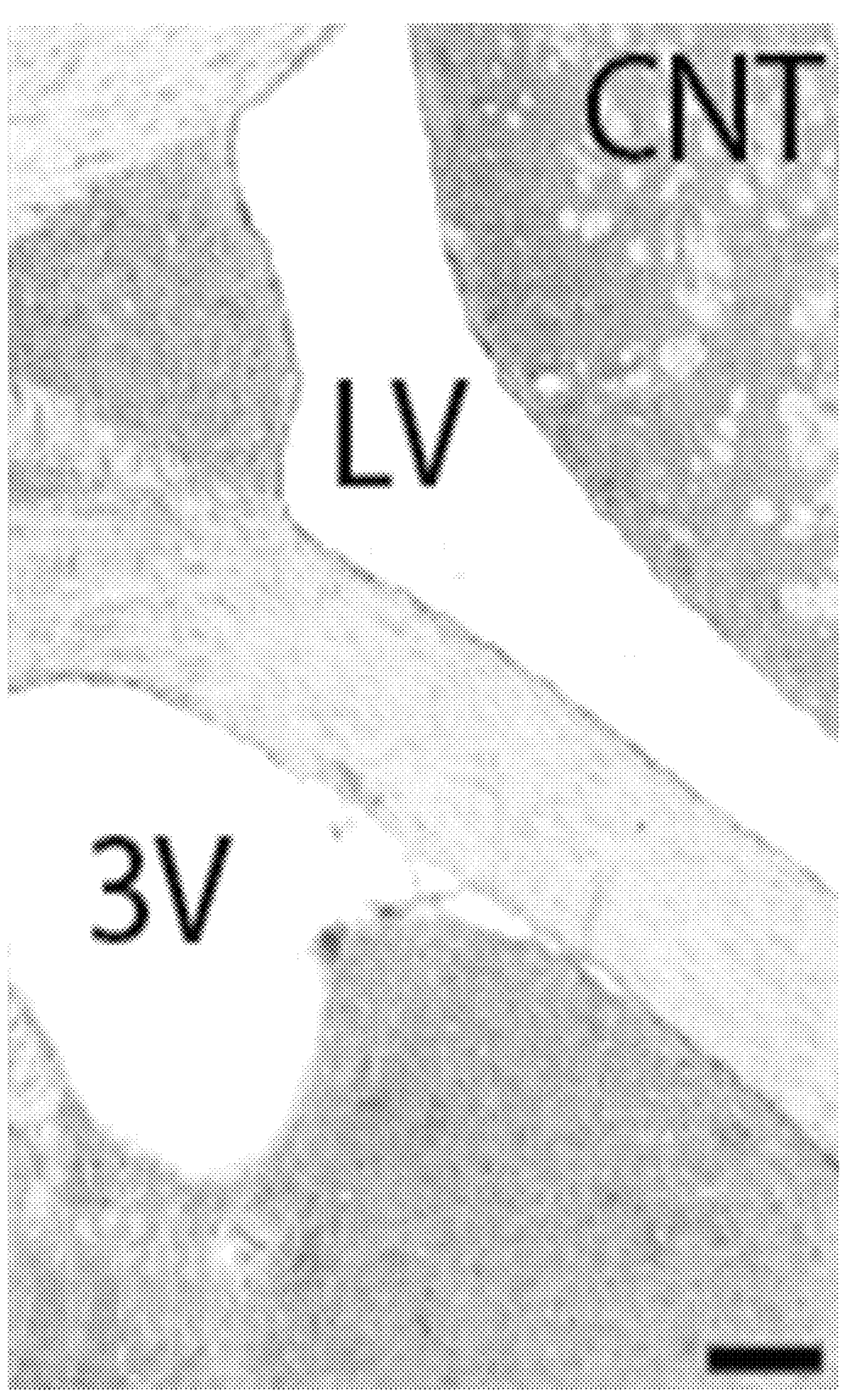
FIG. 20 is a microscopic image of anti-E6-AP staining in an AS mouse injected into the lateral ventricle with AAV4-STUb. Coronal cross section of the brain with higher magnification images of the ventricular system on the lateral ventricle (LV), and (C) 3$^{rd}$ ventricle (3V) of Ube3a expression after AAV4-STUb delivery.

Immunohistochemical analysis of brain slices indicate nontransgenic mice possess relatively high levels of E6-AP, with region-specific staining, seen in FIGS. 5 and 6. In Angelman syndrome-model mice, staining patterns of E6-AP are similar, but the levels of E6-AP are drastically reduced, seen in FIGS. 7 and 8, as expected. Administration of the mouse UBE3A vector to Angelman syndrome model mice did increase levels of E6-AP, though not to the level of nontransgenic mice, as seen in FIGS. 9 and 10. A detailed analysis of the lateral ventricle shows that the injection of UBE3A vector resulted in uptake of the vector by ependymal cells, as seen in FIG. 11. However, in addition to the uptake of UBE3A vector and expression of E6-AP by ependymal cells, adjacent cells in the parenchyma also stained positive for E6-AP, as seen by arrows in the Figure. Moreover, staining was seen in more distal locations, such as the 3d ventricle, seen in FIG. 12. This indicates that E6-AP was being secreted by the transfected cells and successfully uptaken by adjacent cells, confirming that the construct can be used to introduce E6-AP and that the E6-AP construct can be used as a therapeutic to treat global cerebral deficiency in E6-AP expression, such as Angelman syndrome. Control treatment using AAV4-GFP vector did not exhibit uptake of the control protein, as seen in FIG. 13, as only transduction of the ependymal and choroid plexus cells.

Detailed analysis of the coronal cross sections of Angelman syndrome-model mice confirmed that administration of the UBE3A construct increased levels of E6-AP in and around the lateral ventricle, as seen in FIGS. 14 through 20.

Example 5

A human vector construct was generated using a pTR plasmid. A *Homo sapiens* UBE3A gene was formed from cDNA (AH005553.1);

```
                                   (SEQ ID No. 6)
ggagtagttt actgagccac taatctaaag tttaatactg
tgagtgaata ccagtgagta cctttgttaa tgtggataac
caatacttgg ctataggaag ttttttagtt gtgtgtttta
tnacacgtat ttgactttgt gaataattat ggcttataat
ggcttgtctg ttggtatcta tgtatagcgt ttacagtttc
ctttaaaaaa catgcattga gttttttaat agtccaaccc
ttaaaataaa tgtgttgtat ggccacctga tctgaccact
ttctttcatg ttgacatctt taattttaaa actgttttat
ttagtgctta aatcttgttn acaaaattgt cttcctaagt
aatatgtcta cctttttttt tggaatatgg aatattttgc
taactgtttc tcaattgcat tttacagatc aggagaacct
cagtctgacg acattgaagc tagccgaatg taagtgtaac
ttggttgaga ctgtggttct tattttgagt tgccctagac
tgctttaaat tacgtcacat tatttggaaa taatttctgg
ttaaaagaaa ggaatcattt agcagtaaat gggagatagg
aacataccta cttttttcc tatcagataa ctctaaacct
cggtaacagt ttactaggtt tctactacta gatagataaa
tgcacacgcc taaattctta gtctttttgc ttccctggta
gcagttgtag ggaaataggg aggttgagga aagagtttaa
cagtctcaac gcctaccata tttaaggcat caagtactat
gttatagata cagagatgcg taataattag ttttcaccct
acagaaattt atattatact caagagtgaa agatgcagaa
gcaaataatt tcagtcactg aggtagaatg gtatccaaaa
tacaatagta acatgaagga gtactggagt accaggtatg
caataggaat ctagtgtaga tggcagggaa gtaagagtgg
```

-continued

```
ccaggaaatg ctaagttcag tcttgaaatg tgactgggaa
tcaggcagct atcaactata agtcaaatgt ttacaagctg
ttaaaaatga aatactgatt atgtaaaaga aaaccggatt
gatgctttaa atagactcat tttcntaatg ctaattttta
aaatgataga atcctacaan tcttagctgt aaaccttgtg
atttttcagc tgttgtacta aacaacttaa gcacatatac
catcagacaa gcccccntcc ccccttttaa accaaaggaa
tgtatactct gttaatacag tcagtaagca ttgacattct
ttatcataat atcctagaaa atatttatta actatttcac
tagtcaggag ttgtggtaaa tagtgcatct ccattttcta
cttctcatct tcatacacag gttaatcact tcagtgcttg
actaactttt gccttgatga tatgttgagc tttgtacttg
agagctgtac taatcactgt gcttattgtt tgaatgtttg
gtacaggaag cgagcagctg caaagcatct aatagaacgc
tactaccacc agttaactga gggctgtgga aatgaagcct
gcacgaatga gttttgtgct tcctgtccaa cttttcttcg
tatggataat aatgcagcag ctattaaagc cctcgagctt
tataagatta atgcaaaact ctgtgatcct catccctcca
agaaaggagc aagctcagct taccttgaga actcgaaagg
tgccccccaac aactcctgct ctgagataaa aatgaacaag
aaaggcgcta gaattgattt taaaggtaag atgttttatt
ttcaattgag aattgttgcc tgaaaaccat gtgggagatt
taaatgtatt agtttttatt tgttttttct tctgtgacat
aaagacattt tgatatcgta gaaccaattt tttattgtgg
taacggacag gaataataac tacattttac aggtctaatc
attgctaatt agaagcagat catatgccaa aagttcattt
gttaatagat tgatttgaac tttttaaaat tcttaggaaa
aatgtattaa gtggtagtga atctccaaaa ctatttaaga
gctgtattat gattaatcag tacatgacat attggttcat
atttataatt aaagctatac attaatagat atcttgatta
taaagaaagt ttaaactcat gatcttatta agagttatac
attgttgaaa gaatgtaaaa gcatgggtga ggtcattggt
ataggtaggt agttcattga aaaaaatagg taagcattaa
attttgtttg ctgaatctaa gtattagata ctttaagagt
tgtatatcat aaatgatatt gagcctagaa tgtttggctg
ttttactttt agaacttttt gcaacagagt aaacatacat
attatgaaaa taaatgttct ctttttttcct ctgattttct
agatgtgact tacttaacag aagagaaggt atatgaaatt
cttgaattat gtagagaaag agaggattat tccccctttaa
tccgtgttat tggaagagtt ttttctagtg ctgaggcatt
ggtacagagc ttccggaaag ttaaacaaca caccaaggaa
```

-continued

```
gaactgaaat ctcttcaagc aaaagatgaa gacaaagatg
aagatgaaaa ggaaaaagct gcatgttctg ctgctgctat
ggaagaagac tcagaagcat cttcctcaag gataggtgat
agctcacagg gagacaacaa tttgcaaaaa ttaggccctg
atgatgtgtc tgtggatatt gatgccatta gaagggtcta
caccagattg ctctctaatg aaaaaattga aactgccttt
ctcaatgcac ttgtatattt gtcacctaac gtggaatgtg
acttgacgta tcacaatgta tactctcgag atcctaatta
tctgaatttg ttcattatcg taatggagaa tagaaatctc
cacagtcctg aatatctgga aatggctttg ccattatttt
gcaaagcgat gagcaagcta ccccttgcag cccaaggaaa
actgatcaga ctgtggtcta aatacaatgc agaccagatt
cggagaatga tggagacatt tcagcaactt attacttata
aagtcataag caatgaattt aacagtcgaa atctagtgaa
tgatgatgat gccattgttg ctgcttcgaa gtgcttgaaa
atggtttact atgcaaatgt agtgggaggg gaagtggaca
caaatcacaa tgaagaagat gatgaagagc ccatccctga
gtccagcgag ctgacacttc aggaactttt gggagaagaa
agaagaaaca agaaaggtcc tcgagtggac cccctggaaa
ctgaacttgg tgttaaaacc ctggattgtc gaaaaccact
tatccctttt gaagagttta ttaatgaacc actgaatgag
gttctagaaa tggataaaga ttatactttt ttcaaagtag
aaacagagaa caaattctct tttatgacat gtccctttat
attgaatgct gtcacaaaga atttgggatt atattatgac
aatagaattc gcatgtacag tgaacgaaga atcactgttc
tctacagctt agttcaagga cagcagttga atccatattt
gagactcaaa gttagacgtg accatatcat agatgatgca
cttgtccggg taagttgggc tgctagatta aaaacctaat
aatggggata tcatgataca gttcagtgaa ttcattttaa
aagtgactga aaaaaatgat accatatagc ataggaacac
atggacattt ctgatcttat ataagtatta tacttttgtt
gttcctgtgc aagtttatag atgtgttcta caaagtatcg
gttgtattat ataatggtca tgctatcttt gaaaaagaat
gggttttcta aatcttgaaa actaaatcca aagtttcttt
cattcagaag agaatagagt gttggacaaa gaccagaaca
agagaaatgt ggagataccc aataataagt gtggatgtgc
agtcttgaac tgggagtaat ggtacagtaa aaccatacca
taaaattata ggtagtgtcc aaaaaattcc atcgtgtaaa
attcagagtt gcattattgt ggacttgaag aagcagttgt
atgtgggacg gtatcgataa gcttgatatc gaattcctgc
```

-continued

```
agcccggggg atccactagt gtggtaatta atactaagtc
ttactgtgag agaccataaa ctgctttagt attcagtgta
tttttcttaa ttgaaatatt taacttatga cttagtagat
actaagactt aacccttgag tttctattct aataaaggac
tactaatgaa caattttgag gttagacctc tactccattg
tttttgctga aatgatttag ctgcttttcc atgtcctgtg
tagtccagac ttaacacaca agtaataaaa tcttaattaa
ttgtatgtta atttcataac aaatcagtaa agttagcttt
ttactatgct agtgtctgtt ttgtgtctgt ctttttgatt
atctttaaga ctgaatcttt gtcttcactg gctttttatc
agtttgcttt ctgtttccat ttacatacaa aaagtcaaaa
atttgtattt gtttcctaat cctactcctt gtttttattt
tgttttttc ctgatactag caatcatctt cttttcatgt
ttatcttttc aatcactagc tagagatgat cgctatggaa
aatcctgcag acttgaagaa gcagttgtat gtggaatttg
aaggagaaca aggagttgat gagggaggtg tttccaaaga
attttttcag ctggttgtgg aggaaatctt caatccagat
attggtaaat acattagtaa tgtgattatg gtgtcgtatc
atcttttgag ttagttattt gtttatctta ctttgtaaat
attttcagct atgaagagca gcaaaagaag gatttggtat
ggattaccca gaatcacaca tcatgactga atttgtaggt
tttaggaact gatttgtatc actaatttat tcaaattctt
ttatttctta gaaggaatat tctaatgaag gaaattatct
ctttggtaaa ctgaattgaa agcactttag aatggtatat
tggaacagtt ggagggattt ctttgctttt tgttgtctaa
aaccatcatc aaactcacgg ttttcctgac ctgtgaactt
caaagaacaa tggtttgaag agtattgaga gactgtctca
caagtatgtc atgctcaaag ttcagaaaca ctagctgata
tcacattaat taggtttatt tgctataaga tttcttgggg
cttaatatan gtagtgttcc cccaaacttt ttgaactcca
gaactctttt ctgccctaac agtagctact caggagctga
ggcaggagaa ttgtttgaac ctaggaggca gaggttgcag
tgagctgaga tcgtgccact ccagcccacc cctgggtaac
agagcgagac tccatctcaa agaaaaaaat gaaaaattgt
tttcaaaaat agtacgtgtg gtacagatat aagtaattat
atttttataa atgaaacact ttggaaatgt agccattttt
tgttttttta tgtttatttt tcagctatgg gtggataaag
catgaatata actttttcta tgtgttagta gaaaattaga
aagcttgaat ttaattaacg tatttttcta cccgatgcca
ccaaattact tactacttta ttcctttggc ttcataaaat
tacatatcac cattcacccc aatttatagc agatatatgt
```

-continued

```
ggacattgtt ttctcaagtg ctaatataat agaaatcaat
gttgcatgcc taattacata tattttaaat gttttatatg
cataattatt ttaagtttat atttgtatta ttcatcagtc
cttaataaaa tacaaaagta atgtattttt aaaaatcatt
tcttataggt atgttcacat acgatgaatc tacaaaattg
ttttggttta atccatcttc ttttgaaact gagggtcagt
ttactctgat tggcatagta ctgggtctgg ctatttacaa
taactgtata ctggatgtac attttcccat ggttgtctac
aggaagctaa tggggaaaaa aggaactttt cgtgacttgg
gagactctca cccagtaagt tctttgtcat ttttttaatt
cagtctctta gattttattt aaatgcaaaa atttaattta
tgtcaaaatt ttaaagtttt tgtttagaat ctttgttgat
actcttatca ataagataaa aatgttttaa tctgaccgaa
gtaccagaaa cacttaaaaa ctcaaagggg gacattttta
tatattgctg tcagcacgaa gctttcgtaa gattgatttc
atagagaagt gtttctaaac attttgtttg tgttttagtg
aaatcttaag agataggtaa aaatcagagt agccctggct
aagggtcttg gtagttacaa cgagtgtgcc tgctcctacc
acccccaccc ccaccttgag acaccacaga atttctcata
gagcacagtg tgaattctat tgctaaattg gtggtatggg
gtttctcagc agagaatggg acatcacagt gactgacaat
ctttctttta taggttggaa actatttggg ggactggagg
gatactgtct acacttttta caatttttat tgataagatt
tttgttgtct tctaagaaga gtgatataaa ttatttgttg
tattttgtag ttctatggtg gcctcaattt accatttctg
gttgctaggt tctatatcag agtttaaaag atttattgga
gtatgaaggg aatgtggaag atgacatgat gatcactttc
cagatatcac agacagatct tttggtaacc ccaatgatgt
atgatctaaa ggaaaatggt gataaaattc caattacaaa
tgaaaacagg aaggtaataa atgtttttat gtcacatttt
gtctcttcat taacactttc aaagcatgta tgcttataat
ttttaaagaa gtatctaata tagtctgtac aaaaaaaaaa
caagtaacta agtttatgta aatgctagag tccacttttc
taaatcttgg atataagttg gtatgaaagc acacagttgg
gcactaaagc ccccttttaga gaaagaggac atgaagcagg
agatagttaa tagctaagtg tggttgtagt ataaagcaag
aagcagggtg tttcttgtat taagctgtaa gcaggaacct
catgattaag gtctttatca cagaacaaat aaaaattaca
tttaatttac acatgtatat cctgtttgtg ataaaaatac
atttctgaaa agtatacttt acgtcagatt tgggttctat
```

-continued

```
tgactaaaat gtgttcatcg ggaatgggaa taacccagaa
cataacaagc aaaaaattat gacaaatata tagtatacct
ttaagaaaca tgtttatatt gatataattt tttgattaaa
tattatacac actaagggta caangcacat tttcctttta
tganttngat acagtagttt atgtgtcagt cagatacttc
cacatttttg ctgaactgga tacagtaagc agcttaccaa
atattctatg gtagaaaact nggacttcct ggtttgctta
aatcaaatat attgtactct cttaaaacgg ttggcattta
taaatagatg gatacatggt ttaaatgtgt ctgttnacat
acctagttga gagaacctaa agaattttct gcgtctccag
catttatatt cagttctgtt taatacatta tcgaaattga
catttataag tatgacagtt ttgtgtatat ggccttttca
tagcttaata ttggctgtaa cagagaattg tgaaattgta
agaagtagtt ttctttgtag gtgtaaaatt gaatttttaa
gaatattctt gacagtttta tgtatatggc cttttcatag
cttaatattg gctataacag agaattgtga aattgttaag
aagtaggtgt aaaattgaat ttttaagaat attcttgaat
gtttttttct tggaaaaatt aaaaagctat gcagcccaat
aacttgtgtt ttgtttgcat agcatattat aagaagttct
tgtgattaat gttttctaca ggaatttgtc aatctttatt
ctgactacat tctcaataaa tcagtagaaa aacagttcaa
ggcttttcgg agaggttttc atatggtgac caatgaatct
cccttaaagt acttattcag accagaagaa attgaattgc
ttatatgtgg aagccgggta agaaagcagg tgtctgcaaa
aagtcatgta tcgatttatt gtttgtaatg atacagtagt
atagcagata actaagacat attttcttga atttgcagaa
tctagatttc caagcactag aagaaactac agaatatgac
ggtggctata ccagggactc tgttctgatt aggtgaggta
cttagttctt cagaggaaga tttgattcac caaaggggtg
tgtgattttg cttcagacct ttatctctag gtactaattc
ccaaataagc aaactcacaa attgtcatct atatacttag
atttgtattt gtaatataat caccattttt cagagctaat
cttgtgattt atttcatgaa tgaagtgttg ttatatataa
gtctcatgta atctcctgca tttggcgtat ggattatcta
gtattcctca ctggttagag tatgcttact gctggttaga
agataattaa aataaggcta ccatgtctgc aatttttcct
ttcttttgaa ctctgcattt gtgaactgtt acatggcttc
ccaggatcaa gcacttttg agtgaaatgg tagtctttta
tttaattctt aagataatat gtccagatac atactagtat
ttccatttta caccctaaaa aactaagccc tgaattctca
cagaaagatg tagaggttcc cagttctatc tgcttttaaa
```

-continued

```
caaatgccct tactactcta ctgtctactt ctgtgtacta
catcatcgta tgtagttgtt tgcatttggg ccagttggtt
ggggcagggg tcttttttc ttttgtccct taatctgtat
cactttttcc tcccaaagtt gagttaaagg atgagtagac
caggagaata aaggagaaag gataaataaa atatataccc
aaaggcacct ggagttaatt tttccaaata ttcatttcag
tctttttcaa ttcataggat tttgtctttt gctcattact
gactgcataa tgtgattata ccatagttta aatagtcact
tcctgttact acacacttgg gttttctcaa tttttacta
ttgtagtact aatattttac tatattgtaa tctaatccaa
atttttacgt attcagagct gttcaggata aatttgcttg
gaaattttta aatcaccaga agtgatacta tcctgataat
taacttccaa gttgtctctt aatatagttt taatgcaaat
cataagctta tgttagtacc agtcataatg aatgccaaac
tgaaaccagt attgtatttt ttctcattag ggagttctgg
gaaatcgttc attcatttac agatgaacag aaaagactct
tcttgcagtt tacaacgggc acagacagag cacctgtggg
aggactagga aaattaaaga tgattatagc caaaaatggc
ccagacacag aaaggtaggt aattattaac ttgtgactgt
atacctaccg aaaaccttgc attcctcgtc acatacatat
gaactgtctt tatagtttct gagcacattc gtgattttat
atacaaatcc ccaaatcata ttagacaatt gagaaaatac
tttgctgtca ttgtgtgagg aaacttttaa gaaattgccc
tagttaaaaa ttattatggg gctcacattg gtttggaatc
aaattagtgt gattcattta ctttttttgat tcccagcttg
ttaattgaaa gccatataac atgatcatct atttagaatg
gttacattga ggctcggaag attatcattt gattgtgcta
gaatcctgtt atcaaatcat tttcttagtc atattgccag
cagtgtttct aataagcatt taagagcaca cactttgcag
tcttgtaaaa caggtttgag tattttctcc accttagagg
aagttacttg acttctcagt gacctaacct ctaaagtgca
tttactgatg tcctctctgt ggttttgttg tggaaagatt
tagttaaatg aactgtaaga attcagtacc taaaatggta
tctgttatgt agtaaaaact caatggatac agtatcttat
catcgtcact agctttgagt aatttatagg ataaaggcaa
cttggtagtt acacaacaaa aagtttatga tttgcattaa
tgtatagttt gcattgcaga ccgtctcaac tatatacaat
ctaaaaatag gagcatttaa ttctaagtgt atttcccatg
acttacagtt ttcctgtttt tttccccttt tctctattta
ggttacctac atctcatact tgctttaatg tgcttttact
```

-continued

```
tccggaatac tcaagcaaag aaaaacttaa agagagattg
ttgaaggcca tcacgtatgc caaaggattt ggcatgctgt
aaaacaaaac aaaacaaaat aaaacaaaaa aaaggaagga
aaaaaaaaga aaaaatttaa aaaattttaa aaatataacg
agggataaat ttt,
```

which encodes for;

```
(SEQ ID No. 7)
MKRAAAKHLIERYYHQLTEGCGNEACTNEFCASCPTFLRMDNNAAAI
KALELYKINAKLCDPHPSKKGASSAYLENSKGAPNNSCSEIKMNKKG
ARIDFKDVTYLTEEKVYEILELCREREDYSPLIRVIGRVFSSAEALV
QSFRKVKQHTKEELKSLQAKDEDKDEDEKEKAACSAAAMEEDSEASS
SRIGDSSQGDNNLQKLGPDDVSVDIDAIRRVYTRLLSNEKIETAFLN
ALVYLSPNVECDLTYHNVYSRDPNYLNLFIIVMENRNLHSPEYLEMA
LPLFCKAMSKLPLAAQGKLIRLWSKYNADQIRRMMETFQQLITYKVI
SNEFNSRNLVNDDDAIVAASKCLKMVYYANVVGGEVDTNHNEEDDEE
PIPESSELTLQELLGEERRNKKGPRVDPLETELGVKTLDCRKPLIPF
EEFINEPLNEVLEMDKDYTFFKVETENKFSFMTCPFILNAVTKNLGL
YYDNRIRMYSERRITVLYSLVQGQQLNPYLRLKVRRDHIIDDALVRL
EMIAMENPADLKKQLYVEFEGEQGVDEGGVSKEFFQLVVEEIFNPDI
GMFTYDESTKLFWFNPSSFETEGQFTLIGIVLGLAIYNNCILDVHFP
MVVYRKLMGKKGTFRDLGDSHPVLYQSLKDLLEYEGNVEDDMMITFQ
ISQTDLFGNPMMYDLKENGDKIPITNENRKEFVNLYSDYILNKSVEK
QFKAFRRGFHMVTNESPLKYLFRPEEIELLICGSRNLDFQALEETTE
YDGGYTRDSVLIREFWEIVHSFTDEQKRLFLQFTTGTDRAPVGGLGK
LKMIIAKNGPDTERLPTSHTCFNVLLLPEYSSKEKLKERLLKAITYA
KGFGML.
```

The cDNA was subcloned and sequenced. The UBE3A gene (SEQ ID No. 6) was fused to one of three genes encoding a secretion signaling peptide, based on GDNF;

```
(SEQ ID No. 8)
ATGAAGTTATGGGATGTCGTGGCTGTCTGCCTGGTGCTGCTCCACACCG
CGTCCGCC,
```

from insulin protein;

```
(SEQ ID No. 9)
ATGGCCCTGTGGATGCGCCTCCTGCCCCTGCTGGCGCTGCTGGCCCTCT
GGGGACCTGACCCAGCCGCAGCC,
```

or from IgK;

```
(SEQ ID NO. 10)
ATGGAGACAGACACACTCCTGCTATGGGTACTGCTGCTCTGGGTTCCAG
GTTCCACTGGT.
```

The construct was inserted into the hSTUb vector, under a CMV chicken-beta actin hybrid promoter or human ubiquitin c promoter. Woodchuck hepatitis post-transcriptional regulatory element (WPRE) is present to increase expression levels.

The UBE3A-secretion signal construct was then attached to a cellular uptake peptide (cell penetrating peptide); either a HIV TAT sequence (SEQ ID No. 5)
YGRKKRRQRRR; or HIV TATk Sequence (SEQ ID NO. 11)
YARKAARQARA.

Figure 21:
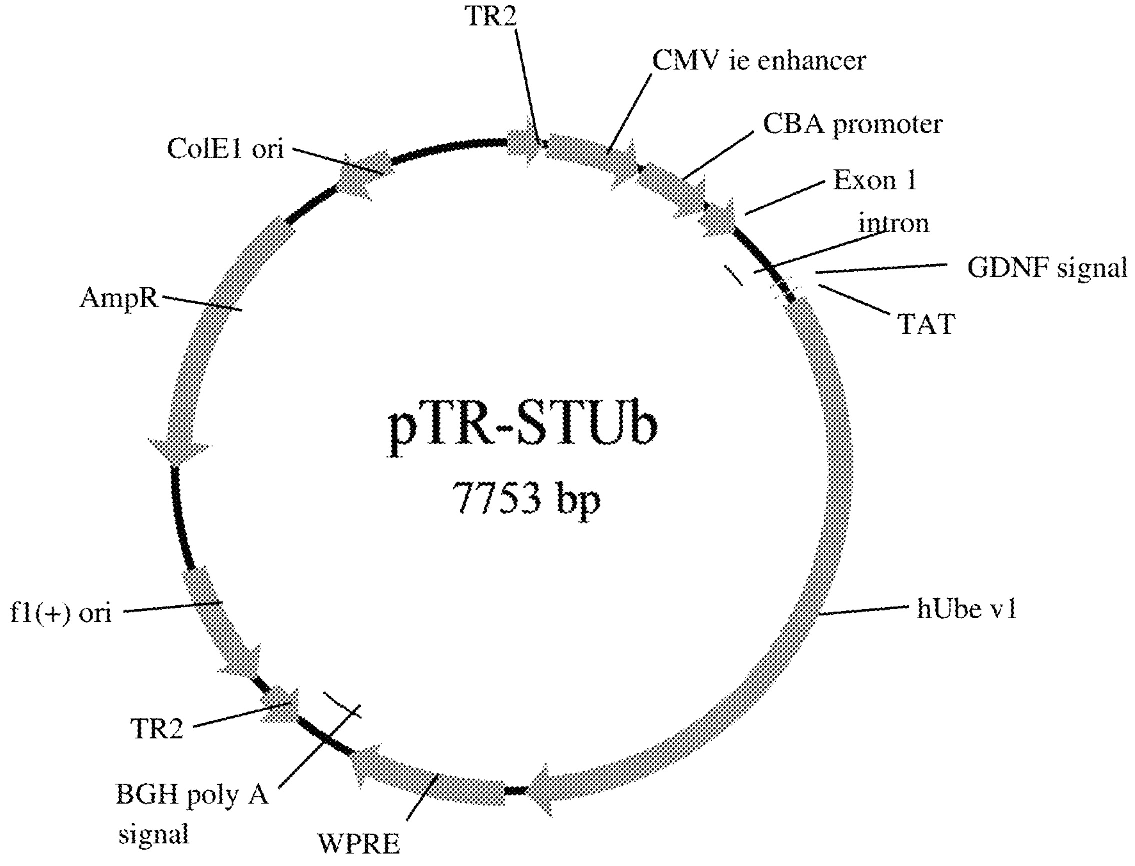
FIG. 21 is a map of the human UBE3A vector construct used in the present invention. Major genes are noted.

The human UBE3A vector, seen in FIG. 21, is then transformed into *E. coli* using the heat shock method described in Example 2. The transformed *E. coli* were expanded in broth containing ampicillin to select for the vector and collect large amounts of vector.

Other sequences of UBE3A include variants 1, 2, or 3, seen below;

*H sapiens* UBE3A variant 1:

(SEQ ID No. 12)
```
acagtatgac atctgatgct ggagggtcgc actttcacaa
atgagtcagc tggtacatgg ggttatcatc aatttttagc
tcttctgtct gggagataca agtttggaag caatcttggg
gtacttaccc acaaggctgg tggagaccag atcaggagaa
cctcagtctg acgacattga agctagccga atgaagcgag
cagctgcaaa gcatctaata gaacgctact accaccagtt
aactgagggc tgtggaaatg aagcctgcac gaatgagttt
tgtgcttcct gtccaacttt tcttcgtatg gataataatg
cagcagctat taaagccctc gagctttata agattaatgc
aaaactctgt gatcctcatc cctccaagaa aggagcaagc
tcagcttacc ttgagaactc gaaaggtgcc cccaacaact
cctgctctga gataaaaatg aacaagaaag gcgctagaat
tgattttaaa gatgtgactt acttaacaga agagaaggta
tatgaaattc ttgaattatg tagagaaaga gaggattatt
cccctttaat ccgtgttatt ggaagagttt tttctagtgc
tgaggcattg gtacagagct tccggaaagt taaacaacac
accaaggaag aactgaaatc tcttcaagca aaagatgaag
acaaagatga ggatgaaaag gaaaaagctg catgttctgc
tgctgctatg gaagaagact cagaagcatc ttcctcaagg
ataggtgata gctcacaggg agacaacaat ttgcaaaaat
taggccctga tgatgtgtct gtggatattg atgccattag
aagggtctac accagattgc tctctaatga aaaaattgaa
actgcctttc tcaatgcact tgtatatttg tcacctaacg
tggaatgtga cttgacgtat cacaatgtat actctcgaga
tcctaattat ctgaatttgt tcattatcgt aatggagaat
agaaatctcc acagtcctga atatctggaa atggctttgc
cattattttg caaagcgatg agcaagctac cccttgcagc
```

-continued
```
ccaaggaaaa ctgatcagac tgtggtctaa atacaatgca
gaccagattc ggagaatgat ggagacattt cagcaactta
ttacttataa agtcataagc aatgaattta acagtcgaaa
tctagtgaat gatgatgatg ccattgttgc tgcttcgaag
tgcttgaaaa tggtttacta tgcaaatgta gtgggagggg
aagtggacac aaatcacaat gaagaagatg atgaagagcc
catccctgag tccagcgagc tgacacttca ggaacttttg
ggagaagaaa gaagaaacaa gaaaggtcct cgagtggacc
ccctggaaac tgaacttggt gttaaaaccc tggattgtcg
aaaaccactt atcccttttg aagagtttat taatgaacca
ctgaatgagg ttctagaaat ggataaagat tatacttttt
tcaaagtaga aacagagaac aaattctctt ttatgacatg
tccctttata ttgaatgctg tcacaaagaa tttgggatta
tattatgaca atagaattcg catgtacagt gaacgaagaa
tcactgttct ctacagctta gttcaaggac agcagttgaa
tccatatttg agactcaaag ttagacgtga ccatatcata
gatgatgcac ttgtccggct agagatgatc gctatggaaa
atcctgcaga cttgaagaag cagttgtatg tggaatttga
aggagaacaa ggagttgatg agggaggtgt ttccaaagaa
ttttttcagc tggttgtgga ggaaatcttc aatccagata
ttggtatgtt cacatacgat gaatctacaa aattgttttg
gtttaatcca tcttcttttg aaactgaggg tcagtttact
ctgattggca tagtactggg tctggctatt tacaataact
gtatactgga tgtacatttt cccatggttg tctacaggaa
gctaatgggg aaaaaaggaa cttttcgtga cttgggagac
tctcacccag ttctatatca gagtttaaaa gatttattgg
agtatgaagg gaatgtggaa gatgacatga tgatcacttt
ccagatatca cagacagatc tttttggtaa cccaatgatg
tatgatctaa aggaaaatgg tgataaaatt ccaattacaa
atgaaaacag gaaggaattt gtcaatcttt attctgacta
cattctcaat aaatcagtag aaaaacagtt caaggctttt
cggagaggtt ttcatatggt gaccaatgaa tctcccttaa
agtacttatt cagaccagaa gaaattgaat tgcttatatg
tggaagccgg aatctagatt tccaagcact agaagaaact
acagaatatg acggtggcta taccagggac tctgttctga
ttagggagtt ctgggaaatc gttcattcat ttacagatga
acagaaaaga ctcttcttgc agtttacaac gggcacagac
agagcacctg tgggaggact aggaaaatta aagatgatta
tagccaaaaa tggcccagac acagaaaggt tacctacatc
tcatacttgc tttaatgtgc ttttacttcc ggaatactca
```

-continued agcaaagaaa aacttaaaga gagattgttg aaggccatca cgtatgccaa aggatttggc atgctgtaaa acaaaacaaa acaaaat;

*H sapiens* UBE3A Variant 2;

(SEQ ID No. 13)

agccagtcct cccgtcttgc gccgcggccg cgagatccgt gtgtctccca agatggtggc gctgggctcg ggtgactac aggagacgac ggggcctttt cccttcgcca ggacccgaca caccaggctt cgctcgctcg cgcacccctc cgccgcgtag ccatccgcca gcgcgggcgc ccgccatccg ccgcctactt acgcttcacc tctgccgacc cggcgcgctc ggctgcgggc ggcggcgcct ccttcggctc ctcctcggaa tagctcgcgg cctgtagccc ctggcaggag ggcccctcag ccccccggtg tggacaggca gcggcggctg gcgacgaacg ccgggatttc ggcggccccg gcgctccctt tcccggcctc gttttccgga taaggaagcg cgggtcccgc atgagccccg gcggtggcgg cagcgaaaga gaacgaggcg gtggcgggcg gaggcggcgg gcgagggcga ctacgaccag tgaggcggcc gccgcagccc aggcgcgggg gcgacgacag gttaaaaatc tgtaagagcc tgattttaga attcaccagc tcctcagaag tttggcgaaa tatgagttat taagcctacg ctcagatcaa ggtagcagct agactggtgt gacaacctgt ttttaatcag tgactcaaag ctgtgatcac cctgatgtca ccgaatggcc acagcttgta aaagagagtt acagtggagg taaaaggagt ggcttgcagg atggagaagc tgcaccagtg ttattggaaa tcaggagaac ctcagtctga cgacattgaa gctagccgaa tgaagcgagc agctgcaaag catctaatag aacgctacta ccaccagtta actgagggct gtggaaatga agcctgcacg aatgagtttt gtgcttcctg tccaactttt cttcgtatgg ataataatgc agcagctatt aaagccctcg agctttataa gattaatgca aaactctgtg atcctcatcc ctccaagaaa ggagcaagct cagcttacct tgagaactcg aaaggtgccc ccaacaactc ctgctctgag ataaaaatga acaagaaagg cgctagaatt gattttaaag atgtgactta cttaacagaa gagaaggtat atgaaattct tgaattatgt agagaaagag aggattattc ccctttaatc cgtgttattg gaagagtttt ttctagtgct gaggcattgg tacagagctt ccggaaagtt aaacaacaca ccaaggaaga actgaaatct cttcaagcaa aagatgaaga caaagatgaa gatgaaaagg aaaaagctgc atgttctgct gctgctatgg aagaagactc agaagcatct tcctcaagga -continued taggtgatag ctcacaggga gacaacaatt tgcaaaaatt aggccctgat gatgtgtctg tggatattga tgccattaga agggtctaca ccagattgct ctctaatgaa aaaattgaaa ctgcctttct caatgcactt gtatatttgt cacctaacgt ggaatgtgac ttgacgtatc acaatgtata ctctcgagat cctaattatc tgaatttgtt cattatcgta atggagaata gaaatctcca cagtcctgaa tatctggaaa tggctttgcc attattttgc aaagcgatga gcaagctacc ccttgcagcc caaggaaaac tgatcagact gtggtctaaa tacaatgcag accagattcg gagaatgatg gagacatttc agcaacttat tacttataaa gtcataagca atgaatttaa cagtcgaaat ctagtgaatg atgatgatgc cattgttgct gcttcgaagt gcttgaaaat ggtttactat gcaaatgtag tgggagggga agtggacaca aatcacaatg aagaagatga tgaagagccc atccctgagt ccagcgagct gacacttcag gaacttttgg gagaagaaag aagaaacaag aaaggtcctc gagtggaccc cctggaaact gaacttggtg ttaaaaccct ggattgtcga aaaccactta tccctttga agagtttatt aatgaaccac tgaatgaggt tctagaaatg gataaagatt atactttttt caaagtagaa acagagaaca aattctcttt tatgacatgt ccctttatat tgaatgctgt cacaaagaat ttgggattat attatgacaa tagaattcgc atgtacagtg aacgaagaat cactgttctc tacagcttag ttcaaggaca gcagttgaat ccatatttga gactcaaagt tagacgtgac catatcatag atgatgcact tgtccggcta gagatgatcg ctatggaaaa tcctgcagac ttgaagaagc agttgtatgt ggaatttgaa ggagaacaag gagttgatga gggaggtgtt tccaaagaat tttttcagct ggttgtggag gaaatcttca atccagatat tggtatgttc acatacgatg aatctacaaa attgttttgg tttaatccat cttcttttga aactgagggt cagtttactc tgattggcat agtactgggt ctggctattt acaataactg tatactggat gtacattttc ccatggttgt ctacaggaag ctaatgggga aaaaaggaac ttttcgtgac ttgggagact ctcacccagt tctatatcag agtttaaaag atttattgga gtatgaaggg aatgtggaag atgacatgat gatcactttc cagatatcac agacagatct tttgggtaac ccaatgatgt atgatctaaa ggaaaatggt gataaaattc caattacaaa tgaaaacagg aaggaatttg tcaatcttta ttctgactac attctcaata aatcagtaga aaaacagttc aaggcttttc ggagaggttt tcatatggtg accaatgaat ctcccttaaa gtacttattc agaccagaag aaattgaatt gcttatatgt -continued ggaagccgga atctagattt ccaagcacta gaagaaacta
cagaatatga cggtggctat accagggact ctgttctgat
tagggagttc tgggaaatcg ttcattcatt tacagatgaa
cagaaaagac tcttcttgca gtttacaacg ggcacagaca
gagcacctgt gggaggacta ggaaaattaa agatgattat
agccaaaaat ggcccagaca cagaaaggtt acctacatct
catacttgct ttaatgtgct tttacttccg gaatactcaa
gcaaagaaaa acttaaagag agattgttga aggccatcac
gtatgccaaa ggatttggca tgctgtaaaa caaaacaaaa
caaaataaaa caaaaaaaag gaaggaaaaa aaaagaaaaa
atttaaaaaa ttttaaaaat ataacgaggg ataaattttt
ggtggtgata gtgtcccagt acaaaaaggc tgtaagatag
tcaaccacag tagtcaccta tgtctgtgcc tcccttcttt
attggggaca tgtgggctgg aacagcagat ttcagctaca
tatatgaaca aatcctttat tattattata attatttttt
tgcgtgaaag tgttacatat tctttcactt gtatgtacag
agaggttttt ctgaatattt attttaaggg ttaaatcact
tttgcttgtg tttattactg cttgaggttg agccttttga
gtatttaaaa aatatatacc aacagaacta ctctcccaag
gaaaatattg ccaccatttg tagaccacgt aaccttcaag
tatgtgctac ttttttgtcc ctgtatctaa ctcaaatcag
gaactgtatt ttttttaatg atttgctttt gaaacttgaa
gtcttgaaaa cagtgtgatg caattactgc tgttctagcc
cccaaagagt tttctgtgca aaatcttgag aatcaatcaa
taaagaaaga tggaaggaag ggagaaattg gaatgtttta
actgcagccc tcagaacttt agtaacagca caacaaatta
aaaacaaaaa caactcatgc cacagtatgt cgtcttcatg
tgtcttgcaa tgaactgttt cagtagccaa tcctctttct
tagtatatga aaggacaggg atttttgttc ttgttgttct
cgttgttgtt ttaagtttac tggggaaagt gcatttggcc
aaatgaaatg gtagtcaagc ctattgcaac aaagttagga
agtttgttgt ttgtttatta taaacaaaaa gcatgtgaaa
gtgcacttaa gatagagttt ttattaatta cttacttatt
acctagattt taaatagaca atccaaagtc tccccttcgt
gttgccatca tcttgttgaa tcagccattt tatcgaggca
cgtgatcagt gttgcaacat aatgaaaaag atggctactg
tgccttgtgt tacttaatca tacagtaagc tgacctggaa
atgaatgaaa ctattactcc taagaattac attgtatagc
cccacagatt aaatttaatt aattaattca aaacatgtta
aacgttactt tcatgtacta tggaaaagta caagtaggtt -continued tacattactg atttccagaa gtaagtagtt tccccttttcc
tagtcttctg tgtatgtgat gttgttaatt tcttttattg
cattataaaa taaaaggatt atgtattttt aactaaggtg
agacattgat atatcctttt gctacaagct atagctaatg
tgctgagctt gtgccttggt gattgattga ttgattgact
gattgtttta actgattact gtagatcaac ctgatgattt
gtttgtttga aattggcagg aaaaatgcag ctttcaaatc
attgggggga gaaaaaggat gtctttcagg attattttaa
ttaatttttt tcataattga gacagaactg tttgttatgt
accataatgc taaataaaac tgtggcactt ttcaccataa
tttaatttag tggaaaaaga agacaatgct ttccatattg
tgataaggta acatggggtt tttctgggcc agcctttaga
acactgttag ggtacatacg ctaccttgat gaaaggggacc
ttcgtgcaac tgtagtcatc ttaaaggctt ctcatccact
gtgcttctta atgtgtaatt aaagtgagga gaaattaaat
actctgaggg cgttttatat aataaattcg tgaaga, which encodes the protein:

(SEQ ID No. 14)

meklhqcywk sgepqsddie asrmkraaak hlieryyhql
tegcgneact nefcascptf lrmdnnaaai kalelykina
klcdphpskk gassaylens kgapnnscse ikmnkkgari
dfkdvtylte ekvyeilelc reredyspli rvigrvfssa
ealvqsfrkv kqhtkeelks lqakdedkde dekekaacsa
aameedseas ssrigdssqg dnnlqklgpd dvsvdidair
rvytrllsne kietaflnal vylspnvecd ltyhnvysrd
pnylnlfiiv menrnlhspe ylemalplfc kamsklplaa
qgklirlwsk ynadqirrmm etfqqlityk visnefnsrn
lvndddaiva askclkmvyy anvvggevdt nhneeddeep
ipesseltlq ellgeerrnk kgprvdplet elgvktlder
kplipfeefi neplnevlem dkdytffkve tenkfsfmtc
pfilnavtkn lglyydnrir myserritvl yslvqgqqln
pylrlkvrrd hiiddalvrl emiamenpad Ikkqlyvefe
geqgvdeggv skeffqlvve eifnpdigmf tydestklfw
fnpssfeteg qftligivlg laiynncild vhfpmvvyrk
lmgkkgtfrd lgdshpvlyq slkdlleyeg nveddmmitf
qisqtdlfgn pmmydlkeng dkipitnenr kefvnlysdy
ilnksvekqf kafrrgfhmv tnesplkylf rpeeiellic
gsrnldfqal eetteydggy trdsvliref weivhsftde
qkrlflqftt gtdrapvggl gklkmiiakn gpdterlpts
htcfnvlllp eysskeklke rllkaityak gfgml;

*H sapiens* UBE3A Variant 3

(SEQ ID No. 15)

```
tttttccgga taaggaagcg cgggtcccgc atgagccccg
gcggtggcgg cagcgaaaga gaacgaggcg gtggcgggcg
gaggcggcgg gcgagggcga ctacgaccag tgaggcggcc
gccgcagccc aggcgcgggg gcgacgacag gttaaaaatc
tgtaagagcc tgatttttaga attcaccagc tcctcagaag
tttggcgaaa tatgagttat taagcctacg ctcagatcaa
ggtagcagct agactggtgt gacaacctgt ttttaatcag
tgactcaaag ctgtgatcac cctgatgtca ccgaatggcc
acagcttgta aaagatcagg agaacctcag tctgacgaca
ttgaagctag ccgaatgaag cgagcagctg caaagcatct
aatagaacgc tactaccacc agttaactga gggctgtgga
aatgaagcct gcacgaatga gttttgtgct tcctgtccaa
cttttcttcg tatggataat aatgcagcag ctattaaagc
cctcgagctt tataagatta atgcaaaact ctgtgatcct
catccctcca agaaaggagc aagctcagct taccttgaga
actcgaaagg tgcccccaac aactcctgct ctgagataaa
aatgaacaag aaaggcgcta gaattgattt taaagatgtg
acttacttaa cagaagagaa ggtatatgaa attcttgaat
tatgtagaga aagagaggat tattcccctt taatccgtgt
tattggaaga gtttttttcta gtgctgaggc attggtacag
agcttccgga aagttaaaca acacaccaag gaagaactga
aatctcttca agcaaaagat gaagacaaag atgaagatga
aaaggaaaaa gctgcatgtt ctgctgctgc tatggaagaa
gactcagagg catcttcctc aaggataggt gatagctcac
agggagacaa caatttgcaa aaattaggcc ctgatgatgt
gtctgtggat attgatgcca ttagaagggt ctacaccaga
ttgctctcta atgaaaaaat tgaaactgcc tttctcaatg
cacttgtata tttgtcacct aacgtggaat gtgacttgac
gtatcacaat gtatactctc gagatcctaa ttatctgaat
ttgttcatta tcgtaatgga gaatagaaat ctccacagtc
ctgaatatct ggaaatggct ttgccattat tttgcaaagc
gatgagcaag ctaccccttg cagcccaagg aaaactgatc
agactgtggt ctaaatacaa tgcagaccag attcggagaa
tgatggagac atttcagcaa cttattactt ataaagtcat
aagcaatgaa tttaacagtc gaaatctagt gaatgatgat
gatgccattg ttgctgcttc gaagtgcttg aaaatggttt
actatgcaaa tgtagtggga ggggaagtgg acacaaatca
caatgaagaa gatgatgaag agcccatccc tgagtccagc
gagctgacac ttcaggaact tttgggagaa gaaagaagaa
```

-continued

```
acaagaaagg tcctcgagtg gaccccctgg aaactgaact
tggtgttaaa accctggatt gtcgaaaacc acttatccct
tttgaagagt ttattaatga accactgaat gaggttctag
aaatggataa agattatact tttttcaaag tagaaacaga
gaacaaattc tcttttatga catgtccctt tatattgaat
gctgtcacaa agaatttggg attatattat gacaatagaa
ttcgcatgta cagtgaacga agaatcactg ttctctacag
cttagttcaa ggacagcagt tgaatccata tttgagactc
aaagttagac gtgaccatat catagatgat gcacttgtcc
ggctagagat gatcgctatg gaaaatcctg cagacttgaa
gaagcagttg tatgtggaat ttgaaggaga acaaggagtt
gatgagggag gtgtttccaa agaatttttt cagctggttg
tggaggaaat cttcaatcca gatattggta tgttcacata
cgatgaatct acaaaattgt tttggtttaa tccatcttct
tttgaaactg agggtcagtt tactctgatt ggcatagtac
tgggtctggc tatttacaat aactgtatac tggatgtaca
ttttcccatg gttgtctaca ggaagctaat ggggaaaaaa
ggaacttttc gtgacttggg agactctcac ccagttctat
atcagagttt aaaagattta ttggagtatg aagggaatgt
ggaagatgac atgatgatca ctttccagat atcacagaca
gatcttttg gtaacccaat gatgtatgat ctaaaggaaa
atggtgataa aattccaatt acaaatgaaa acaggaagga
atttgtcaat ctttattctg actacattct caataaatca
gtagaaaaac agttcaaggc ttttcggaga ggttttcata
tggtgaccaa tgaatctccc ttaaagtact tattcagacc
agaagaaatt gaattgctta tatgtggaag ccggaatcta
gatttccaag cactagaaga aactacagaa tatgacggtg
gctataccag ggactctgtt ctgattaggg agttctggga
aatcgttcat tcatttacag atgaacagaa aagactcttc
ttgcagttta caacgggcac agacagagca cctgtgggag
gactaggaaa attaaagatg attatagcca aaaatggccc
agacacagaa aggttaccta catctcatac ttgctttaat
gtgcttttac ttccggaata ctcaagcaaa gaaaaactta
aagagagatt gttgaaggcc atcacgtatg ccaaaggatt
tggcatgctg taaaacaaaa caaaacaaaa taaaacaaaa
aaaaggaagg.
```

Example 6

Human vector properties were tested in HEK293 cells (American Type Culture Collection, Manassas, VA), grown at 37° C. 5% $CO_2$ in DMEM with 10% FBS and 1% Pen/Strep and subcultured at 80% confluence.

The vector (2 μg/well in a 6-well plate) was transfected into the cells using PEI transfection method. The cells were subcultured at $0.5\times10^6$ cells per well in a 6-well plate with DMEM medium two days before the transfection. Medium was replaced the night before transfection. Endotoxin-free $dH_2O$ was heated to around 80° C., and polyethylenimine (Sigma-Aldrich Co. LLC, St. Louis, MO) dissolved. The solution was allowed to cool to around 25° C., and the solution neutralized using sodium hydroxide. AAV4-STUb vector or negative control (medium only) was added to serum-free DMEM at 2 μg to every 200 μl for each well transfected, and 9 μl of 1 μg/μl polyethylenimine added to the mix for each well. The transfection mix was incubated at room temperature for 15 minutes, then added to each well of cells at 210 μl per well and incubated for 48 hours. Cells and media were harvested by scraping the cells from the plates. The medium and cells were then centrifuged at 5000×g for 5 minutes.

For Western blotting of the extracts, cell pellets were resuspended in 50 μL of hypo-osmotic buffer and the cells lysed by three repeated freeze/thaws. 15 μL of lysate was heated with Lamelli sample buffer and run on a BioRad 4-20% acrylamide gel. Transferred to nitrocellulose membrane using a TransBlot. The blot was blocked with 5% milk and protein detected using an anti-E6AP antibody.

Figure 22:
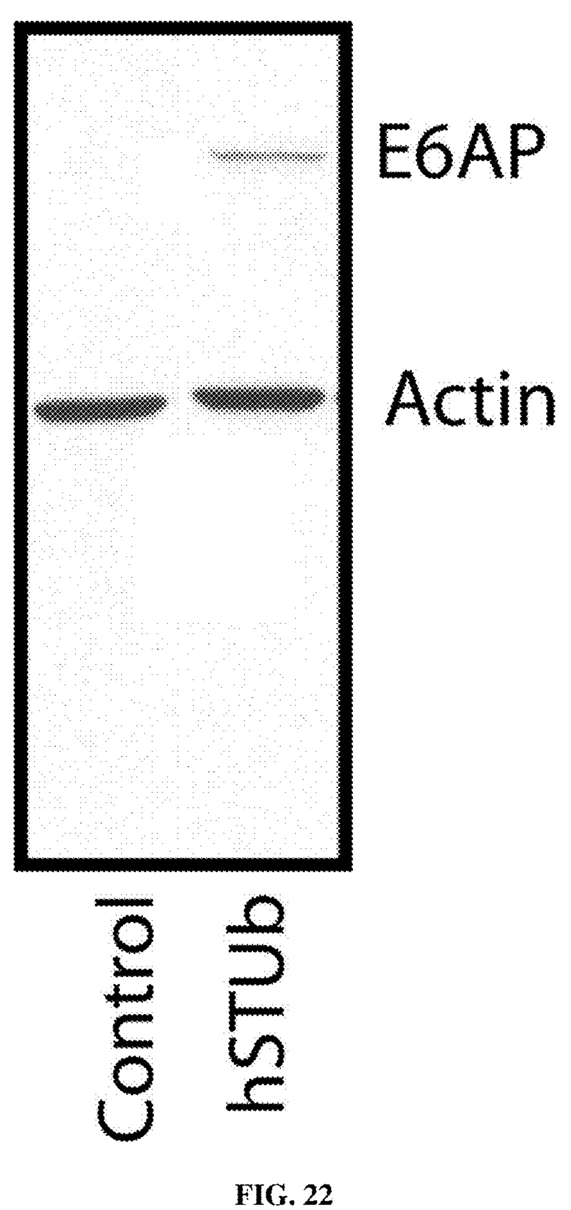
FIG. 22 is a Western blot of HEK293 cell lysate transfected with hSTUb construct. The proteins were stained with anti-E6AP.
Figures 23, 24:
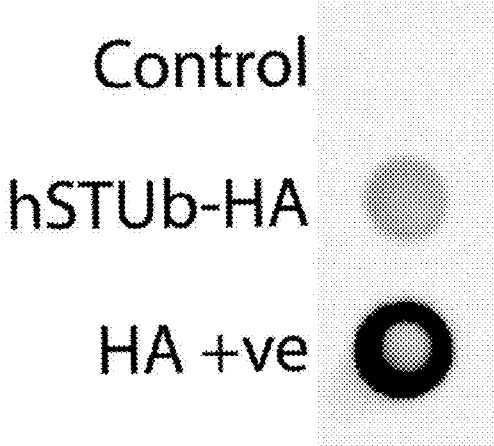
FIG. 23 is a dot blot with Anti-E6AP of HEK293 cells transfected with hSTUb construct with GDNF signal or insulin signal, shows insulin signal works better for expression and secretion.
FIG. 24 is a dot blot confirming insulin signal secretion using anti-HA tag antibody.

As seen in FIG. 22, cells transfected with the construct express the UBE3A gene, i.e. E6-AP. Furthermore, appending the gene to the various secretion signals exhibited mixed results, based on the secretion signal peptide. For example, transfection using constructs based on the GDNF secretion signal exhibited less expression and no detectable secretion from the transfected cells, as seen in FIG. 23. Use of the insulin secretion signal resulted in moderate secretion of E6AP from transfected cells, along with high expression of the construct within the cell. The results of insulin-signal secretion were confirmed using an HA-tagged construct, as seen in FIG. 24.

The sequence listing entitled "Modified UBE3A Gene for a Gene Therapy Approach for Angelman Syndrome" in XML format, created on May 3, 2023, and being 44,000 bytes in size, is hereby incorporated by reference into this disclosure.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of a method of treating UBE3A deficiencies, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. A ubiquitin protein ligase E3A (UBE3A) vector comprising:

a transcription initiation sequence wherein the transcription initiation sequence is a cytomegalovirus chicken-beta actin hybrid promoter, or human ubiquitin c promoter, a UBE3A sequence disposed downstream of the transcription initiation sequence, wherein the UBE3A sequence is SEQ ID NO: 12, SEQ ID NO: 13, SEQ ID NO: 15, a cDNA encoding SEQ ID NO: 7, a cDNA encoding SEQ ID NO: 14, or a nucleotide sequence possessing at least 90% sequence identity thereto;

a secretion sequence disposed downstream of the transcription initiation sequence and upstream of the UBE3A sequence, wherein the secretion sequence is SEQ ID NO: 2, SEQ ID NO: 8, SEQ ID NO: 9, SEQ ID NO: 10, a cDNA encoding SEQ ID NO: 3, or a homologous sequence; and a cell uptake sequence disposed downstream of the transcription initiation sequence and between the secretion sequence and the UBE3A sequence, wherein the cell uptake sequence is SEQ ID NO: 4, a cDNA encoding SEQ ID NO: 5, SEQ ID NO: 11, or a homologous sequence;

wherein the vector is an adeno-associated viral (AAV) vector.

2. The vector of claim 1, further comprising a cytomegalovirus immediate-early enhancer sequence disposed upstream of the transcription initiation sequence.

3. The vector of claim 1, further comprising a woodchuck hepatitis post-transcriptional regulatory element.

4. A method of treating a UBE3A deficiency disease, comprising:

administering the vector of claim 1 to the brain of a patient suffering from the UBE3A deficiency disease;

wherein the UBE3A deficiency disease is Angelman syndrome, Prader-Willi syndrome, or Huntington's disease.

5. The method of claim 4, wherein the administering a vector to the brain comprises injecting the vector into the brain.

6. The method of claim 5, wherein the vector is injected into the hippocampus or ventricle.

7. The method of claim 6, wherein the vector is injected bilaterally.

8. The method of claim 4, wherein the vector is administered at about $5.55\times10^{11}$ to about $2.86\times10^{12}$ genomes/g brain mass.

9. The method of claim 4, wherein the vector is administered at $5.55\times10^{11}$ to $2.86\times10^{12}$ genomes/g brain mass, $2.86\times10^{12}$ genomes/g brain mass, $2.40\times10^{12}$ genomes/g brain mass, $9.80\times10^{11}$ genomes/g brain mass, or $5.55\times10^{11}$ genomes/g brain mass.

* * * * *